US009701969B2

(12) United States Patent
Bower et al.

(10) Patent No.: US 9,701,969 B2
(45) Date of Patent: Jul. 11, 2017

(54) FILAMENTOUS FUNGAL HOST STRAINS AND DNA CONSTRUCTS, AND METHODS OF USE THEREOF

(75) Inventors: Benjamin S. Bower, Newark, CA (US); Thijs Kaper, Half Moon Bay, CA (US); Bradley R. Kelemen, Menlo Park, CA (US)

(73) Assignee: DANISCO US INC., Palo Alto, CA (US)

( * ) Notice: Subject to any disclaimer, the term of this patent is extended or adjusted under 35 U.S.C. 154(b) by 0 days.

(21) Appl. No.: 13/701,479

(22) PCT Filed: Jun. 3, 2011

(86) PCT No.: PCT/US2011/039092
§ 371 (c)(1),
(2), (4) Date: Feb. 1, 2013

(87) PCT Pub. No.: WO2011/153449
PCT Pub. Date: Dec. 8, 2011

(65) Prior Publication Data
US 2013/0149742 A1 Jun. 13, 2013

Related U.S. Application Data

(60) Provisional application No. 61/351,286, filed on Jun. 3, 2010.

(51) Int. Cl.
C12N 15/80 (2006.01)
C12P 21/02 (2006.01)
C12N 9/42 (2006.01)

(52) U.S. Cl.
CPC ........... *C12N 15/80* (2013.01); *C12N 9/2437* (2013.01); *C12P 21/02* (2013.01); *C12Y 302/01091* (2013.01); Y02P 20/52 (2015.11)

(58) Field of Classification Search
None
See application file for complete search history.

(56) References Cited

U.S. PATENT DOCUMENTS

| | | | |
|---|---|---|---|
| 5,246,853 A | 9/1993 | Clarkson et al. | |
| 5,475,101 A | 12/1995 | Ward et al. | |
| 6,255,115 B1 | 7/2001 | Beijersbergen et al. | |
| 2006/0003408 A1 | 1/2006 | Dunn-Coleman et al. | |
| 2006/0094080 A1 | 5/2006 | Dunn-Coleman et al. | |
| 2006/0205042 A1 | 9/2006 | Aehle et al. | |

FOREIGN PATENT DOCUMENTS

| | | |
|---|---|---|
| WO | WO92/06209 | 4/1992 |
| WO | WO94/28117 | 12/1994 |
| WO | WO2005/001036 | 1/2005 |
| WO | WO2006/110901 | 10/2006 |
| WO | WO2007/115886 | 10/2007 |
| WO | WO2008/039370 | 4/2008 |
| WO | WO2008/113847 | 9/2008 |
| WO | WO 2008113847 A2 * | 9/2008 |
| WO | WO2010/141779 | 12/2010 |
| WO | WO2011/038019 | 3/2011 |

OTHER PUBLICATIONS

Storms et al., Plasmid, 2005, vol. 53, pp. 191-204.*
Catlett et al., Fungal Genetic Newsletter, 2003, vol. 50, pp. 1-7.*
Bajar, A., et al., "Identification of a fungal cutinase promoter that is inducible by a plant signal via a phosphorylated trans-acting factor." *Proc. Natl. Acad. Sci. USA* 88: 8202-8212, (1991).
Berges, T., et al., "Isolation of uridine auxotrophs from *Trichoderma reesei* and efficient transformation with the closed ura3 and ura5 genes." *Curr. Genet.* 19: 359-365, 1991.
Berka, R.M., et al., "Molecular cloning and deletion of the gene encoding aspergillopepsin A from *Aspergillus awamori.*" *Gene* 86(2): 153-162, 1990.
Blakeney, A.B., et al., "A Simple Colorimetric Method for the Determination of Sugars in Fruit and Vegetables." *J. Sci. Food Agric.* 31, 889-897, 1980.
Brigidi, P., et al., "Genetic transformation of intact cells of *Bacillus subtilis* by electroporation." *FEMS Microbiol. Lett.* 67: 135-138, 1990.
Campbell, E.I., et al. "Improved transformation efficiency of *Aspergillus niger* using the homologous niaD gene for nitrate reductase." *Curr. Genet.* 16: 53-56, 1989.
Carvalho, N.D.S.P., et al., "Expanding the ku70 toolbox for filamentous fungi: establishment of complementation vectos and receipt strains for advanced gene analyses." *Applied Microbiology and Biotechnology* 87(4): 1463-1473, 2010.
Goedegebuur, F., et al., "Cloning and relational analysis of 15 novel fungal endoglucanases from family 12 glycosyl hydrolase." *Curr. Genet* 41: 89-98, 2002.
Goldman, G.H., et al., "Transformation of *Trichoderma harzianum* by high-voltage electric pulse." *Curr. Genet.* 17: 169-174, 1990.
Guangtao, Z., et al., "Gene targeting in a nonhomologous end joining deficient *Hypocrea jecorina.*" *Journal of Biotechnology*, 139(2): 146-151, 2009.
Henry, R. J., "A Rapid Method for the Determination of Diastatic Power." *J. Inst. Brew.* 90: 37-39, 1984.
Ilmen, M. et al., "Regulation of Cellulase Gene Expression in the Filamentous Fungus *Trichoderma reesei.*" *Appl. Environ. Microbiol.* 63(4): 1298-1306, 1997.
Karlsson, J. et al., "Homologous expression and characterization of Cel61A (EG IV) of *Trichoderma reesei.*" *Eur. J. Biochem.* 268: 6498-6507, 2001.
Kuhls, K., et al., "Molecular evidence that the asexual industrial fungus *Trichoderma reesei* is a clonal derivative of the ascomycete *Hypocrea jecorina.*" *Proc. Natl. Acad Sci. USA* 93: 7755-7760,1996.
Lever, M., "A New Reaction for Colorimetric Determination of Carbohydrates." *Anal. Biochem.* 47: 273-279, 1972.
Lorito, M., et al., "Biolistic transformation of *Trichoderma harzianum* and *Gliocladium virens* using plasmid and genomic DNA." *Curr. Genet.* 24: 349-356, 1993.
Penttila, M. et al., "EGIII, a new endoglucanase from *Trichoderma reesei*: the characterization of both gene and enzyme." *Gene* 63: 11-22, 1988.

(Continued)

*Primary Examiner* — Mindy G Brown
(74) *Attorney, Agent, or Firm* — Danisco US Inc.

(57) ABSTRACT

The present disclosure relates to filamentous fungal host strains and recombinant DNA constructs for creation and use thereof. The filamentous fungal host strains are particularly useful for efficiently screening DNA libraries encoding recombinant proteins.

13 Claims, 10 Drawing Sheets

(56) References Cited

OTHER PUBLICATIONS

Penttila, M., et al. "A versatile transformation system for the cellulolytic filamentous fungus *Trichoderma reesei.*" *Gene* 61(2): 155-164, 1987.

Pourquie, J. et al., "Scale Up of Cellulase Production and Utilization." In *Biochemistry and Genetics of Cellulose Dedgradation*, Aubert, J.P. et al., eds., Academic Press, pp. 71-86, 1988.

Schell, D.J., et al., "Dilute-Sulfuric Acid Pretreatment of Corn Stover in Pilot-Scale Reactor." *J Appl. Biochem. Biotechnol.* 105: 69-86, 2003.

Seidl, V., et al., "Trichoderma reesei: genetic approaches to improving strain efficiency." Biofuels, vol. 1(2): 343-354, 2010.

Sheir-Neiss, G., et al., "Characterization of the secreted cellulases of *Trichoderma reesei* wild type and mutants during controlled fermentations." *Appl. Microbiol. Biotechnology* 20: 46-53, 1984.

Te'O, V., et al., "Codon optimization of xylanase gene *xynB* from the thermophilic bacterium *Dictyoglomus thermophilum* for expression in the filamentous fungus *Trichoderma reesei.*" *FEMS Microbiology Letters* 190: 13-19, 2000.

Van Den Hondel, C.A.M.J.J., et al. "Heterologous Gene Expression in Filamentous Fungi." In *More Gene Manipulations in Fungi*, pp. 396-428, Bennett, J. W. and Lasure, L. L. (eds.), Academic Press, 1991.

Van Hartingsveldt, W., et al., "Development of a homologous transformation system for *Aspergillus niger* based on the *pyrG* gene." *Mol. Gen. Genet.* 206: 71-75, 1986.

Ward, M., et al, "Use of *Aspergillus* overproducing mutants, cured for integrated plasmid, to overproduce heterologous proteins." *Appl. Microbiol. Biotechnol.* 39: 738-743, 1993.

Wood, T., "Preparation of Crystalline, Amorphous, and Dyed Cellulase Substrates." In *Methods in Enzymology*, vol. 160, pp. 19-25, Wood, W. & Kellog, S., (Eds.), Academic Press, San Diego, CA, 1988.

Xiong, H., et al, "Engineering the thermostability of *Trichoderma reesei* endo-1,4-$\beta$-xylanase II by combination of disulphide bridges." *Extremophiles* 8: 393-400, 2004.

Yelton, M.M., et al., "Transformation of *Aspergillus nidulans* by using a *trpC* plasmid." *Proc. Natl. Acad. Sci. USA* 81: 1470-1474, 1984.

Zou, J.-Y., et al. "Crystallographic evidence for substrate ring distortion and protein conformational changes during catalysis in cellobiohydrolase Cel6A from *Trichoderma reesei.*" *structure* 7(9): 1035-1045, 1999.

International Search Report and the Written Opinion of the International Searching Authority for International Application No. PCT/US2011/039092 dated Sep. 14, 2011.

International Preliminary Report on Patentability for International Application No. PCT/US2011/039092 dated Dec. 4, 2012.

\* cited by examiner

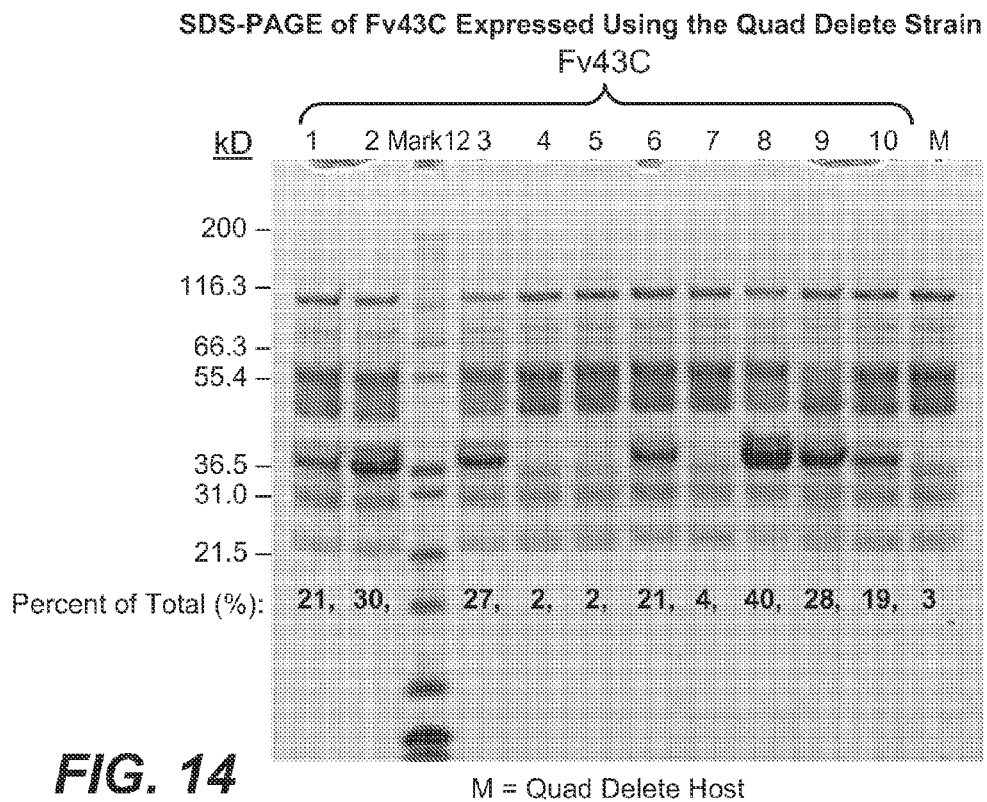
FIG. 14
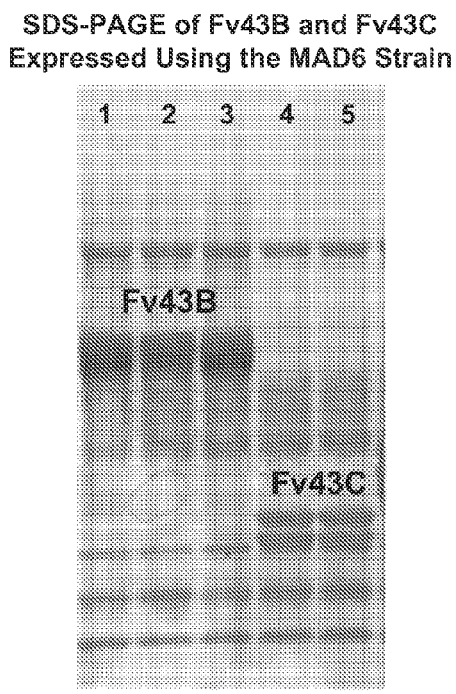
FIG. 15  Fv43B Percent of Total (%): 38, 36, 36
Fv43C Percent of Total (%): 26, 26

FILAMENTOUS FUNGAL HOST STRAINS AND DNA CONSTRUCTS, AND METHODS OF USE THEREOF

I. CROSS-REFERENCE TO RELATED APPLICATIONS

This application is the National Stage of International Application No. PCT/US2011/039092, filed Jun. 3, 2011, which claims priority to U.S. Provisional Application 61/351,286, filed Jun. 3, 2010, the disclosures of which are incorporated herein by reference.

II. SEQUENCE LISTING

The sequence listing submitted via EFS, in compliance with 37 C.F.R. §1.52(e), is incorporated herein by reference. The sequence listing text file submitted via EFS contains the file "NB31551-US-PCT_SequenceListing.txt" created on Oct. 13, 2014, which is 15 KB (118,559 bytes).

III. FIELD

The present disclosure relates to filamentous fungal host strains and recombinant DNA constructs for creation and use thereof. The filamentous fungal host strains are particularly useful for expressing proteins of interest in a reliable or less variable fashion, and for efficiently screening DNA libraries encoding recombinant proteins.

IV. BACKGROUND

Filamentous fungal host cell strains have been engineered to express various proteins. These proteins can then be used, optionally after being purified, in various industrial, academic or other applications. The expression process can often be unpredictable. It is not a rare occasion when only a very small number, if any, of the transformants prepared actually produce the enzyme of interest. Variability in expression of heterologous genes (e.g., non-native genes, or native genes existing in a form that is different from the native form) can occur as a consequence of factors unrelated to their nucleic acid and/or amino acid sequences. For instance, non-homologous integration predominates in filamentous fungi. Thus, expression vectors integrate into the genome at random, possibly resulting in positional effects on expression levels between transformants. In addition, unstable transformants may be generated, necessitating further screening of transformants to obtain stable transformants. Variability may also occur by generation of heterokaryons as a result of transformation of a multinucleate protoplast. Therefore, reliable means of producing enzymes of interest, with reduced variability, provide clear advantages.

For certain industrial applications, these proteins produced from fungal host strains are often engineered to obtain new, desirable characteristics, or a different level of certain characteristics. In these cases, existing filamentous fungal host cell strains are often used for screening DNA libraries encoding variant proteins. Variability in expression efficacy and/or levels makes it difficult to compare the characteristics of a given variant with those of another. Therefore, a particular advantage is clearly present if variants can be reliably expressed if they can be expressed by the particular host cell, and if variants can be expressed at less variable levels such that their characteristics can be more readily assessed and compared.

While telomeric, extrachromosomal replicating vectors can be used as an alternative to genomic integration, this method does not eliminate variability in expression levels between transformants. Thus, the art would benefit from tools to reduce sequence-independent differences in gene expression from filamentous fungal host strains.

V. SUMMARY

The present disclosure relates to filamentous fungal host strains and recombinant DNA constructs for creation and use thereof. The filamentous fungal host strains reliably produce transformants and express enzymes with reduced variability in expression levels. The filamentous fungal host strains are useful for efficiently screening DNA libraries encoding recombinant proteins.

In particular, the present disclosure provides filamentous fungal host cell expression systems, comprising: a) a fungal host cell containing in its chromosomal DNA a disruption in one or more components of the nonhomologous recombination (NHR) pathway, a part of a first selectable marker that lacks a first selectable function, and a second selectable marker that is operative to confer a second selectable function; and b) a nucleic acid molecule containing a sequence that, when introduced into the fungal host cell, confers the first selectable function to the first selectable marker, a sequence operable to express one or more genes of interest or variant genes of interest, and sequences with substantial homology to sequences that flank the chromosomal selectable markers; wherein the homologous sequences cause a homologous recombination event that results in a functional first selectable marker, removal of the second selectable marker, and expression of the genes of interest or the variant genes of interest. In some embodiments, the one or more components of the NHR pathway comprise one or more of the group consisting of ku80, ku70, rad50, mre11, xrs2, lig4, and xrs2. In certain embodiments, the nucleic acid molecule introduced into the fungal host cell in b) can be either a non-native or a native molecule existing in a non-native form to the fungal host cell.

Gene deletion may be accomplished by the use of a deletion plasmid. For example, the desired gene to be deleted or disrupted can be inserted into a plasmid. The deletion plasmid is then cut at an appropriate restriction enzyme site(s), internal to the desired gene coding region, and the gene coding sequence or part thereof replaced with a selectable marker. Flanking DNA sequences from the locus of the gene to be deleted or disrupted, preferably between about 0.5 and about 2.0 kb, remain on either side of the selectable marker gene. A suitable deletion plasmid will generally have unique restriction enzyme sites present therein to enable the fragment containing the deleted gene, including flanking DNA sequences, and the selectable marker gene to be removed as a single linear piece. A deletion plasmid may also be constructed by the use of PCR to amplify the desired flanking regions and selectable markers with restriction enzyme sites at the ends of the amplified fragments to facilitate the joining of fragments. Alternatively, a deletion plasmid can be synthesized de novo by specifying the appropriate flanking DNA and selectable marker sequences.

In some embodiments, the first and second selectable markers are different markers. In some embodiments, the first and second selectable markers are independently selected from the group consisting of alsR, amdS, hygR, pyr2, pyr4, pyrG, sucA, a bleomycin resistance marker, a blasticidin resistance marker, a pyrithiamine resistance marker, a chlorimuron ethyl resistance marker, a neomycin resistance marker, an adenine pathway gene, a tryptophan pathway gene, and thymidine kinase. In some embodiments, at least one of the homologous sequences is upstream or downstream from the pyr2 sequence. In some embodiments, the homologous sequences are upstream and downstream from the pyr2 sequences. In other embodiments, the homologous sequences comprise the sequence(s) operable to express one or more genes of interest or one or more variant genes of interest, and the sequence that confers the first selectable function to the first selectable marker. In some embodiments, the filamentous fungal host cell is a species of a genus selected from the group consisting of *Trichoderma, Penicillium, Aspergillus, Humicola, Chrysosporium, Fusarium*, and *Emericella*. In some embodiments, the *Trichoderma* is *T. reesei*, while in other embodiments, the *Aspergillus* is *A. niger*.

The present disclosure provides filamentous fungal host cell expression systems wherein the gene of interest or the variant gene of interest is selected from the group consisting of hemicellulases, peroxidases, proteases, cellulases, xylanases, lipases, phospholipases, esterases, cutinases, pectinases, keratinases, reductases, oxidases, phenol oxidases, lipoxygenases, ligninases, pullulanases, tannases, pentosanases, malanases, beta-glucanases, arabinosidases, hyaluronidase, chondroitinase, laccase, amylases, glucoamylases, and mixtures thereof. Non-limiting examples of genes of interest or variant genes encode: proteins or enzymes involved in starch metabolism, proteins or enzymes involved in glycogen metabolism, acetyl esterases, aminopeptidases, amylases, arabinases, arabinofuranosidases, carboxypeptidases, catalases, cellulases, chitinases, chymosin, cutinase, deoxyribonucleases, epimerases, esterases, α-galactosidases, β-galactosidases, α-glucanases, glucan lysases, endo-β-glucanases, glucoamylases, glucose oxidases, α-glucosidases, β-glucosidases, glucuronidases, hemicellulases, hexose oxidases, hydrolases, invertases, isomerases, laccases, lipases, lyases, mannosidases, oxidases, oxidoreductases, pectate lyases, pectin acetyl esterases, pectin depolymerases, pectin methyl esterases, pectinolytic enzymes, peroxi dases, phenoloxidases, phytases, polygalacturonases, proteases, rhamno-galacturonases, ribonucleases, thaumatin, transferases, transport proteins, transglutaminases, xylanases, hexose oxidase (D-hexose: O2-oxidoreductase, EC 1.1.3.5), variants thereof, and combinations thereof. In some embodiments, the gene of interest or the variant gene of interest encodes a polypeptide selected from the group consisting of peptide hormones, growth factors, clotting factors, chemokines, cytokines, lymphokines, antibodies, receptors, adhesion molecules, and microbial antigens (e.g., HBV surface antigen, HPV E7, etc.), and variants (e.g., fragments) thereof.

In addition the present disclosure provides methods of expressing a gene of interest or a variant gene of interest in the filamentous fungal host cell, comprising introducing into the filamentous fungal host cell the nucleic acid molecule that confers a first selectable function to a first selectable marker, which can be either a non-native or a native (but existing in a non-native form) molecule, growing the host cells, and selecting for host cells that have the first selectable function but lack the second selectable function. In some embodiments, expressions so achieved are more reliable than those achieved using conventional methods in the art. In some embodiments, the methods further comprise assaying for the expression of the gene of interest or the variant gene of interest, and/or for a biochemical function of a polypeptide encoded by the gene of interest or by the variant gene of interest.

All patents, patent applications, documents, nucleotide and protein sequence database accession numbers and articles cited herein are herein incorporated herein by reference in their entirety.

VI. BRIEF DESCRIPTION OF THE DRAWINGS

The following figures and tables are meant to be illustrative without limiting the scope and content of the instant disclosure or the claims herein.

FIG. 1 provides a schematic illustrating the derivation of the MAD6 host strain, from the quad-deleted derivative strain.

FIG. 2 provides a schematic of the *T. reesei* ku80 deletion cassette.

FIG. 3 provides a schematic of the pyr2 deletion cassette used to create the Archy2 strain.

FIG. 4 provides a schematic of the hygR deletion cassette used to create the Archy3 strain.

FIG. 5 provides a schematic of the *T. reesei* bgl1 deletion cassette.

FIG. 6 provides a schematic of the *T. reesei* egl3 deletion cassette.

FIG. 7 provides a schematic of the *T. reesei* telomeric plasmid vector used for expression of cre recombinase.

FIG. 14 is a picture of an SDS-PAGE characterizing Fv43C expressed using *T. reesei* quad deleted clones transformed with fv43C. The percent protein relative to the total proteins loaded was quantitatively determined in accordance with Example 2, and listed below the corresponding lane.

FIG. 15 is a picture of an SDS-PAGE characterizing Fv43B and Fv43C expressed using the MAD6 construct. The percent protein relative to the total proteins was quantitatively determined in accordance with Example 2, and listed below the corresponding lane.

VII. DETAILED DESCRIPTION OF VARIOUS EMBODIMENTS

Figure 1:
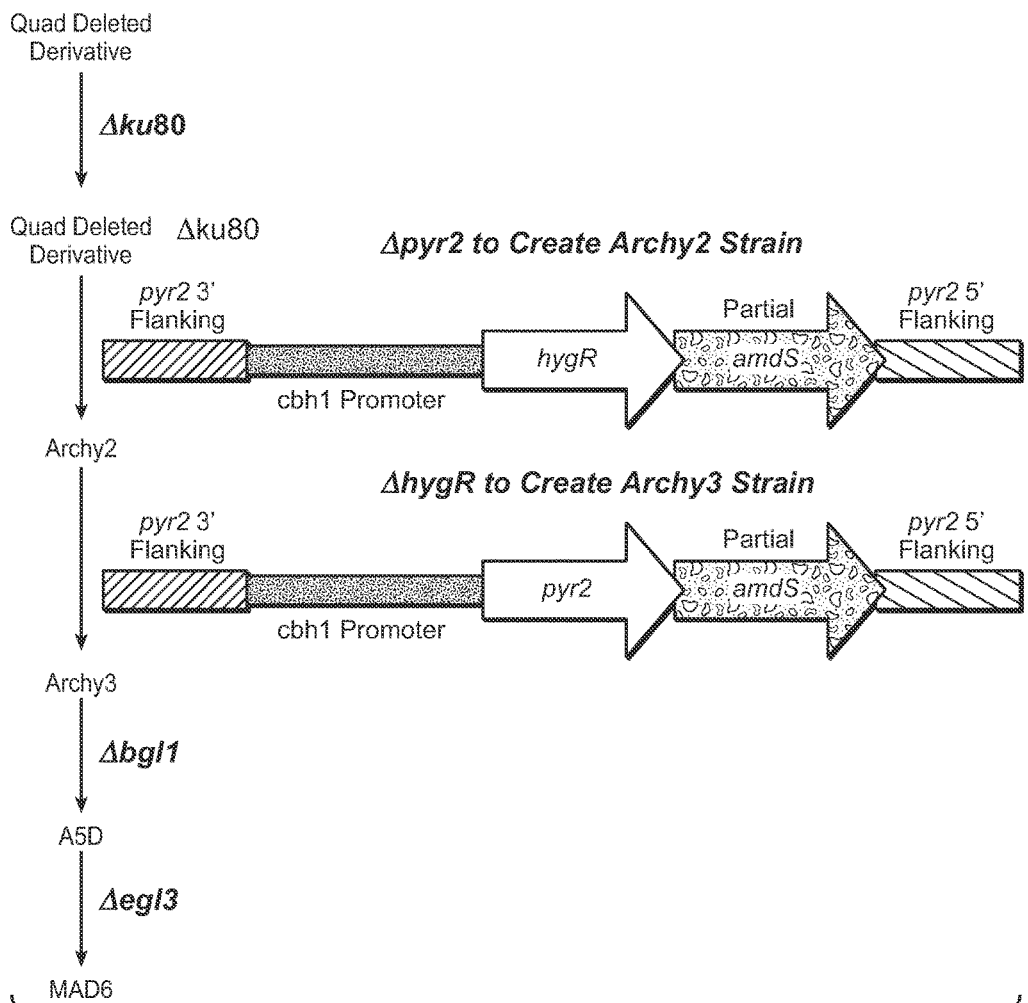

The present disclosure relates to filamentous fungal host strains and recombinant DNA constructs for creation and use thereof. The filamentous fungal host strains can be used to provide expression of genes or variants of interest in these hosts with higher reliability and/or lower variability in expression levels, as compared to other expression methods known in the art. The filamentous fungal host strains are, in a particular embodiment, useful for efficiently screening DNA libraries encoding recombinant proteins.

The methods described herein express proteins of interest or variants of interest with improved reliability. In this sense, the term "improved reliability" is reflected in that (1) at least 60% (e.g., at least 65%, at least 70%, at least 75%, at least 80%, at least 85%, at least 90%, at least 95%, or at least 99%) of the transformants are stable transformants; or that at least 60% (e.g., at least 65%, at least 70%, at least 75%, at least 80%, at least 85%, at least 90%, at least 95%, or at least 99%) of the transformants express the protein or variant of interest as intended over the background expression level; and (2) that the proteins or variants of interest are expressed with expression levels varying less than 60% (e.g., less than 55%, less than 50%, less than 45%, less than 40%, less than 35%, less than 30%, less than 25%, less than 20%, less than 15%, less than 10%, less than 5%, or less than 2%), wherein the term "expression level variation" is defined by dividing the difference between the highest and the lowest expression levels with a value that is the difference between the highest expression level and the background expression level, all determined with the same construct and the same gene or variant of interest.

It is to be understood that both the foregoing general description and the following detailed description are exemplary and explanatory only and are not restrictive of the compositions and methods described herein. In this application, the use of the singular includes the plural unless specifically stated otherwise. The use of "or" means "and/or" unless state otherwise. Likewise, the terms "comprise," "comprising," "comprises," "include," "including" and "includes" are not intended to be limiting. All patents and publications, including all amino acid and nucleotide sequences disclosed within such patents and publications, referred to herein are expressly incorporated by reference. The headings provided herein are not limitations of the various aspects or embodiments of the disclosure, which can be had by reference to the specification as a whole. Accordingly, the terms herein are more fully defined by reference to the specification as a whole.

Unless defined otherwise herein, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, NY (1991) provide one of skill with a general dictionary of many of the terms used in this disclosure. Although any methods and materials similar or equivalent to those described herein can be used in the practice or testing of the present disclosure, the preferred methods and materials are described. Numeric ranges are inclusive of the numbers defining the range. Unless otherwise indicated, nucleic acids are written left to right in 5' to 3' orientation; amino acid sequences are written left to right in amino to carboxyl orientation, respectively. Practitioners are particularly directed to Sambrook et al., MOLECULAR CLONING: A LABORATORY MANUAL (Second Edition), Cold Spring Harbor Press, Plainview, N.Y., 1989, and Ausubel F M et al., Current Protocols in Molecular Biology, John Wiley & Sons, New York, N.Y., 1993, for definitions and terms of the art. It is to be understood that this disclosure is not limited to the particular methodology, protocols, and reagents described, as these may vary.

1. DEFINITIONS

The terms below are more fully defined by reference to the specification as a whole.

The term "polypeptide" as used herein refers to a compound made up of a single chain of amino acid residues linked by peptide bonds. The term "protein" as used herein may be synonymous with the term "polypeptide".

"Variant" means a protein which is derived from a precursor protein (e.g., the native protein) by addition of one or more amino acids to either or both the C- and N-terminal end, substitution of one or more amino acids at one or a number of different sites in the amino acid sequence, or deletion of one or more amino acids at either or both ends of the protein, or at one or more sites in the amino acid sequence. The preparation of a variant of a protein of interest (e.g., encoded by a "gene of interest"), or a "variant of interest" (e.g., encoded by a "variant gene of interest"), can be performed by any means known in the art. For example, a variant of interest is prepared by modifying a DNA sequence which encodes for the native protein (e.g., the gene of interest), transformation of the modified DNA sequence into a suitable host, and expression of the modified DNA sequence to form the variant of interest. In a non-limiting example, a variant of a cellulase of interest may be performed by any means know in the art. For instance, a cellulase variant is prepared by modifying a DNA sequence which encodes for the its native (or naturally-occurring) counterpart, transformation of the modified DNA sequence into a suitable host, and expression of the modified DNA sequence to form the variant cellulase. The variant enzyme of interest of the disclosure includes polypeptides comprising altered amino acid sequences in comparison to that of the native enzyme of interest. The variant enzyme of interest, in certain embodiments, may retain some characteristics of the native enzyme of interest, but in the mean time, have certain altered characteristics from the native enzyme of interest. For example, variant cellulase of the disclosure includes peptides comprising altered amino acid sequences in comparison with a precursor enzyme amino acid sequence wherein the variant cellulase retains the characteristic cellulolytic nature of the precursor enzyme but which may have altered properties in some specific aspect. For example, a variant cellulase may have an increased pH optimum or increased temperature or oxidative stability or decreased affinity or binding to non-cellulosic materials but will retain its characteristic cellulolytic activity.

In a non-limiting example, it is contemplated that the variants of interest according to the present disclosure may be derived from a nucleotide sequence encoding a variant wherein the functional activity of the expressed variant is retained. For example, a cellulase variant may be derived from a DNA fragment encoding a cellulase variant wherein the cellulase activity of the expressed variant is retained. The DNA fragment encoding a cellulase may, in some embodiments, further include a DNA sequence or portion thereof encoding a hinge or linker attached to the cellulase DNA sequence at either the 5' or 3' end wherein the functional activity of the encoded cellulase domain is retained. The terms "variant" and "derivative" may be used interchangeably herein.

"Equivalent residues" may be defined by determining homology at the level of tertiary structure for a precursor or reference enzyme whose tertiary structure has been determined by x-ray crystallography. For example, equivalent residues are defined as those for which the atomic coordinates of two or more of the main chain atoms of a particular amino acid residue of a cellulase and *Hypocrea jecorina* CBH2 (N on N, CA on CA, C on C and O on O) are within 0.13 nm and preferably 0.1 nm after alignment. Alignment is achieved after the best model has been oriented and positioned to give the maximum overlap of atomic coordinates of non-hydrogen protein atoms of the enzyme and the precursor/reference enzyme in question. For example, a suitable model includes a crystallographic model giving the lowest R factor for experimental diffraction data at the highest resolution available. See, e.g., U.S. Patent Application Publication No. 2006/0205042.

Equivalent residues which are functionally analogous to a specific residue of a precursor or reference enzyme are defined as those residues that may adopt a conformation such that they alter, modify, or contribute to the structure of the enzyme, to the substrate binding, or to the catalysis in a predefined manner. For example, equivalent residues of *H. jecorina* CBH2 are those amino acids of a cellulase which may adopt a conformation such that they alter, modify or contribute to protein structure, substrate binding or catalysis in a manner defined. In some embodiments, equivalent residues can be those that occupy an analogous position to the extent that, although the main chain atoms of the given residue may not satisfy the criteria of equivalence on the basis of occupying a homologous position, the atomic coordinates of more than one (e.g., 2, 3, or more) of the side chain atoms of the residue lie within a short distance (e.g., within about 0.02 nm, within about 0.05 nm, within about 0.08 nm, within about 0.10 nm, within about 0.12 nm, within about 0.13 nm, within about 0.14 nm, within about 0.15 nm, within about 0.17 nm, within about 0.18 nm, within about 0.20 nm, within about 0 25 nm, etc) of the corresponding side chain atom of the precursor/reference enzyme. For example, a cellulase, for which a tertiary structure has been obtained by X-ray crystallography, may suitably comprise equivalent residues, wherein the atomic coordinates of at least two of the side chain atoms of the residue lie with 0.13 nm of the corresponding side chain atoms of *H. jecorina* CBH2, even though the main chain atoms of the given residue do not satisfy the criteria of equivalence on the basis of occupying a homologous position. The crystal structure of *H. jecorina* CBH2 is shown in Zou et al. (1999) Structure 7(9): 1035-45.

The term "nucleic acid molecule" includes RNA, DNA, and cDNA molecules. It will be understood that, as a result of the degeneracy of the genetic code, a multitude of nucleotide sequences encoding a given protein and/or variants thereof may be produced. The present disclosure contemplates every possible variant nucleotide sequence encoding the variant enzyme of interest, all of which are possible given the degeneracy of the genetic code. For example, a plurality of nucleotide sequence can encoding a cellulase, such as a CBH2 and/or variants thereof, which can be produced by a method or process described herein, because of the degeneracy of the genetic code.

A "heterologous" nucleic acid construct or sequence has a portion of the sequence which is not native or existing in a native form to the cell in which it is expressed. Heterologous, with respect to a control sequence refers to a control sequence (i.e. promoter or enhancer) that does not function in nature to regulate the same gene the expression of which it is currently regulating. Generally, heterologous nucleic acid sequences are not endogenous to the cell or part of the genome in which they are present, and have been added to the cell, by infection, transfection, transformation, microinjection, electroporation, or the like. A "heterologous" nucleic acid construct may contain a control sequence/DNA coding sequence combination that is the same as, or different from a control sequence/DNA coding sequence combination found in the native cell.

As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

Accordingly, an "expression cassette" or "expression vector" is a nucleic acid construct generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter.

As used herein, the term "plasmid" refers to a circular double-stranded (ds) DNA construct used as a cloning vector, and which forms an extrachromosomal self-replicating genetic element in many bacteria and some eukaryotes.

As used herein, the term "selectable marker-encoding nucleotide sequence" refers to a nucleotide sequence which is capable of expression in cells and where expression of the selectable marker confers to cells containing the expressed gene the ability to grow in the presence of a corresponding selective agent, or under corresponding selective growth conditions.

As used herein, the term "promoter" refers to a nucleic acid sequence that functions to direct transcription of a downstream gene. The promoter will generally be appropriate to the host cell in which the target gene is being expressed. The promoter, together with other transcriptional and translational regulatory nucleic acid sequences (also termed "control sequences"), are often used to express a given gene. In general, the transcriptional and translational regulatory sequences include, but are not limited to, promoter sequences, ribosomal binding sites, transcriptional start and stop sequences, translational start and stop sequences, and enhancer or activator sequences.

A "chimeric gene construct," as defined herein, refers to a non-native gene (i.e., one that has been introduced into a host or one that does not exist in its native form in the host) that may be composed of parts of different genes, including regulatory elements. A chimeric gene construct for transformation of a host cell is typically composed of a transcriptional regulatory region (promoter) operably linked to a protein coding sequence, or, in a selectable marker chimeric gene, to a selectable marker gene encoding a protein conferring, for example, antibiotic resistance to transformed cells. A typical chimeric gene of the present disclosure, for transformation into a host cell, includes a transcriptional regulatory region that is constitutive or inducible, a protein coding sequence, and a terminator sequence. A chimeric gene construct may also include a second DNA sequence encoding a signal peptide if secretion of the target protein is desired. For example, certain of the constructs described herein, e.g., the Archy 3 *T. reesei* strain, are chimeric gene constructs.

A nucleic acid is "operably linked" when it is placed into a functional relationship with another nucleic acid sequence. For example, the DNA encoding a secretory leader is operably linked to the DNA encoding a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors, linkers or primers for PCR are used in accordance with conventional practice.

A selection marker herein is said to be "operative" when it has full selection function.

As used herein, the term "gene" refers to the segment of DNA involved in producing a polypeptide chain, that may or may not include regions preceding and following the coding region, e.g. 5' untranslated (5' UTR) or "leader" sequences and 3' UTR or "trailer" sequences, as well as intervening sequences (introns) between individual coding segments (exons).

In general, nucleic acid molecules encoding a variant of interest will hybridize, under moderate to high stringency conditions to a wild type precursor/reference sequence. For example, a nucleic acid molecule encoding a variant cellulase such as CBH2 will hybridize, under moderate to high stringency conditions to the wild type sequence such as provided herein as SEQ ID NO:7. However, in certain embodiments, a nucleotide sequence encoding an enzyme of interest may reflect a substantially different codon usage, but continue to encode the same enzyme of interest. For example, the coding sequence may be modified to facilitate a more robust expression of the enzyme or variant of interest in a particular prokaryotic or eukaryotic expression system, in accordance with the frequency with which a particular codon is utilized by the host (see, e.g., Te'o et al., FEMS Microbiology Letters, 190: 13-19, 2000, describing the optimization of genes for expression in filamentous fungi).

A nucleic acid sequence is deemed "selectively hybridizable" to a reference nucleic acid sequence if the two sequences specifically hybridize to one another under moderate to high stringency hybridization and wash conditions. Hybridization conditions are based on the melting temperature (Tm) of the nucleic acid binding complex or probe. For example, "maximum stringency" typically occurs at about Tm −5° C. (5° C. below the Tm of the probe); "high stringency" at about 5- about 10° C. below the Tm; "moderate" or "intermediate stringency" at about 10- about 20° C. below the Tm of the probe; and "low stringency" at about 20- about 25° C. below the Tm. Functionally, maximum stringency conditions may be used to identify sequences having strict identity or near-strict identity with the hybridization probe; while high stringency conditions are used to identify sequences having about 80% or more sequence identity with the probe.

Moderate and high stringency hybridization conditions are well known in the art (see, e.g., Sambrook, et al, 1989, Chapters 9 and 11, and in Ausubel, F. M., et al., 1993, expressly incorporated by reference herein). An example of high stringency conditions includes hybridization at about 42° C. in 50% formamide, 5×SSC, 5×Denhardt's solution, 0.5% SDS and 100 µg/ml denatured carrier DNA followed by washing two times in 2×SSC and 0.5% SDS at room temperature and two additional times in 0.1×SSC and 0.5% SDS at 42° C.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

As used herein, the terms "transformed", "stably transformed" or "transgenic" with reference to a cell means the cell has a non-native (or not existing in its native form) nucleic acid sequence integrated into its genome or as an episomal plasmid that is maintained through multiple generations.

As used herein, the term "expression" refers to the process by which a polypeptide is produced based on the nucleic acid sequence of a gene. The process includes both transcription and translation.

The term "introduced" in the context of inserting a nucleic acid sequence into a cell, means "transfection", or "transformation" or "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

The term "expression of a protein or variant of interest" refers to transcription and translation of the gene of interest or the variant of interest, the products of which include precursor RNA, mRNA, polypeptide, post-translationally processed polypeptides, and derivatives thereof. For example, "CBH2 expression" refers to transcription and translation of the cbh2gene or variants thereof, the products of which include precursor RNA, mRNA, polypeptide, post-translationally processed polypeptides, and derivatives thereof, including CBH2 from related species such as *Trichoderma koningii, Hypocrea jecorina* (also known as *Trichoderma longibrachiatum, Trichoderma reesei* or *Trichoderma viride*) and *Hypocrea schweinitzii*. The level of expression can be determined by various known methods, including, for example, Western blot for the protein or variant of interest, Northern blot analysis and reverse transcriptase polymerase chain reaction (RT-PCR) assays for the mRNA of the gene or variant gene of interest, and enzymatic activity assays on suitable substrates. By way of example, assays for CBH2 expression include Western blot for CBH2 protein, Northern blot analysis and reverse transcriptase polymerase chain reaction (RT-PCR) assays for cbh2 mRNA, and Phosphoric Acid Swollen Cellulose (PASC) and p-hydroxybenzoic acid hydrazide (PAHBAH) assays as described in the following: (a) PASC: (Karlsson, J. et al. (2001), Eur. J. Biochem, 268, 6498-6507, Wood, T. (1988) in Methods in Enzymology, Vol.160. Biomass Part a Cellulose and Hemicellulose (Wood, W. & Kellog, S. Eds.), pp.19-25, Academic Press, San Diego, Calif., USA) and (b) PAHBAH: (Lever, M. (1972) Anal. Biochem., 47, 273, Blakeney, A. B. & Mutton, L. L. (1980) J. Sci. Food & Agriculture, 31, 889, Henry, R. J. (1984) J. of the Institute of Brewing, 90, 37).

The term "host cell" refers to a cell that contains a vector and supports the replication, and/or transcription or transcription and translation (expression) of the expression construct. Host cells for use in the present disclosure can be prokaryotic cells, such as an *E. coli* cell, or eukaryotic cells such as yeast, plant, insect, amphibian, or mammalian cells. In certain embodiments, host cells are suitably filamentous fungal cells.

The term "filamentous fungi" means any and all filamentous fungi recognized by those of skill in the art. A preferred fungus is selected from the group consisting of *Aspergillus, Trichoderma, Fusarium, Chrysosporium, Penicillium, Humicola, Neurospora*, or alternative sexual forms thereof such as *Emericella, Hypocrea*. It has now been demonstrated that the asexual industrial fungus *Trichoderma reesei* is a clonal derivative of the ascomycete *Hypocrea jecorina* (See, Kuhls et al., PNAS, 93:7755-7760, 1996).

Many microbes make enzymes that hydrolyze cellulose, including the wood rotting fungus *Trichoderma*, the compost bacteria *Thermomonospora, Bacillus*, and *Cellulomonas; Streptomyces*; and the fungi *Humicola, Aspergillus* and *Fusarium*.

The term "isolated" or "purified" as used herein refers to a nucleic acid or amino acid that is removed from at least one component with which it is naturally associated.

"Filamentous fungi" include all filamentous forms of the subdivision Eumycota and Oomycota. For example, filamentous fungi include, without limitation, *Acremonium, Aspergillus, Emericella, Fusarium, Humicola, Mucor, Myceliophthora, Neurospora, Scytalidium, Thielavia, Tolypocladium,* or *Trichoderma* species. In some embodiments, the filamentous fungus may be an *Aspergillus aculeatus, Aspergillus awamori, Aspergillus foetidus, Aspergillus japonicus, Aspergillus nidulans, Aspergillus niger,* or *Aspergillus oryzae*. In some embodiments, the filamentous fungus is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides,* or *Fusarium venenatum*. In some embodiments, the filamentous fungus is a *Humicola insolens, Humicola lanuginosa, Mucor miehei, Myceliophthora thermophila, Neurospora crassa, Scytalidium thermophilum,* or *Thielavia terrestris*. In some embodiments, filamentous fungus is a *Trichoderma harzianum, Trichoderma koningii, Trichoderma longibrachiatum, Trichoderma reesei*, e.g., RL-P37(Sheir-Neiss et al., Appl. Microbiol. Biotechnology, 20 (1984) pp. 46-53; Montenecourt B.S., Can., 1-20, 1987), QM9414 (ATCC No. 26921), NRRL 15709, ATCC 13631, 56764, 56466, 56767, or *Trichoderma viride*, e.g., ATCC 32098 and 32086. In some embodiments, the filamentous fungus is a *Trichoderma reesei* RutC30, which is available from the American Type Culture Collection as *Trichoderma reesei* ATCC 56765. Related to this, in some embodiments, the disclosure provides a whole cell broth preparation of any one of the filamentous fungi described herein.

Generally, the microorganism is cultivated in a cell culture medium suitable for production of enzymes. The cultivation takes place in a suitable nutrient medium comprising carbon and nitrogen sources and inorganic salts, using procedures known in the art. Suitable culture media, temperature ranges and other conditions suitable for growth and enzymatic production are known in the art. As a non-limiting example, the normal temperature range for the production of cellulases by *Trichoderma reesei* is 24° C. to 28° C.

Generally, a "whole cell broth preparation" is used as it is produced by fermentation with no or minimal recovery and/or purification. For example, once an enzyme or variant of interest (or more than one enzyme or variant of interest) is secreted by a cell into the cell culture medium, the cell culture medium containing the enzyme or variant of interest can be used. In some embodiments the whole cell broth preparation comprises the unfractionated contents of fermentation material, including cell culture medium, extracellular enzymes and cells. Alternatively, the whole cell broth preparation can be processed by any convenient method, e.g., by precipitation, centrifugation, affinity, filtration or any other method known in the art. In some embodiments, the whole cell broth preparation can be concentrated, for example, and then used without further purification. In some embodiments the whole cell broth preparation comprises chemical agents that decrease cell viability or kills the cells. In some embodiments, the cells are lysed or permeabilized using methods known in the art. For example, a cellulase or variant of interest (e.g., CBH2 or a variant thereof, Fv43B, Fv43A) can be secreted by a cell into the cell culture medium, the cell culture medium containing the cellulases or variants. The cell culture medium can be used as a whole cell broth preparation.

2. MOLECULAR BIOLOGY

In certain embodiments, the present disclosure provides for the expression of an enzyme or variant of interest. In certain embodiments, the gene encoding the enzyme or variant of interest is placed under the control of a promoter functional in a filamentous fungus. In an example of this embodiment, it is provided here a method of expressing variant cbh2 genes under the control of a suitable promoter functional in a filamentous fungus. Known techniques in the field of recombinant genetics can be applied (See, e.g., Sambrook et al., Molecular Cloning, A Laboratory Manual, 2nd ed., 1989; Kriegler, Gene Transfer and Expression: A Laboratory Manual, 1990; and Ausubel et al., eds., CURRENT PROTOCOLS IN MOLECULAR BIOLOGY, Greene Publishing and Wiley-Interscience, New York, 1994).

3. EXPRESSION OF RECOMBINANT PROTEINS

The methods of the disclosure pertain to host cells engineered to express recombinant proteins, without limiting the method of expression to any particular method. The recombinant protein or variant of interest is preferably secreted from the cells. The disclosure provides host cells, which have been transduced, transformed or transfected with an expression vector comprising a protein-encoding nucleic acid sequence. The culture conditions, such as temperature, pH and the like, are those previously used for the parental host cell prior to transduction, transformation or transfection and will be apparent to those skilled in the art.

In one approach, a filamentous fungal cell or yeast cell is transfected with an expression vector having a promoter or a biologically active promoter fragment, or one or more (e.g., a series) of enhancers, which function in the host cell line, operably linked to a DNA segment encoding a protein or variant of interest, such that the protein or variant of interest is expressed in the cell line.

A. Nucleic Acid Constructs/Expression Vectors

Natural or synthetic polynucleotide fragments encoding a protein or variant of interest may be incorporated into chimeric constructs or vectors, capable of being introduced into, and of replication in, a filamentous fungal or yeast cell. The vectors and methods disclosed herein are suitable for use in host cells for the expression of the protein or the variant. Any vector may be used as long as it is replicable and viable in the cells into which it is introduced. Large numbers of suitable vectors and promoters are known to those of skill in the art, and many are commercially available. Cloning and expression vectors are also described in Sambrook et al., 1989, Ausubel F M et al., 1989, and Strathern et al., The Molecular Biology of the Yeast Saccharomyces, 1981, each of which is expressly incorporated by reference herein. Suitable expression vectors for fungi are described in van den Hondel, C. A. M. J. J. et al. (1991) In: Bennett, J. W. and Lasure, L. L. (eds.) More Gene Manipulations in Fungi. Academic Press, pp. 396-428. The appropriate DNA sequence may be inserted into a plasmid or vector (collectively referred to herein as "vectors") by a variety of procedures. In some instances, the DNA sequence is inserted into suitable restriction endonuclease site(s) using known procedures. In other instances, methods of vector construction that do not involve restriction digestion and/or ligation may be suitably applied. Such procedures and related sub-cloning procedures are deemed to be within the scope of knowledge of those skilled in the art. Recombinant filamentous fungi comprising the coding seqence for a protein or variant of interest may be produced by introducing a chimeric construct comprising the coding region of the protein or variant of interest into the cells of a selected strain of the filamentous fungi.

Once the desired form of a nucleic acid sequence is obtained, it may be modified in a variety of ways. For example, where the sequence involves non-coding flanking regions, the flanking regions may be subjected to resection, mutagenesis, etc. Thus, transitions, transversions, deletions, and insertions may be performed on the naturally occurring sequence.

A selected coding sequence may be inserted into a suitable vector according to known recombinant techniques and used to transform filamentous fungi. Due to the inherent degeneracy of the genetic code, other nucleic acid sequences, which encode substantially the same or a functionally equivalent amino acid sequence may be used to clone and express the protein of interest or the variant. Therefore such substitutions in the coding region fall within the sequence variants covered by the present disclosure. Any and all of these sequence variants can be utilized in the same way as described herein, For example, sequence variants of a cellobiohydrolase, such as CBH2can be used when the protein or variant of interest is a cellulase.

The terms "cellulase" "cellulolytic enzymes" or "cellulase enzymes" refer to a category of enzymes capable of hydrolyzing cellulose polymers to shorter cello-oligosaccharide oligomers, cellobiose and/or glucose. Numerous examples of cellulases, such as exoglucanases, exocellobiohydrolases, endoglucanases, and glucosidases have been obtained from cellulolytic organisms, particularly including fungi, plants and bacteria. The enzymes made by these microbes are mixtures of proteins with three types of actions useful in the conversion of cellulose to glucose: endoglucanases (EG), cellobiohydrolases (CBH), and beta-glucosidase. These three different types of cellulase enzymes act synergistically to convert cellulose and its derivatives to glucose.

CBH2 from *Hypocrea jecorina* is a member of the Glycosyl Hydrolase Family 6 (hence Cel6) and, specifically, was the first member of that family identified in *Hypocrea jecorina* (hence Cel6A). The Glycosyl Hydrolase Family 6 contains both Endoglucanases and Cellobiohydrolases/exoglucanases, and CBH2 is a cellobiohydrolase/exoglucanase. Thus, the phrases CBH2, CBH2-type protein and Cel6 cellobiohydrolases are often used interchangeably herein. Thus, the term "variant cbh2 gene" means that the nucleic acid sequence of the cbh2 gene from *H. jecorina* has been altered by removing, adding, and/or manipulating the coding sequence.

The present disclosure also includes recombinant nucleic acid constructs comprising one or more protein-encoding nucleic acid sequences as described above. The constructs comprise a vector, such as a plasmid or viral vector, into which a sequence of the disclosure has been inserted, in a forward or reverse orientation.

Chimeric constructs may include the coding sequence for a protein or variant of interest. In some embodiments, the coding sequence can be present: (i) in isolation; (ii) in combination with additional coding sequences, such as, for example, fusion protein or signal peptide coding sequences, where the coding sequence is the dominant coding sequence; (iii) in combination with non-coding sequences, such as, for example, introns and control elements, which include, for example, promoter and terminator elements or 5' and/or 3' untranslated regions, effective for expression of the coding sequence in a suitable host; and/or (iv) in a vector or host environment in which the coding sequence is a native or a non-native gene.

In certain aspects, a chimeric construct is employed to transfer a protein-encoding nucleic acid sequence into a cell in vitro. Preferably, the cell into which the protein-encoding nucleic acid sequence is transferred is an established filamentous fungal or yeast line. For long-term, production of a protein or variant of interest, stable expression is preferred. Various known methods effective to generate stable transformants may be used to practice this disclosure.

Suitable vectors are typically equipped with a selectable marker-encoding nucleic acid sequence(s), insertion sites, and suitable control elements, such as promoter and termination sequences. The vector may comprise regulatory sequences, including, for example, non-coding sequences, such as introns and control elements, e.g., promoter and terminator elements or 5' and/or 3' untranslated regions, effective for expression of the coding sequence in host cells (and/or in a vector or host cell environment in which a modified soluble protein coding sequence is not normally expressed), operably linked to the coding sequence. Many suitable vectors and promoters are known to those of skill in the art, and many are commercially available and/or are described in Sambrook, et al. (supra).

Examples of suitable promoters include constitutive promoters and inducible promoters, including a CMV promoter, an SV40 early promoter, an RSV promoter, an EF-1αpromoter, a promoter containing the tet responsive element (TRE) in the tet-on or tet-off system as described (ClonTech and BASF), the beta actin promoter and the metallothionine promoter that can up regulated by addition of certain metal salts. A promoter sequence is a DNA sequence which is recognized by the particular filamentous fungus for expression purposes. It is operably linked to DNA sequence encoding a protein or variant of interest. Such linkage comprises positioning of the promoter with respect to the initiation codon of the DNA sequence encoding the protein of interest. The promoter sequence contains transcription or translation control sequences, which mediate the expression of the proteins or variants of interest. Non-limiting examples include promoters from *Aspergillus niger*,

*A. awamori* or *A. oryzae* glucoamylase-, alpha-amylase-, or alpha-glucosidase-encoding genes; the *A. nidulans* gpdA or trpC genes; the *Neurospora crassa* cbh1 or trp1 genes; the *A. niger* or *Rhizomucor miehei* aspartic proteinase encoding genes; the *H. jecorina* (*T. reesei*) cbh1, cbh2, egl1, egl2, or other cellulase encoding genes.

The choice of the proper selectable marker will depend on the host cell, and appropriate markers for different hosts are well known in the art. Examples of suitable selectable marker genes include argB from *A. nidulans* or *T. reesei*, amdS from *A. nidulans*, pyr4 from Neurospora crassa or *T. reesei*, pyrG from *Aspergillus niger* or *A. nidulans*. Additional examples of suitable selectable markers include, but are not limited to trpc, trp1, oliC31, niaD or leu2, which are included in chimeric constructs used to transform a mutant strain such as trp-, pyr-, leu-, and the like.

Such selectable markers confer to transformants the ability to utilize a metabolite that is usually not metabolized by filamentous fungi. For example, the amdS gene from *H. jecorina* which encodes the enzyme acetamidase, allows transformant cells to grow on acetamide as a nitrogen source. The selectable marker (e.g. pyrG) may restore the ability of an auxotrophic mutant strain to grow on a selective minimal medium or the selectable marker (e.g. olic31) may confer to transformants the ability to grow in the presence of an inhibitory drug or antibiotic.

The selectable marker coding sequence is cloned into any suitable plasmid using methods generally employed in the art. Examples of suitable plasmids include pUC18, pBR322, pRAX and pUC100. The pRAX plasmid contains AMAL sequences from *A. nidulans*, which make it possible to replicate in *A. niger*.

The practice of the present disclosure will employ, unless otherwise indicated, conventional techniques of molecular biology, microbiology, recombinant DNA, and immunology, which are within the skill of the art. Such techniques are explained fully in the literature. See, e.g., Sambrook et al., 1989; Freshney, Animal Cell Culture, 1987; Ausubel, et al., 1993; and Coligan et al., Current Protocols in Immunology, 1991.

B. Filamentous Fungi and Culture Conditions for Recombinant Protein Production

Examples of species of parental filamentous fungi that may be treated and/or modified for recombinant protein expression include, but are not limited to *Trichoderma*, e.g., *Trichoderma reesei*, *Trichoderma longibrachiatum*, *Trichoderma viride*, *Trichoderma koningii*; *Penicillium* sp., *Humicola* sp., including *Humicola insolens*, *Aspergillus* sp., *Chrysosporium* sp., *Fusarium* sp., *Hypocrea* sp., and *Emericella* sp.

Transformed cells are cultured under conditions typically employed to culture the parental fungal line. For example, cells can be cultured in a standard medium containing physiological salts and nutrients, such as described in Pourquie, J. et al., Biochemistry and Genetics of Cellulose Degradation, eds. Aubert, J. P. et al., Academic Press, pp. 71-86, 1988 and Ilmen, M. et al., Appl. Environ. Microbiol. 63:1298-1306, 1997. Various common cultural conditions can be suitable, e.g., cultures are incubated at 28° C. in shaker cultures or fermenters until desired levels of recombinant protein expression are achieved.

Suitable culture conditions for a given filamentous fungus may be found in the scientific literature and/or from the source of the fungi such as the American Type Culture Collection. After fungal growth has been established, the cells are exposed to conditions effective to cause or permit the expression of the recombinant protein.

In cases where a coding sequence is under the control of an inducible promoter, the inducing agent, e.g., a sugar, metal salt, or antibiotics, is added to the medium at a concentration effective to induce recombinant protein expression.

In some embodiments, the filamentous fungus is *Aspergillus niger*, which is a useful strain for obtaining overexpressed proteins of interest. For example *A. niger var awamori* dgr246 is known to secrete elevated amounts of cellulases (Goedegebuur et al., Curr. Genet (2002) 41: 89-98). Other strains of *Aspergillus niger var awamori* such as GCDAP3, GCDAP4 and GAP3-4 are also known. See, e.g., Ward et al, Appl. Microbiol. Biotechnol. 39:738-743.

In some embodiments, the filamentous fungus is *Trichoderma reesei*, which is another useful strain for obtaining overexpressed proteins of interest. In some embodiments, such a filamentous fungal host cell can have certain genes (or "detrimental genes" herein) that are linked to detrimental activities or traits (e.g., detrimental to expression, stability, confounding activities that would make queries or assays of certain properties difficult, etc) deleted or reduced. In some embodiments, such a fungal host cell can be modified such that it gains or enhances genes (or "favorable genes" herein) that are linked to certain favorable activities or traits, for example, increased secretion, increased stability, increased solubility, etc.

For example, a *Trichoderma reesei* strain RL-P37, described by Sheir-Neiss, et al., Appl. Microbiol. Biotechnol. 20:46-53 (1984) is known to secrete elevated amounts of cellulase enzymes. Functional equivalents of RL-P37 include *Trichoderma reesei* strain RUT-C30 (ATCC No. 56765) and strain QM9414 (ATCC No. 26921). It is contemplated that these strains would also be useful in over expressing proteins and variants thereof, including, without limitation, certain cellobiohydrolases such as CBH1 or CBH2, or certain endoglucanases.

By way of example, when the recombinant protein is a variant CBH2, it is preferable to produce the variant in the absence of potentially detrimental native cellulolytic activity. Thus, it is useful to obtain a *Trichoderma* host strain, which has had one or more cellulase genes deleted prior to introduction of a DNA construct or plasmid containing the DNA fragment encoding the variant CBH2. Suitable multiple-deletion strains as such may be prepared by the method disclosed in, for U.S. Pat. No. 5,246,853 and PCT publication WO 92/06209, which disclosures are hereby incorporated by reference. By expressing a variant CBH2 cellulase in a host microorganism that is missing one or more cellulase genes, the identification and subsequent purification procedures are simplified. Any gene from *Trichoderma* sp. which has been cloned can be deleted, for example, the cbh1, cbh2, egl1, and egl2 genes as well as those encoding EG III and/or EGV protein can be deleted from a *Trichoderma* host strain (see e.g., U.S. Pat. No. 5,475,101 and PCT publication WO 94/28117, respectively).

Gene deletions may be accomplished by inserting a form of the desired gene to be deleted or disrupted into a plasmid. The deletion plasmid can be then digested at an appropriate restriction enzyme site(s), internal to the desired gene coding region, and the gene coding sequence or a part thereof is replaced by a selectable marker. Flanking DNA sequences from the locus of the gene to be deleted or disrupted, preferably having a size of between about 0.5 to about 2.0 kb, can remain on either side of the selectable marker gene. A suitable deletion plasmid will generally have unique restriction enzyme sites present therein to enable the fragment containing the deleted gene, including flanking DNA sequences, and the selectable marker gene to be removed as a single linear piece.

In some embodiments, a selectable marker is chosen so as to enable detection of the transformed microorganism. Any selectable marker gene that is expressed in the selected microorganism may be suitable. For example, with *Aspergillus* sp., a selectable marker can be chosen so that the presence of the selectable marker in the transformants will not significantly alter the properties of the microorganism. Example of a suitable selectable marker is a gene that encodes an assayable product. For example, a functional copy of an *Aspergillus* sp. gene may be used, which, if lacking in the host strain, results in the host strain displaying an auxotrophic phenotype. Selectable markers also exist for *Trichoderma* sp.

In some embodiments, a pyrG⁻ derivative strain of *Aspergillus* sp. is transformed with a functional pyrG gene, which provides a selectable marker for transformation. The pyrG⁻ derivative strain may be obtained by selection of *Aspergillus* sp. strains that are resistant to fluoroorotic acid (FOA). The pyrG gene encodes orotidine-5'-monophosphate decarboxylase, an enzyme required for the biosynthesis of uridine. Strains with an intact pyrG gene grow in a medium lacking uridine but are sensitive to fluoroorotic acid. Accordingly FOA resistance selection can be used to select pyrG⁻ derivative strains that lack a functional orotidine monophosphate decarboxylase enzyme, and thus require uridine for growth. Using the FOA selection technique, it is also possible to obtain uridine-requiring strains, which lack a functional orotate pyrophosphoribosyl transferase. These cells can be transformed with a functional copy of the gene encoding this enzyme (Berges & Barreau, Curr. Genet. 19:359-365 (1991), and van Hartingsveldt et al., (1986) Mol. Gen. Genet. 206:71-75). The selection of derivative strains is performed using the FOA resistance technique described above. In some embodiments, the pyrG gene is employed as a selectable marker.

In some embodiments, a pyr4⁻ derivative strain of *Hypocrea* sp. (*Trichoderma* sp.) is transformed with a functional pyr4 gene, which provides a selectable marker for transformation. The pyr4⁻ derivative strain may be obtained by selection of *Hypocrea* sp. (*Trichoderma* sp.) strains that are resistant to fluoroorotic acid (FOA). The pyr4 gene encodes orotidine-5'-monophosphate decarboxylase, an enzyme required for the biosynthesis of uridine. Strains with an intact pyr4 gene grow in a medium lacking uridine but are sensitive to fluoroorotic acid. Accordingly, FOA resistance can be used to select pyr4⁻ derivative strains that lack a functional orotidine monophosphate decarboxylase enzyme, and thus require uridine for growth. Using the FOA selection technique it is also possible to obtain uridine-requiring strains, which lack a functional orotate pyrophosphoribosyl transferase. These cells can be transformed with a functional copy of the gene encoding this enzyme (Berges & Barreau, 1991). The selection of derivative strains is performed using the FOA resistance technique as described above. In some embodiments, the pyr4 gene is employed as a selectable marker.

A single DNA fragment comprising a disrupted or deleted detrimental gene, for example one exemplified above, is then isolated from the deletion plasmid and used to transform an appropriate pyrG⁻ *Aspergillus* or pyr4⁻ *Trichoderma* host. Transformants are identified and selected based on their ability to express the pyrG or pyr4 gene product, respectively, and thus compliment the uridine auxotrophy of the host strain. Southern blot analysis can be suitably carried out on the resultant transformants to identify and confirm a double crossover integration event, during which part or all of the coding regions of the genomic copy of the gene are deleted and replaced with the appropriate pyr selectable markers.

Although the specific plasmid vectors described above relate to preparation of pyr⁻ transformants, the present disclosure is not limited to these vectors. Various genes can be deleted and replaced in the *Aspergillus* sp. or *Hypocrea* sp. (*Trichoderma* sp.) strain using the above techniques described above. In addition, a number of selectable markers are suitable, as discussed herein. In fact, any gene that has been identified can suitably be deleted from the genome of any host, e.g., *Aspergillus* sp. or *Hypocrea* sp., using the above-described strategy.

In certain embodiments, the host strains used may be derivatives of *Hypocrea* sp. (*Trichoderma* sp.) that lack or have a nonfunctional gene or genes corresponding to the chosen selectable marker. For example, if the selectable marker of pyrG is chosen for *Aspergillus* sp., then a specific pyrG⁻ derivative strain is used as a recipient in the transformation procedure. In another example, if the selectable marker of pyr4 is chosen for a *Hypocrea* sp., then a specific pyr4 ⁻derivative strain is used as a recipient in the transformation procedure. In some embodiments, selectable markers comprising *Hypocrea* sp. (*Trichoderma* sp.) genes similar to the *Aspergillus nidulans* genes, including, for example, amdS, argB, trpC, or niaD may be used. The corresponding recipient strain is accordingly a derivative strain such as an amdS-, argB-, trpC-, or niaD- strain, respectively.

DNA encoding the protein or variant of interest can then be prepared for insertion into an appropriate microorganism. According to the present disclosure, DNA encoding a protein or variant of interest may comprise the DNA encoding a protein or variant that has an activity of the wild type protein. The DNA fragment encoding the protein or variant of interest may be functionally attached to a fungal promoter sequence, for example, the promoter of the glaA gene in *Aspergillus* or the promoter of the cbh1 or egl1 genes in *Trichoderma*.

The DNA encoding the protein of interest or the variant of interest may be prepared by constructing an expression vector carrying the DNA encoding the protein or the variant. The expression vector carrying the inserted DNA fragment encoding the protein or variant of interest can, for example, be any vector capable of replicating autonomously in a given host organism, or of integrating into the DNA of the host, typically in the form of a plasmid. In certain embodiments two types of expression vectors for obtaining expression of genes are contemplated. The first type contains DNA sequences wherein the promoter, gene-coding region, and terminator sequence all originate from the gene to be expressed. Gene truncation may be obtained where desired by deleting undesired DNA sequences (e.g., coding for unwanted domains), leaving the domain to be expressed under control of its own transcriptional and translational regulatory sequences. A selectable marker may also be contained as a part of the vector allowing the selection for integration into the host of multiple copies of the desired gene sequences.

The second type of expression vector is preassembled and contains sequences useful for high-level transcription and a selectable marker. It is contemplated that the coding region for a gene or a part thereof can be inserted into such a general-purpose expression vector, placing it under the transcriptional control of the expression cassettes promoter and terminator sequences. A non-limiting example of such a general-purpose expression vector is pRAX in *Aspergillus*. The gene or variant gene of interest, or a part thereof, can be inserted downstream of the strong glaa promoter. A non-limiting example of such a general-purpose expression vector is the pTEX in *Hypocrea*. The gene or variant gene of interest, or a part thereof, can be inserted downstream of the strong cbh1 promoter.

In certain embodiments, in the vector, the DNA sequence encoding the protein or variant of interest is operably linked to transcriptional and translational sequences, for example, a suitable promoter sequence and signal sequence, in reading frame to the structural gene. The promoter is suitably any DNA sequence that shows transcriptional activity in the particular host cell and may be derived from genes encoding proteins either homologous or heterologous to the host cell. An optional signal peptide may provide for extracellular production of the protein or variant of interest. The DNA encoding the signal sequence is preferably that which is naturally associated with the gene to be expressed. However signal sequences from any suitable sources, for example from an exo-cellobiohydrolase or from an endoglucanase of *Trichoderma*, are contemplated.

Protocols that can be used to ligate the DNA sequences coding for the protein or variant of interest to a promoter, and insertion of such a construct into suitable vectors are known in the art.

The DNA vector or construct described herein may be introduced into the host cell in accordance with known techniques such as transformation, transfection, microinjection, microporation, biolistic bombardment and the like.

For example, when a DNA vector or construct described herein is used to transform a fungal host cell, the permeability of the cell wall of *Hypocrea* sp. (*Trichoderma* sp.) to DNA can be low. Accordingly, uptake of the desired DNA sequence, gene or gene fragment is often minimal. A number of methods can be used to increase the permeability of the *Hypocrea* sp. (*Trichoderma* sp.) cell wall in the derivative strain (e.g., one lacking a functional gene corresponding to the used selectable marker) prior to the transformation process.

In certain embodiments, to prepare *Aspergillus* sp. or *Hypocrea* sp. (*Trichoderma* sp.) for transformation, protoplasts from fungal mycelium are prepared. See Campbell et al. Curr. Genet. 16:53-56; 1989. Mycelium can be obtained from germinated vegetative spores. The mycelium is treated with an enzyme that digests the cell wall, resulting in protoplasts. The protoplasts are then protected by the presence of an osmotic stabilizer in the suspending medium. Suitable stabilizers include, for example, sorbitol, mannitol, potassium chloride, magnesium sulfate and the like. Usually the concentration of the stabilizer(s) can vary between 0.8 M and 1.2 M (e.g., between 0.9M and 1.2 M, between 1,0M and 1.2 M, between 1.1 M and 1.2 M, etc). In a particular embodiment, 1.2 M of sorbitol is used as stabilizer in a suspension medium.

Uptake of the DNA into the host strain (e.g., *Aspergillus* sp. or *Hypocrea* sp. (*Trichoderma* sp.) can often be dependent upon the calcium ion concentration. Generally between about 10 mM $CaCl_2$ and about 50 mM $CaCl_2$ (e.g., between about 15 mM and about 45 mM, between about 20 mM and about 40 mM, between about 25 mM and about 35 mM) is used in an uptake solution. Aside from including calcium ion in the uptake solution, other items often included are a buffering system such as a TE buffer (10 mM Tris, pH 7.4; 1 mM EDTA) or a 10 mM MOPS, pH 6.0 buffer (morpholinepropanesulfonic acid) and polyethylene glycol (PEG). It is believed that the polyethylene glycol in this buffer acts to fuse the cell membranes thus permitting the contents of the medium to be delivered into the cytoplasm of the host strain (e.g., *Aspergillus* sp. or *Hypocrea* sp), and the plasmid DNA is transferred to the nucleus. In certain embodiments, this fusion process leaves multiple copies of the plasmid DNA integrated into the host chromosome.

Usually a suspension containing the *Aspergillus* sp. protoplasts or cells that have been subjected to a permeability treatment at a density of $10^5$ to $10^6$/mL, preferably $2\times10^5$/mL are used in transformation. Similarly, a suspension containing the *Hypocrea* sp. (*Trichoderma* sp.) protoplasts or cells that have been subjected to a permeability treatment at a density of $10^8$ to $10^9$/mL, preferably $2\times10^8$/mL are used in transformation. A volume of 100 µL of these protoplasts or cells in an appropriate solution (e.g., 1.2 M sorbitol; 50 mM $CaCl_2$) are mixed with the desired DNA. In some embodiments, a substantial amount of PEG is added to the uptake solution. For example, from about 0.1 to about 1 volume of 25% PEG 4000 can be added to the protoplast suspension. In a particular example, about 0.25 volume of 25% PEG 4000 is added to the protoplast suspension. Additives such as dimethyl sulfoxide, heparin, spermidine, potassium chloride and the like may also be added to the uptake solution and aid in transformation.

In certain embodiments, the mixture is incubated at about 0° C., for a period of about 10 to about 30 minutes. Additional PEG can be added to the mixture to further enhance the uptake of the desired gene or DNA sequence. In certain embodiments, the 25% PEG 4000 can be added in volumes that are 5 to 15 times that of the transformation mixture; however, greater and lesser volumes may also be suitable. For example, the 25% PEG 4000 is added at 10 times the volume of the transformation mixture in some embodiments. After the PEG is added, the transformation mixture is then incubated either at room temperature or on ice before the addition of a sorbitol and $CaCl_2$ solution. The protoplast suspension is then further added to molten aliquots of a growth medium. This growth medium permits the growth of transformants. Many growth media can be suitably used to grow the desired transformants in the present disclosure. In certain embodiments, for example, if Pyr⁺ transformants are being selected it is preferable to use a growth medium that contains no uridine. For example, the colonies are transferred and purified on a growth medium depleted of uridine.

At this stage, stable transformants may be distinguished from unstable transformants by their faster growth rate. Also, with a number of filamentous fungal hosts, such as, for example, *Trichoderma*, the formation of circular colonies with a smooth, as opposed to a ragged outline on solid culture medium lacking uridine can be used as a distinguishing feature. In some embodiments, further tests and selections of stability may be made by growing the transformants on solid non-selective medium (e.g., containing uridine), harvesting spores from this culture medium, and determining the percentage of these spores. The selected spores are allowed to germinate and grow on selective medium lacking uridine.

C. Introduction of a Recombinant Protein-Encoding Nucleic Acid Sequence into Host Cells The disclosure further provides cells and cell compositions which have been genetically modified to comprise a recombinant protein-encoding nucleic acid sequence. A parental cell or cell line may be genetically modified (i.e., transduced, transformed or transfected) with a cloning vector or an expression vector. The vector may be, for example, in the form of a plasmid, a viral particle, a phage, etc., as further described above.

The methods of transformation of the present disclosure may result in the stable integration of all or part of the transformation vector into the genome of the filamentous fungus. Transformation resulting in the maintenance of a self-replicating extra-chromosomal transformation vector is also contemplated.

Many standard transfection methods can be used to produce filamentous fungal, e.g., *Trichoderma reesei*, cell lines that express substantial quantities of the non-native or native protein. For example, there are a number of published methods for introducing DNA constructs into enzyme-producing strains of *Trichoderma* include Lorito et al., 1993, Curr. Genet. 24: 349-356; Goldman et al., 1990, Curr. Genet. 17:169-174; Penttila et al., 1987, Gene 6: 155-164; for introducing DNA constructs into enzyme-producing strains of *Aspergillus*, Yelton et al., 1984, Proc. Natl. Acad. Sci. USA 81: 1470-1474; for introducing DNA constructs into enzyme-producing strains of *Fusarium*, Bajar et al., 1991, Proc. Natl. Acad. Sci. USA 88: 8202-8212; and for introducing DNA constructs into enzyme-producing strains of *Streptomyces*, Hopwood et al., 1985, The John Innes Foundation, Norwich, UK, and for *Bacillus*, Brigidi et al., 1990, FEMS Microbiol. Lett. 55: 135-138).

Other methods for introducing a heterologous nucleic acid construct (expression vector) into filamentous fungi (e.g., *H. jecorina*) include, but are not limited to the use of a particle or gene gun, permeabilization of filamentous fungi cells walls prior to the transformation process (e.g., by use of high concentrations of alkali, e.g., 0.05 M to 0.4 M $CaCl_2$ or lithium acetate), protoplast fusion or Agrobacterium mediated transformation. An example of such a method for transformating filamentous fungi by treatment of protoplasts or spheroplasts with polyethylene glycol and $CaCl_2$ is described in Campbell, E. I. et al., Curr. Genet. 16:53-56, 1989, and Penttila, M. et al., Gene, 63:11-22, 1988.

Any of the known procedures for introducing foreign nucleotide sequences into host cells may be used. These include, for example, the use of calcium phosphate transfection, polybrene, protoplast fusion, electroporation, biolistics, liposomes, microinjection, plasma vectors, viral vectors and any of the other known methods for introducing cloned genomic DNA, cDNA, synthetic DNA or other foreign genetic material into a host cell (see, e.g., Sambrook et al., supra). Also useful is the Agrobacterium-mediated transfection method described in U.S. Pat. No. 6,255,115. It is important that the particular genetic engineering procedure used be capable of successfully introducing at least one gene into the host cell capable of expressing the non-native or endogenous (but in a non-native form) gene.

In some embodiments, chimeric constructs comprising a recombinant protein-encoding nucleic acid sequence can be transcribed in vitro, and the resulting RNA can be introduced into the host cell by known methods, e.g., injection.

The disclosure further includes novel and useful transformants of filamentous fungi such as *H. jecorina* and *A. niger* for use in producing fungal enzymes, variants thereof, and compositions comprising these molecules. The disclosure includes transformants of filamentous fungi especially fungi comprising certain recombinant protein coding sequence(s), or deletion of certain endogenous coding sequences.

Following introduction of a chimeric construct comprising the coding sequence for a protein of interest or a variant thereof, the genetically modified cells can be cultured in conventional nutrient media modified as appropriate for activating promoters, selecting transformants or amplifying expression of a recombinant protein-encoding nucleic acid sequence. The culture conditions, such as temperature, pH and the like, are those previously used for the host cell selected for expression, and will be apparent to those skilled in the art.

The progeny of cells into which such chimeric constructs have been introduced are generally considered to comprise the protein-encoding nucleic acid sequence found in the chimeric construct.

The disclosure further includes novel and useful transformants of filamentous fungi such as *H. jecorina* for use in producing fungal enzymes, variants thereof, or compositions comprising such molecules. For example, *Aspergillus niger* may also be used in producing the recombinant proteins and variants thereof. The disclosure includes transformants of filamentous fungi especially fungi comprising the coding sequence of a protein of interest or of a variant thereof, or deletion of certain endogenous protein coding sequence(s).

EXAMPLES

The present disclosure is described in further detail in the following examples, which are not in any way intended to limit the scope of the disclosure as claimed. The attached figures are meant to be considered as integral parts of the specification and description of the disclosure. The following examples are offered to illustrate, but not to limit the claimed disclosure.

In the experimental disclosure which follows, the following abbreviations apply: M (molar); mM (millimolar); μM (micromolar); nM (nanomolar); mol (moles); mmol (millimoles); μmol (micromoles); nmol (nanomoles); gm (grams); mg (milligrams); μg (micrograms); pg (picograms); L (liters); ml or mL (milliliters); μl or μL (microliters); cm (centimeters); mm (millimeters); μm (micrometers); nm (nanometers); U (units); V (volts); MW (molecular weight); sec (seconds); mm(s) (minute/minutes); h(s) or hr(s) (hour/hours); ° C. (degrees Centigrade); QS (quantity sufficient); ND (not done); NA (not applicable); rpm (revolutions per minute); $H_2O$ (water); $dH_2O$ (deionized water); HCl (hydrochloric acid); aa (amino acid); bp (base pair); kb (kilobase pair); kD (kilodaltons); cDNA (copy or complementary DNA); DNA (deoxyribonucleic acid); ssDNA (single stranded DNA); dsDNA (double stranded DNA); dNTP (deoxyribonucleotide triphosphate); RNA (ribonucleic acid); $MgCl_2$ (magnesium chloride); NaC1 (sodium chloride); w/v (weight to volume); v/v (volume to volume); g (gravity); OD (optical density); HPLC (high pressure liquid chromatography); PAGE (polyacrylamide gel electrophoresis); PCR (polymerase chain reaction); RT-PCR (reverse transcription PCR); and SEL (site evaluation library).

Example 1

Creation of *Trichoderma reesei* Expression Strains

Improved strains were created to increase the expression consistency of variants of interest, in this instance, CBH2 variants, such that the expression level is less variable across variants of the same amino acid sequences. In particular, *T. reesei* strains were developed in combination with a targeting vector to force integration of cbh2 variant genes (e.g., coding region in operable combination with a regulatory sequence). The new strains prepared during development of the present disclosure, combine several mutations that are advantageous for screening variant libraries. A schematic of the genetic engineering steps is shown in FIG. 1.

Deletion of ku80 from the *T. reesei* Quad Deleted Derivative Strain

The quad deleted derivative strain is described in PCT Publication WO 2005/001036. A single orthologue of MUS52, the *N. crassa* orthologue of the human KU80, was identified by TBLASTN search in the genome sequence of *H. jecorina* QM6a (*Trichoderma reesei*) and was consequently named *Treesei* ku80, protein id 58213, available at the U.S. Department of Energy Joint Genome Institute. The nucleotide sequence of the *T. reesei* ku80gene is provided as SEQ ID NO:13:

```
ATGGCGGACAAGGAAGCAACCGTCTTCATCATCGACCTCGGCGCGTCCAT
GGCAGCTGTCAATGGGGGTCGAGAAGAATCCGACCTTGATTGGAGCATGA
GCTACGTCTGGGACAAGATCAGCAACGTCGTGGCCTCGAATCGCAAGACG
CTGTGCGTTGGCGTCGTGGGGTTCAGAACCGACGAGACAAACCACACGCT
GAGCGAGGATGGGTACGAGAACATCTCCATATTGCAGCCCCTGGGGCCGA
TGAGCATGTCCAGCCTCAAGGCTCTTCAGCCCAAGGTGAAGCCGAGCAGG
ACGGTGGAAGGCGATGCCATCTCGGCGATTGTCATTGCCGTCGACATGAT
TGACAAGTACACGAAGAAGAACAAATGGAAGCGGCAGATTGTTCTCATTA
CCGACGGCCAAGGCGAGATTGATCCAGATGATATTGGCGACATTGCTAGA
AAGATGCGCGACTCGAATATTGAATTGACAGTCTTGTGAGTTGGCGAGAC
CGTTTGGCGGACGGTAATGGTGCTGACGGTGATGCAAGGGGCGTCGACTT
TGATGCTCCCGATTACGGCTTCAAAGAGGAGGACAAACCTTCAGTCAAGG
TACTCCATATGTTCACTTCTTTTCTTTTTCTTCTTTATTTTCTTTTCTTT
TGAAGCTTTCATTAACCTCTTCGTTAGAAGCAAAACGAAGAGACCCTAAA
AAAGCTCGTGGATGGCTGTGGCGACGACTCAAGGTTCGCCTCCATGGTCG
AGGCCATTGACGACTTGAATGAGCCACGAGCAAAGTCGGTCAAGCCTTAC
AAAACGTACGAAGGTCTCTTGACCTTGGGAGATCCGAAAAACGCTCCCGC
AGTGGTGGAAATCCGCGTCGAGAGATACTTCAAGACCCATCTAGCCAGGC
CACCTGCCGCCAGCACCGTGGTGGTCAAGGAGGAGCAAGCTGGGCCGTCT
CAGGCAGACGAGGACGAACAGATGGACGGAGCGGAACTTACAGCTGTGAG
GCAGGCCAGGACATACAAGGTCAATGATCCAGATGCCCCTGGCGGTAAGC
GTGACGTTGAGTTTGAGTCTCTGGCCAAAGGGTACGAGTACGGCAGGACG
GCAGTCCACATCAGCGAGTCTGATCAAAACGTCACCAAGCTCGCGACAGA
AAAGAGCTTCAAGATCATCGGCTTCGTCCAGAAAGAAAAGGTATTGGCTT
GGCTCTCAGCATTTGACCCGTTGCTCTTGGCTAACCCTTGTTTAGTATGA
AATGCTCCTTAATCTTGGCGAAACCTGCGTTACCGTTGCATCCAAGTACG
ATGAAAAGTCTGAGCTGGCTTTTAGCTCTCTGGTGTGGGCGCTCTCGGAG
CTCGACGCCTACGCCGTGGCCCGCCTAGTAACTAAGGACCAAAAGGACCC
CATGCTGGTGTTACTGATGCCGTATATGGAGCCTGATTATGTTTGTCTCT
ATGATGTGCCTCTGCCTTTCGCAGAGGACATCAGGACGTACCAGTTTCCT
CCCTTGGACAGAGTCGTTACCGTCAGTGGCCAAACGCTCACCAACCATCG
CCTATTGCCATCCGACGAGCTCAACCAAGCGATGAGCGACTACGTAGATG
CCATGGACATTTCAAGTTATGGTATCGATGAAGATGGGTGAGTATAGAAG
ATGATTGTTCAAATCTTTCACTTCTAAGCATTGCTTCTGATCTAGGCAAC
CGGCTGAATATGCCACCATCGATGAGTTATACAACCCTGCGATACATCGC
ATAGGCCATGCGATCAAACAACGAGCGATCCACCCAGAGAAACCCGTGCC
CGAGATCCCCCCAGTCTTGCTTAGATTCGCAGCACCCCCGACAGAACTCG
TCGAGACTGTGCAGCCTCATATCGATGCACTGATTCACGCTGCAGACGTG
AAGAAAGGTACTGATTCCATTACATATGCTTCTCTGCACACTGATGTTTG
ATTTGTGCTAACGCCCCCCTTAGTGCCGCCCAAGGCCAAGGGCAAGCGCC
AAAGAGAAACAGTTAAACCCATCTCGGGACTGGATGTGGATGCCCTTCTG
GGAGAAGAGCAGAAAGGTTCCATTAGTCCGGAGAATGCCATTCCGGACTT
CAAACGAGCCCTCAACTCGTCCGAAGAAGTCGAGCAGATTGCCGACGCCA
CAAAACAAATGGGGGCCATTGTGCGGTCTCTCATTACGGACAGCTTCGGG
GATAGCAAATATGCCCAGGCAATGGAAGGCATTGGTGCGATGCGTGAGGA
GCTGATCAACCTGGAAGAGCCTGGCCTGTACAACGACTTTGTGCGCGACT
TGAAGAAAGTTTGCTATCTGGAGCCTTGGGTGGTGACAGGCGAGATTTC
TGGTTCAAGATGAGGTGGGCGAAGCTGGGCCTGATTGACAAGAAACAGTC
GGAGGTGTCTTCGGTCACTCTTGAGGAGGCGGACGAGGTGAGTGGTGCAG
CATGCTGTCGGATTATACGGACGTTGTTTGCTAACTTGTGGGATAGTTTT
ACAAGTCGAGGTGAGGTATCTACGTTGACCAAGAATGGGACCATGTATAT
GAGCGGTGTAACAACAGAATCCTGTGCTTTGAGCATTGTATGA
```

Figure 2:
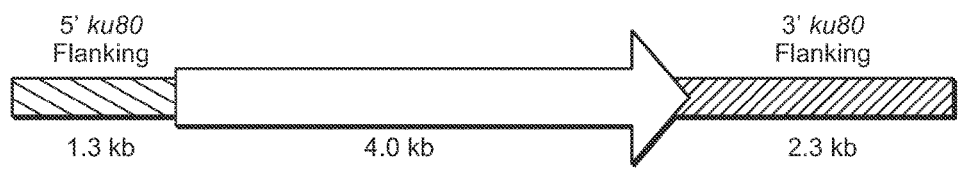

To delete the *T. reesei* ku80 gene from the quad deleted derivative strain, standard methods as generally described in, for example, PCT publication WO 2005/001036, were adapted for this purpose. Briefly, a ku80 deletion cassette was utilized that employed a selectable marker flanked between 1.3 kb of 5' ku80 sequence and 2.3 kb of 3' ku80 sequence, as schematically shown in FIG. 2. The variant *T. reesei* als, which confers resistance to the herbicide chlorimuron ethyl, was used as selectable marker. See, e.g., PCT Publication WO 2008/039370. The nucleotide sequence of the ku80 knockout cassette is 7685 base pairs in length: bases 1-1271 correspond to the 5' ku80 homologous region; bases 1280-7685 correspond to the als-chlorimuron ethyl resistant variant (A190D); and bases 5381-7685 correspond to the 3' ku80homologous region. The nucleotide sequence of the ku80 knockout cassette is provided as SEQ ID NO:1:

```
GGCCGCCTCAACACCCACACTCGAGGCACACGAGTTCATCGGCGGCTTCC
CCCACAAGCTCTCGGCCAACCTGCTACCGGCTCTCTCGCGAGACTTCCCA
AAGCCTACAAACGAGGTCGACGTCAAGGAGGCCCTCGAGCGCCAGCCCGG
CAGATGGAGCCTCCAGGGCCAGATCAAGGCCAACAACATGAGAGCCCAGA
GCGCCGCACTCCGGCTCGACGACAAGGAGGGCAAGGCGAGAGCCTTTGAG
GAGGCCAAGCGCGAGCTACTGGCGTATCACCACAGCGCCCTGCGGAAGCC
TTCCGGCGCAAGATAATGAGCTTGATCGCAATGACGAGTTCACGTACGCT
TTGCCATATTGTTGTTGCTTTTTGTTTGGTCCTACATGTACGGCGCATTG
GTTGGGAGGATATACCCACGGAGAGTGTCCGAGTGGCTTCTGGGATTTAG
```

-continued

AGCGTCATTAGCAGGATAGAGATGGTTGGCCAGGGGAATGGAATTGACTT
TTCACTACAAGGAACTTGTTCACTCTGGTGTTGATTCCCATTGCGTGACT
GGTAGTAGGGAGGAATGCTTTTACTTTGTGCCACTAGACCGCAGAGAAGG
GTTGGTTGCAAGCGGGGTCCGTGTATACCGACCAAGAGTGATGGGCATAC
AGCAACGTTTCTGAACGACTTCATTTTGTCCGAGTCTACTGGATGCGAGA
TGCCAGCGTGAAGCCGTACGCCACCAGGGCGACGAACTCGACAAGGTTGA
CGAGGGAGGAGATGCCGTGCAGCATGCCAAACTTCTTGTTGAGGGCACGC
ATCTCATCCGACTGTGCATCCTTGTCATACCACTCCTTTCCGTCTCGCTT
GGCTGGTGGGAGGGTTCAACAAATCCATCGTCAGCCATCCGGGGTCTCAA
ATCAATGGCGTGCATGCGGAGTCGGGCTTGAGGCTAACCTTGTCCATGGC
GGTCCTTCATGGTCTTGACAGTGGCGGGAAGCAGCACGGCGAGGTTGACG
AGGCCGCTGACGAACATGGTTGCGATGGGCACCAAGGAGCTCCACTTGTT
GGGAGCGTCGACGAGGCCGCCGATGCCGCCCTTGATGCCCAAGAGGGCGT
TTCCGGGGAACGTGAGGGCGAGCAGCGCGGGGATGGCCGTCTGCATGCCA
AAGTAGATGGGGAACAGCTTGCTCTGGATGGCGGAGAAGGAGGGCCGGCT
GACGGTGCGAACATGACGATGCCGTTGACGAAGGACTGCAGTAGCGTAG
TGTGATGGTAAGCAGCTGGCCGGCGCGCCTGAGACAATGGCCGGCAATGG
TAAAAAGGACCAAGATGTACTAGGTAGTTGCAATGTGGCTTATTACCTAC
CTACTACCTGGTAGGCACCTACTAGGTACTTGGGTAGACGGACAATGAAA
TTTGAAGTCGGGGTTGCAGGAAAGCAGGGCGCTGGACACATTGTGCTTCA
GGCGGTACCCGTCGTCATCGTCAGCCAATGTCGAGGCCCGGCAGCCCGAG
GAGCGAGACAACCTTGGCCGGAGGAGCCCGCAGGTACCTGCCAAAGCGCG
GCTGGTACCTCTCAACCCTCTCAGGCCTGTTGGATGCCCTATGACATGCC
CTGGGGGATGCAGCTGTTGCCCCGGCCCCGCACTTTCGGGTGACCGCGAG
GCTGCTGATTGGCTGGTTGCCACGGGCTGGGCGGTCCCTGAAGTTGTTGC
CATCTGAACTCTGTCGGCGCTGGCGTCGGCTGCGCCCAATGGGAGGCGAG
ACAACTCAGGGTACTAGAATCACTGACAGAAGAAGAGAATCGAAAGTAGG
TAGACAGCCAATTCGTTGCATGGCAGGCAACCGCACAGGAGAAAAATTGA
CTACCCCACAATCAGGCACAGTAAGTAGGGCACAGTACGTATGTACAGAC
AAGGCGCAAGCGATACTGCGCGACCCGGTACCTCGCCGGCTTGACACGTG
CGACAGGCTACTTTACTAGTATTCGCAGCGGCGGGTCGCGCATTATTACA
TGTACTGTGCCGCCATTTGATGACTGGGCTGCTGCAGTATTAGTAGATCT
GCCCGGCATCGCCCTTCCATGGGCGCGACCCGGGACTGGACCCTCTGACT
CTACCTACATGTACCTAGGCCGGGCCGGGCTTGGTGACTTTTGTCCGATC
AGGTCGTTCGCCTGGCTACCTATTATTTCTCTTTCTTCTTCTCCATCCTG
CTTCTGGCCTTGCAATTCTTCTTCGCCACTCCTCCCTCTTCCCCCCGCGA
TACCCTTGAATTCGTCAGAGAGGAAAAGACGAGAAAAAAAAGGGCAGCAG
AGACGTCGGTCTGGCTCACGTGCTGCATCTCTGCGCACTCTCATTTTTTT
TATTGTCCGACCCCTCCCTCAACCTTCTCCTTCGTTGACAGGCTAAGCCT
TGCTTCGACGCTCTCTCTTTGAATTTTTCTACTTCTACCTTCTTTTCTTG

CGTGTTACCCACCATAGCTCGATTCACGATGCTCCGAAGTCGCCAAGTCA
CAGCCAGGGCCGTCCGGGCTCTGGGCCAGGCGCGCGCCTTTACCTCGACG
ACCAAGCCTGTCATGATCCAGAGCAGCCAGAGGAAACAGGCCAACGCCAG
CGCTGCTCCGTAAGTCGCCCATTGCCATTGCATCTTCTGTTTGATATATA
CTTCCTGCTGCTTGCGTGGCGTCGTCTCTCGGTTATGCGTGTCAAGGACC
AGGTGTGTTCGCATCGTGGTTTTCCAGCGCCGATTACCGGGGGACGAATT
TTTGGCTGCTCAACTCGCGCGCGCGCATTCTGATTCTTCGTTTTCAATCT
TGAGCGACAACTGGCTAACATAATGGCCATTGGCAATTGCTTCACACAGA
CAAGTCCGCCCTGTACCGAGCCCTGCTTTCAACGCTGAAGACAAAGACCG
CAGCCATGTGCAGCCTCTGGTCAACCCGTCGAAGCCCGACATGGATGAAT
CGTATGTCCACGTCCCCTCGTCCCGCCCTACAAAATGAACACGATTACAC
CAGAATTTTTGCAACAATCGACACTTCTATAACAGACCAATTGAGCTTTG
TTCTGACCAATCATGTTGCTCTAGATTCATTGGCAAAACCGGAGGCGAAA
TCTTCCACGAGATGATGCTGCGACAGGGTGTCAAGCACATTTGTAGGTTC
CGATGCCGGCCGCCCACACGGGCTCCATCCTTGCTCCATCTCTCCAGCTA
GGCAAATCTCGCTAACCTTGAGTCACCATCCAGTCGGATACCCTGGCGGC
GCTATCCTGCCCGTCTTCGACGCCATCTACAACTCAAAACACTTCGACTT
CATCCTGCCCCGTCATGAGCAGGGAGCTGGCCATATGGCCGAGGGCTATG
CCCGTGCCTCGGGCAAACCCGGTGTCGTCCTGGTGACTTCCGGCCCCGGT
GCTACCAATGTCATCACGCCCATGCAGGATGCCCTGTCGGACGGAACGCC
CTTGGTCGTCTTCTGCGGCCAGGTCCCCACCACGGCCATCGGCAGCGATG
ACTTCCAAGAGGCCGACGTCGTGGGCATCTCGCGGGCCTGCACCAAGTGG
AACGTCATGGTCAAGAGCGTTGCTGAGCTGCCGGGAGAATCAACGAGGC
CTTTGAGATTGCCACCAGCGGCCGCCCTGGCCCCGTCCTCGTCGACCTGC
CCAAGGATGTCACGGCTGGTATCCTGAGGAGAGCCATCCCTACGGAGACT
GCTCTGCCGTCTCTGCCCAGTGCCGCCTCCCGCGCCGCCATGGAGCTGAG
CTCCAAGCAGCTCAACGCCTCCATCAAGCGTGCCGCCGACCTCATCAACA
TCGCCAAGAAGCCCGTCATCTACGCCGGTCAGGGTGTCATCCAGTCCGAG
GGCGGCGTTGAGCTCCTGAAGCAGCTGGCGGACAAGGCCTCCATCCCCGT
CACCACCACCCTCCATGGCCTGGGTGCCTTTGATGAGCTGGACGAGAAGT
CGCTGCACATGCTGGGCATGCACGGCTCGGCGTATGCCAACATGGCCATG
CAGCAGGCCGACCTCATCATCGCCCTCGGCAGCCGATTCGACGACCGTGT
TACTCTGAATGTCTCCAAATTTGCGCCTGCAGCCAGGCAAGCTGCTGCCG
AGGGCCGCGGCGGCATCATTCACTTTGAGATCATGCCCAAGAACATCAAC
AAGGTCATCCAGGCGACCGAGGCCGTCGAGGGCGACGTCGCCACCAACCT
GAAGCACCTCATTCCCCAGATTGCCGAAAAGTCCATGGCGGACCGAGGAG
AGTGGTTCGGCCTCATCAATGAGTGGAAGAAGAAGTGGCCCCTGTCAAAC
TACCAGCGCGCGGAGCGGGCTGGCCTCATCAAGCCGCAGACGGTCATGGA
GGAGATTAGCAACCTGACGGCCAACCGAAAGGACAAGACGTACATTGCCA
CGGGTGTCGGCCAGCACCAGATGTGGGTTGCCCAGCACTTCCGCTGGAGG
CACCCTCGATCCATGATTACCTCTGGTGGTCTGGGCACCATGGGCTACGG

-continued

```
TCTCCCCGCGGCCATTGGCGCCAAGGTGGCCCAGCCCGACGCTCTCGTAA
TTGACGTTGATGGCGATGCCTCGTTTAACATGACGCTGACGGAGCTGTCG
ACTGCTGCACAGTTCAACATTGGCGTCAAGGTGGTTGTGCTCAACAACGA
GGAGCAGGGCATGGTGACGCAGTGGCAGAACCTCTTTTACGAGGACCGAT
ATGCCCACACGCACCAGAAGAACCCCGACTTCATGAAGCTGGCCGACGCC
ATGGGCGTTCAGCACCAGCGCGTGACGGAGCCGGAGAAGCTGGTCGATGC
CCTGACGTGGCTGATCAACACCGATGGCCCGGCCCTGTTGGAGGTTGTCA
CGGACAAGAAGGTGCCTGTCCTGCCCATGGTGCCCGCCGGATCGGCCCTG
CACGAGTTCCTCGTCTTTGAACCTGGTGAGTCTACTTCAGACATATTGCT
TGCGCATTGCAGATACTAACACTCTCACAGAAAAGGATAAGCAGCGCCGT
GAGCTGATGAAGGAGAGAACAAAGGGTGTGCACTCCTAAAGCGATGATGT
CTGCGAGGGGTTCTTCGTTGAACCCTAGTTCAGGCACCATCTTACCCTCT
TATTTTTTCCCGTGGGCTTTCATTTTGTGTCATCCGAGCATGACGTTGTA
GGGTTGGAGTTTCTTCCTTTTTATCTTGTCATTTACTGGTACCCATAGGC
GCGAGACTAGGCTTCCATGTTTTGTTTTGCGACTTTCAAAAAGTACTTTT
AGTGGTTTGGGGCACGACGAGGGGGGGCAACCTCTTCTGTCGAAAAAGGT
GGCTGGATGGATGAGATGAGATGAGATGAGGGTGAAGATAGATACCTGCA
GTGTTTTTGACGCGACGGGATGGCGATCGCAGCACCCCCGACAGAACTCG
TCGAGACTGTGCAGCCTCATATCGATGCACTGATTCACGCTGCAGACGTG
AAGAAAGGTACTGATTCCATTACATATGCTTCTCTGCACACTGATGTTTG
ATTTGTGCTAACGCCCCCCTTAGTGCCGCCCAAGGCCAAGGGCAAGCGCC
AAAGAGAAACAGTTAAACCCATCTCGGGACTGGATGTGGATGCCCTTCTG
GGAGAAGAGCAGAAAGGTTCCATTAGTCCGGAGAATGCCATTCCGGACTT
CAAACGAGCCCTCAACTCGTCCGAAGAAGTCGAGCAGATTGCCGACGCCA
CAAAACAAATGGGGGCCATTGTGCGGTCTCTCATTACGGACAGCTTCGGG
GATAGCAAATATGCCCAGGCAATGGAAGGCATTGGTGCGATGCGTGAGGA
GCTGATCAACCTGGAAGAGCCTGGCCTGTACAACGACTTTGTGCGCGACT
TGAAGAAAAGTTTGCTATCTGGAGCCTTGGGTGGTGACAGGCGAGATTTC
TGGTTCAAGATGAGGTGGGCGAAGCTGGGCCTGATTGACAAGAAACAGTC
GGAGGTGTCTTCGGTCACTCTTGAGGAGGCGGACGAGGTGAGTGGTGCAG
CATGCTGTCGGATTATACGGACGTTGTTTGCTAACTTGTGGGATAGTTTT
ACAAGTCGAGGTGAGGTATCTACGTTGACCAAGAATGGGACCATGTATAT
GAGCGGTGTAACAACAGAATCCTGTGCTTTGAGCATTGTATGATATGATT
ATTGATGAACCGGACAAAAGGGGGTAGGGGATTGATGCCATCACGACCGA
TTGACCAGACCTGGATTCTCGCACAGCATGGCTGCTGATTTTGTTGACCT
TGCGACGTAACATCCCTGAAGAACAACCTACTATTAACCTATCATTTAGC
AGAAGCTCTGTAACCTTCTTGATTCTTGTATTCAGCTTCTGAGTCTGTCA
AATGTAATCATTTCGAGGTTGTGTAATTCCGGCCAAGCAGGCGGCCGTCT
GCCAGCGCCTGCCTAGGCTGCACCGCAATCTGCCCAATCAGCTGCCCTTC
AGTTTCGTTTGACCTTGCAGCTGCCCTTCATCCTTTATCTGCACACAATT
CTTTTTCCTCTGCTCTGCGCATTCTTCTCTCTCTCGTCTCCCTTCTCAAG
CTCAACTTCACCTCATCCGCTCCACTACAAGCCCTCCCGTCGTCGTCTCG
CATCCTCATCTCGACTGCGGCCAGCAAAACAAGCAAAGCCGTGATCGATC
CTCAGCATGGCTACCTTCAACCTCACCGTCCGCCTGGAGATGCTCAAAGA
AATTGGAATCACCGTCCAATACGGCGAGCATGTAGCGAAAGAAGCAGCCA
GCAACGAAGCAGCGATGGCATTCGAAGAAGAAGAAGAGTTCCCCGCCGTT
GTGCCGCCCAAGGCAGAACAGCACGCCTCTGAACACGACGCTGGCCACGA
TGCTTGGGACGCGGCTGCCCACATCTCGACTTCGGCGCAAGAACAGCAGA
AGCCCCAGGAGATGGACGACTCGTCTATCGTGATGCCGCTGGACTACTCC
AAGTTTGTCGTTGGAGAGCCTGCGGACGAATCCATCAGCTTTTGCTCGTG
GAAGGTCGTCGAGGCTTATCCTGACCAGTTTATCGGCAAGGCAAACAGGC
CTCGTGTATGTAGCGATTGCTTTCTCTGCATTATGGGAATCTCAAGAGAG
TATGGTAGAAGATAACTGACAACTTGCAGGCCAAGCCGTACTTTGACAAG
ATTTTGGAAGACAGAGTCTGGGATTTGTGAGGATCTTGATTGATGTGCAT
ATGGCGACATGCCTGCTAATATCATTGTAGCTTCTATCTCTACAACCCCG
AGAAGCCTTCAGAGAAGCCTCGCGTGCTGGTGCCCACTGTTCAGCTCGAA
GGCTTTCTCAAAAGCATCAACAGAGCGCTCGGTACTTCTCTCACCATTCC
AGGAGGGGCAAACCAGGACCGTTTTTATCTGAGGTTCGGCCAGGGAGACA
CCCCAAGGCCTCGATATCTACAGAGGTCGAGAGACCAGAAATCCCTAAAG
ATTGAAACGTTCCCCGATTTTCAACAGGCGGACTACGACAGCTTTAGGAA
CGCGCATGGCGCCATCCAGGAGGACTGGTTGAAGAACTGGCAGATGCTGG
TACCTCGGCCGAGTTTCGACAAGAAGAAAAATGCAGACAAAAGAGCAGCC
AAGAGAAGGCTCGAGCGAGAGCGAATGCTTCACAATACGCAGGAATTTCT
TCATTTGGCAGGTAAGGGCAAAGGGGCTGACGTGG.
```

Figure 3:
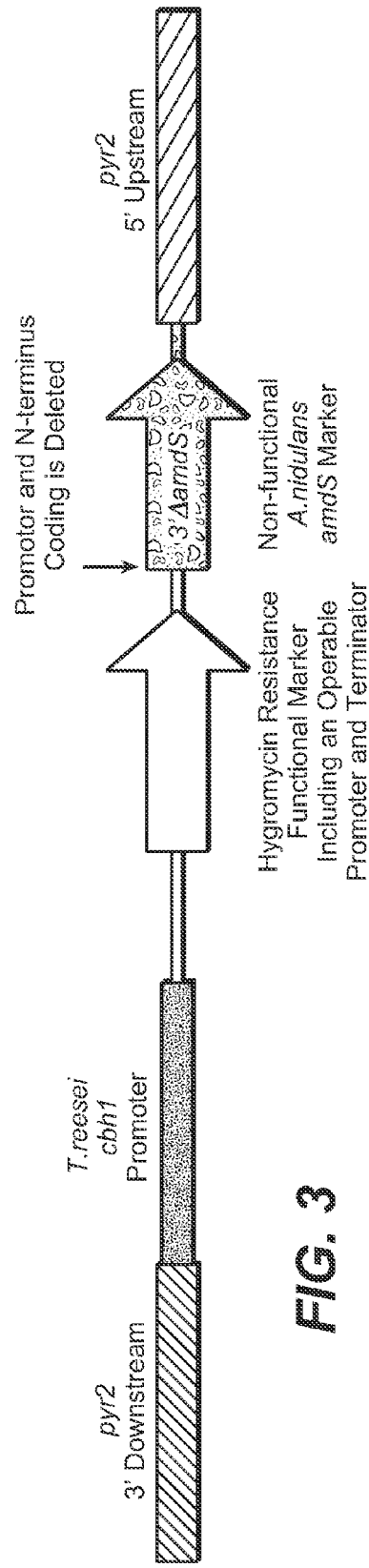

Creation of the Archy2 Strain from the *T. reesei* Δku80 Quad Deleted Derivative Strain First, the pyr2 gene was deleted from the ku80 knockout strain. The pyr2 deletion cassette contained the *T. reesei* cbh1 promoter, a hygromycin resistance gene and a partial amdS selectable marker flanked by 5' and 3' pyr2 sequences, schematically depicted in FIG. 3. This permitted screening for resistance to hygromycin and fluoroorotic acid among pyr2 knockout transformants. The partial amdS gene contained the 3' portion of the gene, but lacked a promoter and the amino-terminal portion of the coding region, and was consequently non-functional. The nucleotide sequence of the pyr2 knockout cassette is 9259 base pairs in length: bases 1-1994 correspond to the pyr2 3' homologous region; bases 2002-3497 correspond to the *T. reesei* cbh1 promoter; bases 3563-5449 correspond to the hygromycin resistance selectable marker; bases 5450-7440 correspond to the *A. nidulans* amdS 3' partial marker; and bases 7441-9259 correspond to the pyr2 5' homologous region. The nucleotide sequence of the pyr2 knockout cassette is provided as SEQ ID NO:2:

```
ATCACGCCCTCGCATAAAAGACCCTCAAGAGTCCATGTGCCCTATCTGCC
TGATCTTCCTAACCCTTATTTAACATTGGCCCTATCACAACCTAGTTCTT
CTTCAGCCTGCTTTGTCAACACTTGTCACGGTTCAACTCAACGTAATCAG
```

```
CAGGTAGCAGGACGAGGATAGGGAGAGAAACGAAGAGAAGAAGAGGAGAG
AGGAAGAAAAAAAAAGAAAAGAAAGAAAAAGGGAAAAGGAAAGAAGGAG
GAAAAGAGAAGAAAGTCAGATGAAGAAGCAAGAAGACGCCATGGTAGCCA
CCGCTTGTCAGGGCTCCTTAGCAACGAACAACTCTAGCTTGGGGACTTGT
CGATGTGTCGTTTCCTTCCTACCCATCAGCACCAACGATGAGTTCGATAT
AGACGAGGACCTCATGGAAGTAGAGACCATTGGGTTCGACAGGATCTCTC
AGTTTCACTTCTATGAGGTCTGTCGCTCGGATGACTTTTTGAGGAGCTTC
CCCTTCTGCTTCAACCCCAAACTCTCTTTCCTGAAACCGCAGCACGTTGG
CACGGCCGTGTTGCTGGAGCAGTTTGCTTTCGAGCACTCTCAGCGTGGTT
TCAGCAGCCCACTGGTGAGTGGCCTCCTTTGACGTCCACACCTTGCTCCT
GTCGCATGCGTATCTGGTGGGAACGACTGCTCCAAGGAGGATTGCTAACG
AGGTTGTAGGCCGAATATCGCATCAGATTCTCCGGTAACCTTAGCTACGG
CCTCTTCAACATCTGTGACATGACGGAGCGCAAGTACTGGTGGTTGGCGA
CCAAGATGCGCGGCTGGAACATCGACGGCTGCCCCGAAGACGTCAGGAGA
CTCATGTTTGTTCACATCATCGCCACCCTGGGATGCAGCCCCGTCGTGAC
GGATGAAGACATGGACTACCCCAAGAACTGGGCGGCAATTCTCCACGGTA
GAGACAGATATCCGAGTGAACCTGTGGGCCACCGGCCTCATGGGCGCACC
ATCTGCCTCCACTCGGTGGCCGTCTGCCCTCGTCTCCAGGGCTTGGGTCT
CGGTACTGCGACTCTGAAGTCGTATGTGCAGCGCATGAACAGCCTCGGCG
CCGCGGACCGTGTTGCTCTCGTTTGCCGCAAGCCCGAGACGAGATTTTTT
GAAAGATGCGGCTTCAGGAACAGCGGCCGGAGTAGTATCAAGACTCTGGT
CGGCGAATACTACAACATGGTGTGTGCTTCCACATCGACTTGGCCAGACT
CTATACGATTTTCAAACCTCGCTATACGTCATATTGACTTGTTTCTTTAG
GTCTTCGATTTGCCCGGGCCCAAAGACTTTATCGACTGGAATAGCATTGC
CGACGCTGCCAAGAAGATGTGAACCATTTGACTGATACGATGTGTGCTAC
GCATGTCGACCTTCTTTGTTTGTTTCTTTGGCGGCTCTTTGTATACCTTG
GGACACGGCAGACGCATGTCTATGTGAAGAAAACGTTCACGGCGCTGTTT
GCATCAGGAATATGATCATTAAACATGGAGCGTAATGGTATTAATGATCA
ACTAGAAAATGGTATGGAAGGGCGAGAGGGCGATCAACAAAGCAGCCCG
GGGCATAGTCTGGAAGCAGCAGGAATTGGAAGGGAAAAGGAAGCTGCACA
ATGAAGGGATATCGTGAGCGGAGTGGCTCACGAGAGTATCAACAGACTGG
CGAAAGCAAGCAATTGCCAACGCCGGCTATTAGGCCATAAGATGGCCTGT
TGTGAGTCCCAGTTGCACGTATCCCCATATGACTGCTCTGTCGCTGACTT
GAAAAAAATAGGGAGGATAAAGGAGAAAGAAAGTGAGACAACCCGTGAG
GGACTTGGGGTAGTAGGAGAACACATGGGCAACCGGGCAATACACGCGAT
GTGAGACGAGTTCAACGGCGAATGGAAAATCTTGAAAAACAAAATAAAAT
AACTGCCCTCCATACGGGTATCAAATTCAAGCAGTTGTACGGAGGCTAGC
TAGAGTTGTGAAGTCGGTAATCCCGCTGTATAGTAATACGAGTCGCATCT
AAATACTCCGAAGCTGCTGCGAACCCGGAGAATCGAGATGTGCTGGAAAG
CTTCTAGCGAGCGGCTAAATTAGCATGAAAGGCTATGAGAAATTCTGGAG
ACGGCTTGTTGAATCATGGCGTTCCATTCTTCGACAAGCAAAGCGTTCCG
TCGCAGTAGCAGGCACTCATTCCCGAAAAAACTCGGAGATTCCTAAGTAG
CGATGGAACCGGAATAATATAATAGGCAATACATTGAGTTGCCTCGACGG
TTGCAATGCAGGGGTACTGAGCTTGGACATAACTGTTCCGTACCCCACCT
CTTCTCAACCTTTGGCGTTTCCCTGATTCAGCGTACCCGTACAAGTCGTA
ATCACTATTAACCCAGACTGACCGGACGTGTTTTGCCCTTCATTTGGAGA
AATAATGTCATTGCGATGTGTAATTTGCCTGCTTGACCGACTGGGGCTGT
TCGAAGCCCGAATGTAGGATTGTTATCCGAACTCTGCTCGTAGAGGCATG
TTGTGAATCTGTGTCGGGCAGGACACGCCTCGAAGGTTCACGGCAAGGGA
AACCACCGATAGCAGTGTCTAGTAGCAACCTGTAAAGCCGCAATGCAGCA
TCACTGGAAAATACAAACCAATGGCTAAAAGTACATAAGTTAATGCCTAA
AGAAGTCATATACCAGCGGCTAATAATTGTACAATCAAGTGGCTAAACGT
ACCGTAATTTGCCAACGGCTTGTGGGGTTGCAGAAGCAACGGCAAAGCCC
CACTTCCCCACGTTTGTTTCTTCACTCAGTCCAATCTCAGCTGGTGATCC
CCCAATTGGGTCGCTTGTTTGTTCCGGTGAAGTGAAAGAAGACAGAGGTA
AGAATGTCTGACTCGGAGCGTTTTGCATACAACCAAGGGCAGTGATGGAA
GACAGTGAAATGTTGACATTCAAGGAGTATTTAGCCAGGGATGCTTGAGT
GTATCGTGTAAGGAGGTTTGTCTGCCGATACGACGAATACTGTATAGTCA
CTTCTGATGAAGTGGTCCATATTGAAATGTAAAGTCGGCACTGAACAGGC
AAAAGATTGAGTTGAAACTGCCTAAGATCTCGGGCCCTCGGGCCTTCGGC
CTTTGGGTGTACATGTTTGTGCTCCGGGCAAATGCAAAGTGTGGTAGGAT
CGAACACACTGCTGCCTTTACCAAGCAGCTGAGGGTATGTGATAGGCAAA
TGTTCAGGGGCCACTGCATGGTTTCGAATAGAAAGAGAAGCTTAGCCAAG
AACAATAGCCGATAAAGATAGCCTCATTAAACGGAATGAGCTAGTAGGCA
AAGTCAGCGAATGTGTATATATAAAGGTTCGAGGTCCGTGCCTCCCTCAT
GCTCTCCCCATCTACTCATCAACTCAGATCCTCCAGGAGACTTGTACACC
ATCTTTTGAGGCACAGAAACCCAATAGTCAACCGCGACTGCGCATCATG
TATCGGAAGTTGGCCGTCATCTCGGCCTTCTTGGCCACACCTCGTGCTAG
ACTAGGCGCGCCAGGAAGCCCGGAAGGTAAGTGGATTCTTCGCCGTGGCT
GGAGCAACCGGTGGATTCCAGCGTCTCCGACTTGGACTGAGCAATTCAGC
GTCACGGATTCACGATAGACAGCTCAGACCGCTCCACGGCTGGCGGCATT
ATTGGTTAACCCGGAAACTCAGTCTCCTTGGCCCCGTCCCGAAGGGACCC
GACTTACCAGGCTGGGAAAGCCAGGGATAGAATACACTGTACGGGCTTCG
TACGGGAGGTTCGGCGTAGGGTTGTTCCCAAGTTTTACACACCCCCAAG
ACAGCTAGCGCACGAAAGACGCGGAGGGTTTGGTGAAAAAGGGCGAAAA
TTAAGCGGGAGACGTATTTAGGTGCTAGGGCCGGTTTCCTCCCCATTTTT
CTTCGGTTCCCTTTCTCTCCTGGAAGACTTTCTCTCTCTCTCTTCTTCTC
TTCTTCCATCCTCAGTCCATCTTCCTTTCCCATCATCCATCTCCTCACCT
CCATCTCAACTCCATCACATCACAATCGATATGAAAAAGCCTGAACTCAC
CGCGACGTCTGTCGAGAAGTTTCTGATCGAAAAGTTCGACAGCGTCTCCG
ACCTGATGCAGCTCTCGGAGGGCGAAGAATCTCGTGCTTTCAGCTTCGAT
```

GTAGGAGGGCGTGGATATGTCCTGCGGGTAAATAGCTGCGCCGATGGTTT
CTACAAAGATCGTTATGTTTATCGGCACTTTGCATCGGCCGCGCTCCCGA
TTCCGGAAGTGCTTGACATTGGGGAATTCAGCGAGAGCCTGACCTATTGC
ATCTCCCGCCGTGCACAGGGTGTCACGTTGCAAGACCTGCCTGAAACCGA
ACTGCCCGCTGTTCTGCAGCCGGTCGCGGAGGCCATGGATGCGATCGCTG
CGGCCGATCTTAGCCAGACGAGCGGGTTCGGCCCATTCGGACCGCAAGGA
ATCGGTCAATACACTACATGGCGTGATTTCATATGCGCGATTGCTGATCC
CCATGTGTATCACTGGCAAACTGTGATGGACGACACCGTCAGTGCGTCCG
TCGCGCAGGCTCTCGATGAGCTGATGCTTTGGGCCGAGGACTGCCCCGAA
GTCCGGCACCTCGTGCACGCGGATTTCGGCTCCAACAATGTCCTGACGGA
CAATGGCCGCATAACAGCGGTCATTGACTGGAGCGAGGCGATGTTCGGGG
ATTCCCAATACGAGGTCGCCAACATCTTCTTCTGGAGGCCGTGGTTGGCT
TGTATGGAGCAGCAGACGCGCTACTTCGAGCGGAGGCATCCGGAGCTTGC
AGGATCGCCGCGGCTCCGGGCGTATATGCTCCGCATTGGTCTTGACCAAC
TCTATCAGAGCTTGGTTGACGGCAATTTCGATGATGCAGCTTGGGCGCAG
GGTCGATGCGACGCAATCGTCCGATCCGGAGCCGGGACTGTCGGGCGTAC
ACAAATCGCCCGCAGAAGCGCGGCCGTCTGGACCGATGGCTGTGTAGAAG
TACTCGCCGATAGTGGAAACCGACGCCCCAGCACTCGTCCGAGGGCAAAG
GAATAGAGTAGATGCCGACCGGGATCCACTTAACGTTACTGAAATCATCA
AACAGCTTGACGAATCTGGATATAAGATCGTTGGTGTCGATGTCAGCTCC
GGAGTTGAGACAAATGGTGTTCAGGATCTCGATAAGATACGTTCATTTGT
CCAAGCAGCAAAGAGTGCCTTCTAGTGATTTAATAGCTCCATGTCAACAA
GAATAAAACGCGTTTCGGGTTTACCTCTTCCAGATACAGCTCATCTGCAA
TGCATTAATGCATTGGACCTCGCAACCCTAGTACGCCCTTCAGGCTCCGG
CGAAGCAGAAGAATAGCTTAGCAGAGTCTATTTTCATTTTCGGGAGACTA
GCATTCTGTAAACGGGCAGCAATCGCCCAGCAGTTAGTAGGGTCCCCTCT
ACCTCTCAGGGAGATGTAACAACGCCACCTTATGGGACTATCAAGCTGAC
GCTGGCTTCTGTGCAGACAAACTGCGCCCACGAGTTCTTCCCTGACGCCG
CTCTCGCGCAGGCAAGGGAACTCGATGAATACTACGCAAAGCACAAGAGA
CCCGTTGGTCCACTCCATGGCCTCCCCATCTCTCTCAAAGACCAGCTTCG
AGTCAAGGTACACCGTTGCCCCTAAGTCGTTAGATGTCCCTTTTTGTCAG
CTAACATATGCCACCAGGGCTACGAAACATCAATGGGCTACATCTCATGG
CTAAACAAGTACGACGAAGGGGACTCGGTTCTGACAACCATGCTCCGCAA
AGCCGGTGCCGTCTTCTACGTCAAGACCTCTGTCCCGCAGACCCTGATGG
TCTGCGAGACAGTCAACAACATCATCGGGCGCACCGTCAACCCACGCAAC
AAGAACTGGTCGTGCGGCGGCAGTTCTGGTGGTGAGGGTGCGATCGTTGG
GATTCGTGGTGGCGTCATCGGTGTAGGAACGGATATCGGTGGCTCGATTC
GAGTGCCGGCCGCGTTCAACTTCCTGTACGGTCTAAGGCCGAGTCATGGG
CGGCTGCCGTATGCAAAGATGGCGAACAGCATGGAGGGTCAGGAGACGGT
GCACAGCGTTGTCGGGCCGATTACGCACTCTGTTGAGGGTGAGTCCTTCG

CCTCTTCCTTCTTTTCCTGCTCTATACCAGGCCTCCACTGTCCTCCTTTC
TTGCTTTTTATACTATATACGAGACCGGCAGTCACTGATGAAGTATGTTA
GACCTCCGCCTCTTCACCAAATCCGTCCTCGGTCAGGAGCCATGGAAATA
CGACTCCAAGGTCATCCCCATGCCCTGGCGCCAGTCCGAGTCGGACATTA
TTGCCTCCAAGATCAAGAACGGCGGGCTCAATATCGGCTACTACAACTTC
GACGGCAATGTCCTTCCACACCCTCCTATCCTGCGCGGCGTGGAAACCAC
CGTCGCCGCACTCGCCAAAGCCGGTCACACCGTGACCCCGTGGACGCCAT
ACAAGCACGATTTCGGCCACGATCTCATCTCCCATATCTACGCGGCTGAC
GGCAGCGCCGACGTAATGCGCGATATCAGTGCATCCGGCGAGCCGGCGAT
TCCAAATATCAAAGACCTACTGAACCCGAACATCAAAGCTGTTAACATGA
ACGAGCTCTGGGACACGCATCTCCAGAAGTGGAATTACCAGATGGAGTAC
CTTGAGAAATGGCGGGAGGCTGAAGAAAAGGCCGGGAAGGAACTGGACGC
CATCATCGCGCCGATTACGCCTACCGCTGCGGTACGGCATGACCAGTTCC
GGTACTATGGGTATGCCTCTGTGATCAACCTGCTGGATTTCACGAGCGTG
GTTGTTCCGGTTACCTTTGCGGATAAGAACATCGATAAGAAGAATGAGAG
TTTCAAGGCGGTTAGTGAGCTTGATGCCCTCGTGCAGGAAGAGTATGATC
CGGAGGCGTACCATGGGCACCGGTTGCAGTGCAGGTTATCGGACGGAGA
CTCAGTGAAGAGGACGTTGGCGATTGCAGAGGAAGTGGGGAAGTTGCT
GGGAAATGTGGTGACTCCATAGCTAATAAGTGTCAGATAGCAATTTGCAC
AAGAAATCAATACCAGCAACTGTAAATAAGCGCTGAAGTGACCATGCCAT
GCTACGAAAGAGCAGAAAAAAACCTGCCGTAGAACCGAAGAGATATGACA
CGCTTCCATCTCTCAAAGGAAGAATCCCTTCAGGGTTGCGTTTCCAGTAG
TGATTTACCGCTGATGAAATGACTGGACTCCTCCTCCTGCTCTTATAC
GAAAAATTGCCTGACTCTGCAAAGGTTGTTTGTCTTGGAAGATGATGTGC
CCCCCCATCGCTCTTATCTCATACCCCGCCATCTTTCTAGATTCTCATCT
TCAACAAGAGGGGCAATCCATGATCTGCGATCCAGATGTGCTTCTGGCCT
CATACTCTGCCTTCAGGTTGATGTTCACTTAATTGGTGACGAATTCAGCT
GATTTGCTGCAGTATGCTTTGTGTTGGTTCTTTCCAGGCTTGTGCCAGCC
ATGAGCGCTTTGAGAGCATGTGTCACTTATAAACTCGAGTAACGGCCAC
ATATTGTTCACTACTTGAATCACATACCTAATTTTGATAGAATTGACATG
TTTAAAGAGCTGAGGTAGCTTTAATGCCTCTGAAGTATTGTGACACAGCT
TCTCACAGAGTGAGAATGAAAAGTTGGACTCCCCCTAATGAAGTAAAAGT
TTCGTCTCTGAACGGTGAAGAGCATAGATCCGGCATCAACTACCTGGCTA
GACTACGACGTCAATTCTGCGGCCTTTTGACCTTTATATATGTCCATTAA
TGCAATAGATTCTTTTTTTTTTTTTTTTTTTTTTTTTTTTTTTTTTTTT
TTTGCCCAATTTCGCAGATCAAAGTGGACGTTATAGCATCATAACTAAGC
TCAGTTGCTGAGGGAAGCCGTCTACTACCTTAGCCCATCCATCCAGCTCC
ATACCTTGATACTTTAGACGTGAAGCAATTCACACTGTACGTCTCGCAGC
TCTCCTTCCCGCTCTTGCTTCCCCACTGGGGTCCATGGTGCGTGTATCGT
CCCCTCCACAATTCTATGCCATGGTACCTCCAGCTTATCAATGCCCCGCT
AACAAGTCGCCTCTTTGCCTTGATAGCTTATCGATAAAACTTTTTTTCCG

CCAGAAAGGCTCCGCCCACAGACAAGAAAAAAAATTCACCGCCTAGCCTT

TGGCCCCGGCATTTGGCTAAACCTCGAGCCTCTCTCCCGTCTTGGGGTAT

CAGGAAGAAAAGAAAAAAATCCATCGCCAAGGGCTGTTTTGGCATCACCA

CCCGAAAACAGCACTTCCTCGATCAAAAGTTGCCCGCCATGAAGACCACG

TGGAAGGACATCCCTCCGGTGCCTACGCACCAGGAGTTTCTGGACATTGT

GCTGAGCAGGACCCAGCGCAAACTGCCCACTCAGATCCGTGCCGGCTTCA

AGATTAGCAGAATTCGAGGTACGTCGCATTGCCCATCGCAGGATGTCTCA

TTATCGGGGTCCTTGGAGAACGATCATGATTGCATGGCGATGCTAACACA

TAGACAGCCTTCTACACTCGAAAGGTCAAGTTCACCCAGGAGACGTTTTC

CGAAAAGTTCGCCTCCATCCTCGACAGCTTCCCTCGCCTCCAGGACATCC

ACCCCTTCCACAAGGACCTTCTCAACACCCTCTACGATGCCGACCACTTC

AAGATTGCCCTTGGCCAGATGTCCACTGCCAAGCACCTGGTCGAGACCAT

CTCGCGCGACTACGTCCGTCTCTTGAAATACGCCCAGTCGCTCTACCAGT

GCAAGCAGCTCAAGCGGGCCGCTCTCGGTCGCATGGCCACGCTGGTCAAG

CGCCTCAAGGACCCCCTGCTGTACCTGGACCAGGTCCGCCAGCATCTCGG

CCGTCTTCCCTCCATCGACCCCAACACCAGGACCCTGCTCATCTGCGGTT

ACCCCAATGTTGGCAAGTCCAGCTTCCTGCGAAGTATCACCCGCGCCGAT

GTGGACGTCCAGCCCTATGCTTTCACCACCAAGAGTCTGTTTGTCGGCCA

CTTTGACTACAAGTACCTGCGATTCCAGGCCATTGATACCCCGGTATTC

TGGACCACCCTCTTGAGGAGATGAACACTATCGAAATGCAGAGGTATGTG

GCGCGGCTA

Creation of the Archy3 Strain from the Archy2 *T. reesei* Strain

Figure 4:
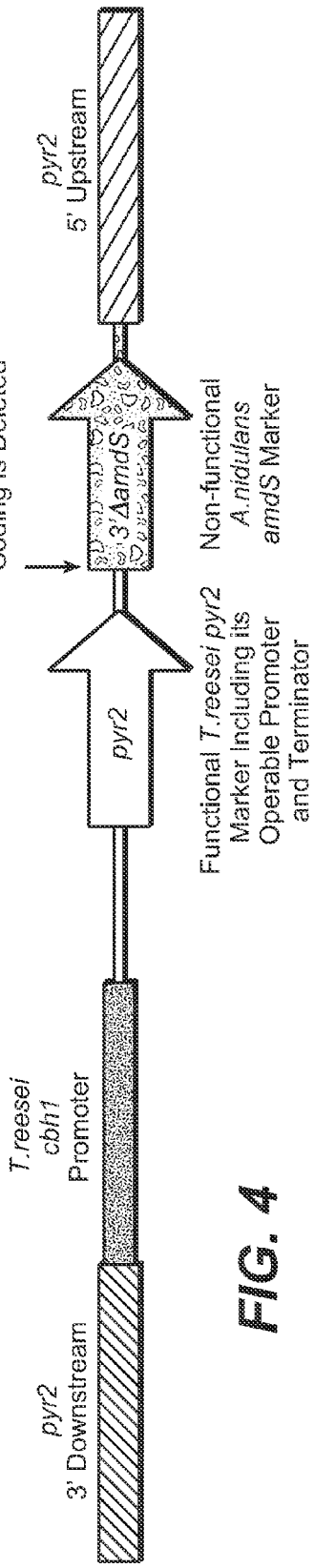

The Archy 2 strain was transformed with the hygromycin deletion cassette to integrate at the same pyr2 locus and replace the hygromycin resistance gene with the coding region of the pyr2 gene. The hygromycin deletion cassette is depicted in FIG. 4. This re-introduction of the pyr2 gene back into the pyr2 locus placed the pyr2 gene between the *T. reesei* cbh1 promoter and the partial amdS selectable marker. This strain was selected by uridine prototrophy and sensitivity to hygromycin. The nucleotide sequence of the hygR knockout cassette is 9088 base pairs in length: bases 1-1994 correspond to the pyr2 3' homologous region; bases 1995-3497 correspond to the *T. reesei* cbh1 promoter; bases 3564-5137 correspond to the pyr2 selectable marker; bases 5280-7270 correspond to the *A. nidulans* amdS 3' partial marker; bases 7271-9088 correspond to the pyr2 5' homologous region. The nucleotide sequence of the hygR knockout cassette is provided as SEQ ID NO:3:

ATCACGCCCTCGCATAAAAGACCCTCAAGAGTCCATGTGCCCTATCTGCC

TGATCTTCCTAACCCTTATTTAACATTGGCCCTATCACAACCTAGTTCTT

CTTCAGCCTGCTTTGTCAACACTTGTCACGGTTCAACTCAACGTAATCAG

CAGGTAGCAGGACGAGGATAGGGAGAGAAACGAAGAGAAGAAGAGGAGAG

AGGAAGAAAAAAAAGAAAAGAAAGAAAAAGGGAAAAGGAAAGAAGGAG

GAAAAGAGAAGAAAGTCAGATGAAGAAGCAAGAAGACGCCATGGTAGCCA

CCGCTTGTCAGGGCTCCTTAGCAACGAACAACTCTAGCTTGGGGACTTGT

CGATGTGTCGTTTCCTTCCTACCCATCAGCACCAACGATGAGTTCGATAT

AGACGAGGACCTCATGGAAGTAGAGACCATTGGGTTCGACAGGATCTCTC

AGTTTCACTTCTATGAGGTCTGTCGCTCGGATGACTTTTTGAGGAGCTTC

CCCTTCTGCTTCAACCCCAAACTCTCTTTCCTGAAACCGCAGCACGTTGG

CACGGCCGTGTTGCTGGAGCAGTTTGCTTTCGAGCACTCTCAGCGTGGTT

TCAGCAGCCCACTGGTGAGTGGCCTCCTTTGACGTCCACACCTTGCTCCT

GTCGCATGCGTATCTGGTGGGAACGACTGCTCCAAGGAGGATTGCTAACG

AGGTTGTAGGCCGAATATCGCATCAGATTCTCCGGTAACCTTAGCTACGG

CCTCTTCAACATCTGTGACATGACGGAGCGCAAGTACTGGTGGTTGGCGA

CCAAGATGCGCGGCTGGAACATCGACGGCTGCCCCGAAGACGTCAGGAGA

CTCATGTTTGTTCACATCATCGCCACCCTGGGATGCAGCCCCGTCGTGAC

GGATGAAGACATGGACTACCCCAAGAACTGGGCGGCAATTCTCCACGGTA

GAGACAGATATCCGAGTGAACCTGTGGGCCACCGGCCTCATGGGCGCACC

ATCTGCCTCCACTCGGTGGCCGTCTGCCCTCGTCTCCAGGGCTTGGGTCT

CGGTACTGCGACTCTGAAGTCGTATGTGCAGCGCATGAACAGCCTCGGCG

CCGCGGACCGTGTTGCTCTCGTTTGCCGCAAGCCCGAGACGAGATTTTTT

GAAAGATGCGGCTTCAGGAACAGCGGCCGGAGTAGTATCAAGACTCTGGT

CGGCGAATACTACAACATGGTGTGTCTTCCACATCGACTTGGCCAGACT

CTATACGATTTTCAAACCTCGCTATACGTCATATTGACTTGTTTCTTTAG

GTCTTCGATTTGCCCGGGCCCAAAGACTTTATCGACTGGAATAGCATTGC

CGACGCTGCCAAGAAGATGTGAACCATTTGACTGATACGATGTGTGCTAC

GCATGTCGACCTTCTTTGTTTGTTTCTTTGGCGGCTCTTTGTATACCTTG

GGACACGGCAGACGCATGTCTATGTGAAGAAAACGTTCACGGCGCTGTTT

GCATCAGGAATATGATCATTAAACATGGAGCGTAATGGTATTAATGATCA

ACTAGAAAAATGGTATGGAAGGGCGAGAGGGCGATCAACAAAGCAGCCCG

GGGCATAGTCTGGAAGCAGCAGGAATTGGAAGGGAAAAGGAAGCTGCACA

ATGAAGGGATATCGTGAGCGGAGTGGCTCACGAGAGTATCAACAGACTGG

CGAAAGCAAGCAATTGCCAACGCCGGCTATTAGGCCATAAGATGGCCTGT

TGTGAGTCCCAGTTGCACGTATCCCCATATGACTGCTCTGTCGCTGACTT

GAAAAAAAATAGGGAGGATAAAGGAGAAAGAAAGTGAGACAACCCGTGAG

GGACTTGGGGTAGTAGGAGAACACATGGGCAACCGGGCAATACACGCGAT

GTGAGACGAGTTCAACGGCGAATGGAAAATCTTGAAAAACAAAATAAAAT

AACTGCCCTCCATACGGGTATCAAATTCAAGCAGTTGTACGGAGGCTAGA

TAGAGTTGTGAAGTCGGTAATCCCGCTGTATAGTAATACGAGTCGCATCT

AAATACTCCGAAGCTGCTGCGAACCCGGAGAATCGAGATGTGCTGGAAAG

CTTCTAGCGAGCGGCTAAATTAGCATGAAAGGCTATGAGAAATTCTGGAG

ACGGCTTGTTGAATCATGGCGTTCCATTCTTCGACAAGCAAAGCGTTCCG

TCGCAGTAGCAGGCACTCATTCCCGAAAAAACTCGGAGATTCCTAAGTAG

CGATGGAACCGGAATAATATAATAGGCAATACATTGAGTTGCCTCGACGG

TTGCAATGCAGGGGTACTGAGCTTGGACATAACTGTTCCGTACCCCACCT

-continued

CTTCTCAACCTTTGGCGTTTCCCTGATTCAGCGTACCCGTACAAGTCGTA
ATCACTATTAACCCAGACTGACCGGACGTGTTTTGCCCTTCATTTGGAGA
AATAATGTCATTGCGATGTGTAATTTGCCTGCTTGACCGACTGGGGCTGT
TCGAAGCCCGAATGTAGGATTGTTATCCGAACTCTGCTCGTAGAGGCATG
TTGTGAATCTGTGTCGGGCAGGACACGCCTCGAAGGTTCACGGCAAGGGA
AACCACCGATAGCAGTGTCTAGTAGCAACCTGTAAAGCCGCAATGCAGCA
TCACTGGAAAATACAAACCAATGGCTAAAAGTACATAAGTTAATGCCTAA
AGAAGTCATATACCAGCGGCTAATAATTGTACAATCAAGTGGCTAAACGT
ACCGTAATTTGCCAACGGCTTGTGGGGTTGCAGAAGCAACGGCAAAGCCC
CACTTCCCCACGTTTGTTTCTTCACTCAGTCCAATCTCAGCTGGTGATCC
CCCAATTGGGTCGCTTGTTTGTTCCGGTGAAGTGAAAGAAGACAGAGGTA
AGAATGTCTGACTCGGAGCGTTTTGCATACAACCAAGGGCAGTGATGGAA
GACAGTGAAATGTTGACATTCAAGGAGTATTTAGCCAGGGATGCTTGAGT
GTATCGTGTAAGGAGGTTTGTCTGCCGATACGACGAATACTGTATAGTCA
CTTCTGATGAAGTGGTCCATATTGAAATGTAAAGTCGGCACTGAACAGGC
AAAAGATTGAGTTGAAACTGCCTAAGATCTCGGGCCCTCGGGCCTTCGGC
CTTTGGGTGTACATGTTTGTGCTCCGGGCAAATGCAAAGTGTGGTAGGAT
CGAACACACTGCTGCCTTTACCAAGCAGCTGAGGGTATGTGATAGGCAAA
TGTTCAGGGGCCACTGCATGGTTTCGAATAGAAAGAGAAGCTTAGCCAAG
AACAATAGCCGATAAAGATAGCCTCATTAAACGGAATGAGCTAGTAGGCA
AAGTCAGCGAATGTGTATATATAAAGGTTCGAGGTCCGTGCCTCCCTCAT
GCTCTCCCCATCTACTCATCAACTCAGATCCTCCAGGAGACTTGTACACC
ATCTTTTGAGGCACAGAAACCCAATAGTCAACCGCGGACTGCGCATCATG
TATCGGAAGTTGGCCGTCATCTCGGCCTTCTTGGCCACACCTCGTGCTAG
ACTAGGCGCGTCAATATGTGGCCGTTACTCGAGTTTATAAGTGACAACAT
GCTCTCAAAGCGCTCATGGCTGGCACAAGCCTGGAAAGAACCAACACAAA
GCATACTGCAGCAAATCAGCTGAATTCGTCACCAATTAAGTGAACATCAA
CCTGAAGGCAGAGTATGAGGCCAGAAGCACATCTGGATCGCAGATCATGG
ATTGCCCCTCTTGTTGAAGATGAGAATCTAGAAAGATGGCGGGTATGAG
ATAAGAGCGATGGGGGGGCACATCATCTTCCAAGACAAACAACCTTTGCA
GAGTCAGGCAATTTTTCGTATAAGAGCAGGAGGAGGGAGTCCAGTCATTT
CATCAGCGGTAAAATCACTCTAGACAATCTTCAAGATGAGTTCTGCCTTG
GGTGACTTATAGCCATCATCATACCTAGACAGAAGCTTGTGGGATACTAA
GACCAACGTACAAGCTCGCACTGTACGCTTTGACTTCCATGTGAAAACTC
GATACGGCGCGCCTCTAAATTTTATAGCTCAACCACTCCAATCCAACCTC
TGCATCCCTCTCACTCGTCCTGATCTACTGTTCAAATCAGAGAATAAGGA
CACTATCCAAATCCAACAGAATGGCTACCACCTCCCAGCTGCCTGCCTAC
AAGCAGGACTTCCTCAAATCCGCCATCGACGGCGGCGTCCTCAAGTTTGG
CAGCTTCGAGCTCAAGTCCAAGCGGATATCCCCCTACTTCTTCAACGCGG
GCGAATTCCACACGGCGCGCCTCGCCGGCGCCATCGCCTCCGCCTTTGCA

-continued

AAGACCATCATCGAGGCCCAGGAGAAGGCCGGCCTAGAGTTCGACATCGT
CTTCGGCCCGGCCTACAAGGGCATCCCGCTGTGCTCCGCCATCACCATCA
AGCTCGGCGAGCTGGCGCCCCAGAACCTGGACCGCGTCTCCTACTCGTTT
GACCGCAAGGAGGCCAAGGACCACGGCGAGGGCGGCAACATCGTCGGCGC
TTCGCTCAAGGGCAAGAGGGTCCTGATTGTCGACGACGTCATCACCGCCG
GCACCGCCAAGAGGGACGCCATTGAGAAGATCACCAAGGAGGGCGGCATC
GTCGCCGGCATCGTCGTGGCCCTGGACCGCATGGAGAAGCTCCCCGCTGC
GGATGGCGACGACTCCAAGCCTGGACCGAGTGCCATTGGCGAGCTGAGGA
AGGAGTACGGCATCCCCATCTTTGCCATCCTCACTCTGGATGACATTATC
GATGGCATGAAGGGCTTTGCTACCCCTGAGGATATCAAGAACACGGAGGA
TTACCGTGCCAAGTACAAGGCGACTGACTGATTGAGGCGTTCAATGTCAG
AAGGGAGAGAAAGACTGAAAAGGTGGAAAGAAGAGGCAAATTGTTGTTAT
TATTATTATTCTATCTCGAATCTTCTAGATCTTGTCGTAAATAAACAAGC
GTAACTAGCTAGCCTCCGTACAACTGCTTGAATTTGATACCCGTATGGAG
GGCAGTTATTTTATTTTGTTTTTCAAGATTTTCCATTCGCCGTTGAACTC
GTCTCACATCGCGTGTATTGCCCGGTTGCCCATGTGTACGCGTTTCGGGT
TTACCTCTTCCAGATACAGCTCATCTGCAATGCATTAATGCATTGGACCT
CGCAACCCTAGTACGCCCTTCAGGCTCCGGCGAAGCAGAAGAATAGCTTA
GCAGAGTCTATTTTCATTTTCGGGAGACTAGCATTCTGTAAACGGGCAGC
AATCGCCCAGCAGTTAGTAGGGTCCCCTCTACCTCTCAGGGAGATGTAAC
AACGCCACCTTATGGGACTATCAAGCTGACGCTGGCTTCTGTGCAGACAA
ACTGCGCCCACGAGTTCTTCCCTGACGCCGCTCTCGCGCAGGCAAGGGAA
CTCGATGAATACTACGCAAAGCACAAGAGACCCGTTGGTCCACTCCATGG
CCTCCCCATCTCTCTCAAAGACCAGCTTCGAGTCAAGGTACACCGTTGCC
CCTAAGTCGTTAGATGTCCCTTTTTGTCAGCTAACATATGCCACCAGGGC
TACGAAACATCAATGGGCTACATCTCATGGCTAAACAAGTACGACGAAGG
GGACTCGGTTCTGACAACCATGCTCCGCAAAGCCGGTGCCGTCTTCTACG
TCAAGACCTCTGTCCCGCAGACCCTGATGGTCTGCGAGACAGTCAACAAC
ATCATCGGGCGCACCGTCAACCCACGCAACAAGAACTGGTCGTGCGGCGG
CAGTTCTGGTGGTGAGGGTGCGATCGTTGGGATTCGTGGTGGCGTCATCG
GTGTAGGAACGGATATCGGTGGCTCGATTCGAGTGCCGGCCGCGTTCAAC
TTCCTGTACGGTCAAGGCCGAGTCATGGGCGGCTGCCGTATGCAAAGAT
GGCGAACAGCATGGAGGGTCAGGAGACGGTGCACAGCGTTGTCGGGCCGA
TTACGCACTCTGTTGAGGGTGAGTCCTTCGCCTCTTCCTTCTTTTCCTGC
TCTATACCAGGCCTCCACTGTCCTCCTTTCTTGCTTTTTATACTATATAC
GAGACCGGCAGTCACTGATGAAGTATGTTAGACCTCCGCCTCTTCACCAA
ATCCGTCCTCGGTCAGGAGCCATGGAAATACGACTCCAAGGTCATCCCCA
TGCCCTGGCGCCAGTCCGAGTCGGACATTATTGCCTCCAAGATCAAGAAC
GGCGGGCTCAATATCGGCTACTACAACTTCGACGGCAATGTCCTTCCACA
CCCTCCTATCCTGCGCGGCGTGGAAACCACCGTCGCCGCACTCGCCAAAG
CCGGTCACACCGTGACCCCGTGGACGCCATACAAGCACGATTTCGGCCAC

```
GATCTCATCTCCCATATCTACGCGGCTGACGGCAGCGCCGACGTAATGCG

CGATATCAGTGCATCCGGCGAGCCGGCGATTCCAAATATCAAAGACCTAC

TGAACCCGAACATCAAAGCTGTTAACATGAACGAGCTCTGGGACACGCAT

CTCCAGAAGTGGAATTACCAGATGGAGTACCTTGAGAAATGGCGGGAGGC

TGAAGAAAAGGCCGGGAAGGAACTGGACGCCATCATCGCGCCGATTACGC

CTACCGCTGCGGTACGGCATGACCAGTTCCGGTACTATGGGTATGCCTCT

GTGATCAACCTGCTGGATTTCACGAGCGTGGTTGTTCCGGTTACCTTTGC

GGATAAGAACATCGATAAGAAGAATGAGAGTTTCAAGGCGGTTAGTGAGC

TTGATGCCCTCGTGCAGGAAGAGTATGATCCGGAGGCGTACCATGGGCA

CCCGGTTGCAGTGCAGGTTATCGGACGGAGACTCAGTGAAGAGAGGACGTT

GGCGATTGCAGAGGAAGTGGGGAAGTTGCTGGGAAATGTGGTGACTCCAT

AGCTAATAAGTGTCAGATAGCAATTTGCACAAGAAATCAATACCAGCAAC

TGTAAATAAGCGCTGAAGTGACCATGCCATGCTACGAAAGAGCAGAAAAA

AACCTGCCGTAGAACCGAAGAGATATGACACGCTTCCATCTCTCAAAGGA

AGAATCCCTTCAGGGTTGCGTTTCCAGTAGTGATTTTACCGCTGATGAAA

TGACTGGACTCCCTCCTCCTGCTCTTATACGAAAAATTGCCTGACTCTGC

AAAGGTTGTTTGTCTTGGAAGATGATGTGCCCCCCCATCGCTCTTATCTC

ATACCCCGCCATCTTTCTAGATTCTCATCTTCAACAAGAGGGGCAATCCA

TGATCTGCGATCCAGATGTGCTTCTGGCCTCATACTCTGCCTTCAGGTTG

ATGTTCACTTAATTGGTGACGAATTCAGCTGATTTGCTGCAGTATGCTTT

GTGTTGGTTCTTTCCAGGCTTGTGCCAGCCATGAGCGCTTTGAGAGCATG

TTGTCACTTATAAACTCGAGTAACGGCCACATATTGTTCACTACTTGAAT

CACATACCTAATTTTGATAGAATTGACATGTTTAAAGAGCTGAGGTAGCT

TTAATGCCTCTGAAGTATTGTGACACAGCTTCTCACAGAGTGAGAATGAA

AAGTTGGACTCCCCCTAATGAAGTAAAAGTTTCGTCTCTGAACGGTGAAG

AGCATAGATCCGGCATCAACTACCTGGCTAGACTACGACGTCAATTCTGC

GGCCTTTTGACCTTTATATATGTCCATTAATGCAATAGATTCTTTTTTTT

TTTTTTTTTTTTTTTTTTTTTTTTTTTTTGCCCAATTTCGCAGATC

AAAGTGGACGTTATAGCATCATAACTAAGCTCAGTTGCTGAGGGAAGCCG

TCTACTACCTTAGCCCATCCATCCAGCTCCATACCTTGATACTTTAGACG

TGAAGCAATTCACACTGTACGTCTCGCAGCTCTCCTTCCCGCTCTTGCTT

CCCCACTGGGGTCCATGGTGCGTGTATCGTCCCCTCCACAATTCTATGCC

ATGGTACCTCCAGCTTATCAATGCCCCGCTAACAAGTCGCCTCTTTGCCT

TGATAGCTTATCGATAAACTTTTTTTCCGCCAGAAAGGCTCCGCCCACA

GACAAGAAAAAAATTCACCGCCTAGCCTTTGGCCCCGGCATTTGGCTAA

ACCTCGAGCCTCTCTCCCGTCTTGGGGTATCAGGAAGAAAAGAAAAAAAT

CCATCGCCAAGGGCTGTTTTGGCATCACCACCCGAAAACAGCACTTCCTC

GATCAAAAGTTGCCCGCCATGAAGACCACGTGGAAGGACATCCCTCCGGT

GCCTACGCACCAGGAGTTTCTGGACATTGTGCTGAGCAGGACCCAGCGCA

AACTGCCCACTCAGATCCGTGCCGGCTTCAAGATTAGCAGAATTCGAGGT

ACGTCGCATTGCCCATCGCAGGATGTCTCATTATCGGGGTCCTTGGAGAA

CGATCATGATTGCATGGCGATGCTAACACATAGACAGCCTTCTACACTCG

AAAGGTCAAGTTCACCCAGGAGACGTTTTCCGAAAAGTTCGCCTCCATCC

TCGACAGCTTCCCTCGCCTCCAGGACATCCACCCCTTCCACAAGGACCTT

CTCAACACCCTCTACGATGCCGACCACTTCAAGATTGCCCTTGGCCAGAT

GTCCACTGCCAAGCACCTGGTCGAGACCATCTCGCGCGACTACGTCCGTC

TCTTGAAATACGCCCAGTCGCTCTACCAGTGCAAGCAGCTCAAGCGGGCC

GCTCTCGGTCGCATGGCCACGCTGGTCAAGCGCCTCAAGGACCCCCTGCT

GTACCTGGACCAGGTCCGCCAGCATCTCGGCCGTCTTCCCTCCATCGACC

CCAACACCAGGACCCTGCTCATCTGCGGTTACCCCAATGTTGGCAAGTCC

AGCTTCCTGCGAAGTATCACCCGCGCCGATGTGGACGTCCAGCCCTATGC

TTTCACCACCAAGAGTCTGTTTGTCGGCCACTTTGACTACAAGTACCTGC

GATTCCAGGCCATTGATACCCCCGGTATTCTGGACCACCCTCTTGAGGAG

ATGAACACTATCGAAATGCAGAGGTATGTGGCGCGGCT
```

Creation of the A5D Strain from the Archy3 *T. reesei* Strain

Figure 5:
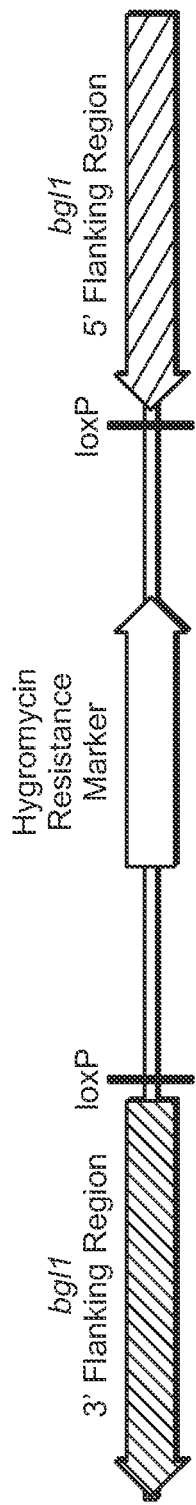
Figure 7:
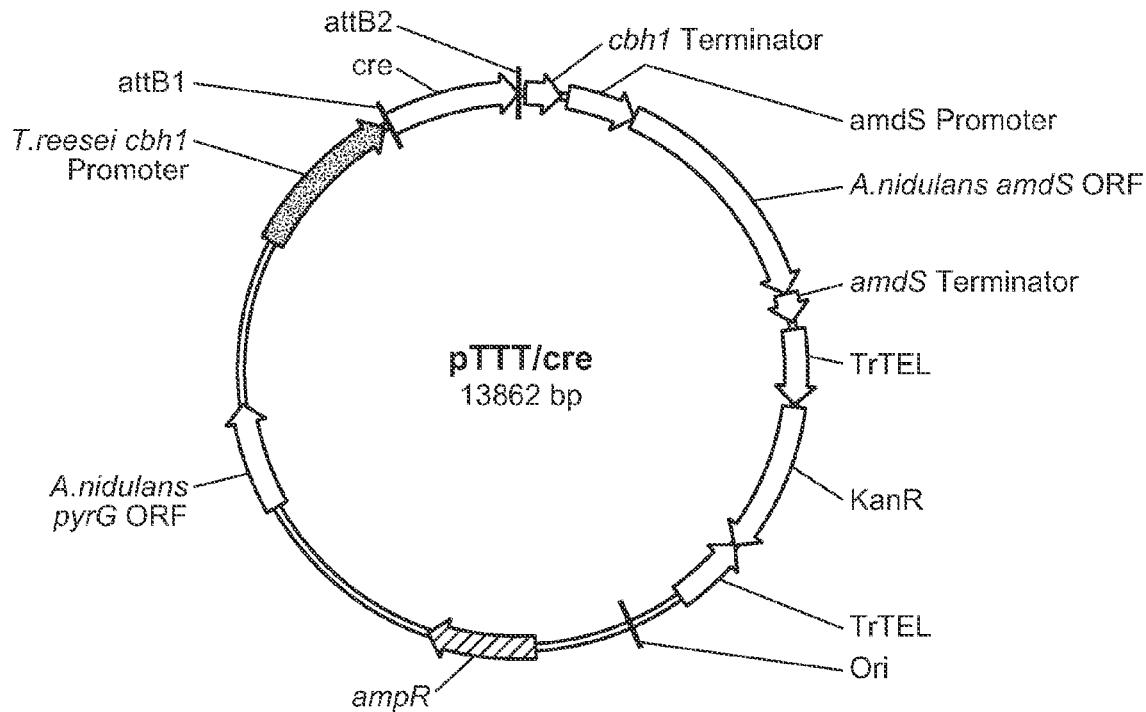

Native *T. reesei* bgl1 was deleted from the Archy 3 strain using a double crossover recombination gene replacement vector known in the art, e.g. M. Ward, et al. (1990). Gene 86(2): 153-62. Hygromycin resistance was used as the selectable marker for bgl1 deletion. In addition, the hygromycin resistance marker was flanked by loxP sites. The bgl1 deletion cassette is depicted in FIG. 5. Subsequent hygromycin resistant transformants were analyzed for bgl1 deletion. A strain confirmed for deletion of bgl1 was then transformed with a telomeric vector encoding cre recombinase and a functional amdS for selection of transformants to facilitate removal of the hygromycin by cre recombinase expression and loop out of the loxP sites. The telomeric vector encoding the cre recombinase is schematically depicted in FIG. 7. Transformants were first obtained on acetamide media, then transferred to potato dextrose agar and replica plated onto hygromycin media to screen for hygromycin sensitivity. Strains sensitive to hygromycin, were again transferred to potato dextrose media and replica plated to acetamide media. A strain was selected, which had lost its capacity to grow on acetamide, indicating a loss of the telomeric vector. The nucleotide sequence of the bgl1 knockout cassette is provided as SEQ ID NO:4:

```
AATGGTAGGAATGCTGGGATATAGGCTCTGTGCTGGCAAGTTGATGGATC

CTCGAATGAGGCCGCCCTGCAAGGGGAACATCAGAGATCTACCATTGCCT

CCTTGGCCCAATCCACTATCATACCTACCTCATGATCATTCCTGCGAAGG

TCTACCAGTAAATATTTCCTCGTCCCGTGTTTCATCATGTCCAGAACCTC

ATCTCGCCAAATTGACTTTGCCACAGTGTCTGGAGCTGGGTAAGCAGCGT

GCCAAGGAATTGTTGTCGAGTCTGTGCCAGGCATTGTGCCCGACATTGTG

AACTTCAGCCAGGAGAACTTTTCGATCGCACCTATGCTGAGCACCGTGGG

CATGCGATGGCTTCAATAATGCAGTTCGAGAGGGAGTGTGTCATGCCCTA

AAGCTCATTGGCCACCTCCACAGGCTAGCTCTACCTGCATCTGTAGATGG

ACTTTCCTTGTCCTCCTCCTTCAGAAAACCTCTTGGTCGCTCGCAGGTAA
```

-continued

```
CTGTTGTTGCCGTCATTGTTTGACAGTGGATAGCCAAGGCAAAACCGTCT
GCTTTCAACGGAAGCATTCGGCGGTTGTTTGTCATCGTGTTATCGATCGA
CCAGGAGAACCCAGACGAGTGTTGTTCGAGAGAATCATCGACGATGTGAA
GAGGCGACGACTAGTATCTAGAAGATTATAATCGAACAAATCAGCGTTTG
TCTGTCGGGCGTTTGAGGGCGCAGTTGCCCGCCAAAGCAGCGTCGCAATA
TATAGGCAGCGAGAGACTGTCAACAGCCAGCCGCCATGTGATCGATCGTA
GCCGTCTTCCCGATCTTCCCTAAACCCCTTTCTTTGGGGGGCGGGGCAG
CGGCGTTCTAATATTTGCTGGCTGTCTGGATAACGTGAATGGTAGACATG
GTAATGTTCGGTCTGCGAAACATTTGTACAATTGGAGTTTACGATCGAGA
TGGAAGGAAACGCTCCACAAACTCGGTGACTGGGTTGCCATCAGGTGCTC
AGGGCATAGCGTTCTCTGCAAATAGAGGAAAGAGAATAGCACTAGTGAAA
GTGTGAATCACAATGAAGAGGAGGTTGTTGCCGGAATGCTTTGAGCAGCG
TCAAAGTTGAACTTGAAGCTATCACAAATTGCAGGGTAAAGTACATGTTG
GTGCCAGTTTGACAGCACAGTGCGCGGAGCGGAGGATGTCGCGGAAGAGG
CGCGACGCTAACCCGGGCCTTCTTCTCAGTGAGCAGAACTCCTGCTGCAA
GAGTTCCTTCTCTGCGAGATGACGTGAGGCCCAATTTGCAGCTTCCCT
CGAACAAGGTGATTGAACATCTCTCTTCCCTCACATTTCATCATCACTAC
CTCCTCAATTCACTTCTGCTTCGGCCGTCTTCATCATTCATGTTACTGCT
CTGATGCCTATCCTGAAGATTGTATTCCTGCAGTATTCACGCCATCCCAC
CTTCGGTCCTCACTCACAGTCACAGGTCAACCGCCTTCACCCTCCTCGCG
ATGATGTCGGCAATCTGGTGGATCAATGTGCGGTTGAGGGCCGCCGTAGT
GAGGATGGGCATGGGAACGAGGTCGCCCATTCGCCCACAGATAACTTCG
TATAGCATACATTATACGAAGTTATCCTGGGCTTGTGACTGGTCGCGAGC
TGCCACTAAGTGGGGCAGTACCATTTTATCGGACCCATCCAGCTATGGGA
CCCACTCGCAAATTTTTACATCATTTTCTTTTTGCTCAGTAACGGCCACC
TTTTGTAAAGCGTAACCAGCAAACAAATTGCAATTGGCCCGTAGCAAGGT
AGTCAGGGCTTATCGTGATGGAGGAGAAGGCTATATCAGCCTCAAAAATA
TGTTGCCAGCTGGCGGAAGCCCGGAAGGTAAGTGGATTCTTCGCCGTGGC
TGGAGCAACCGGTGGATTCCAGCGTCTCCGACTTGGACTGAGCAATTCAG
CGTCACGGATTCACGATAGACAGCTCAGACCGCTCCACGGCTGGCGGCAT
TATTGGTTAACCCGGAAACTCAGTCTCCTTGGCCCCGTCCCGAAGGGACC
CGACTTACCAGGCTGGGAAAGCCAGGGATAGAATACACTGTACGGGCTTC
GTACGGGAGGTTCGGCGTAGGGTTGTTCCCAAGTTTTACACACCCCCAA
GACAGCTAGCGCACGAAAGACGCGGAGGGTTTGGTGAAAAAGGGCGAAA
ATTAAGCGGGAGACGTATTTAGGTGCTAGGGCCGGTTTCCTCCCCATTTT
TCTTCGGTTCCCTTTCTCTCCTGGAAGACTTTCTCTCTCTCTTCTTCT
CTTCTTCCATCCTCAGTCCATCTTCCTTTCCCATCATCCATCTCCTCACC
TCCATCTCAACTCCATCACATCACAATCGATATGAAAAAGCCTGAACTCA
CCGCGACGTCTGTCGAGAAGTTTCTGATCGAAAAGTTCGACAGCGTCTCC
GACCTGATGCAGCTCTCGGAGGGCGAAGAATCTCGTGCTTTCAGCTTCGA
TGTAGGAGGGCGTGGATATGTCCTGCGGGTAAATAGCTGCGCCGATGGTT
TCTACAAAGATCGTTATGTTTATCGGCACTTTGCATCGGCCGCGCTCCCG
ATTCCGGAAGTGCTTGACATTGGGGAATTCAGCGAGAGCCTGACCTATTG
CATCTCCCGCCGTGCACAGGGTGTCACGTTGCAAGACCTGCCTGAAACCG
AACTGCCCGCTGTTCTGCAGCCGGTCGCGGAGGCCATGGATGCGATCGCT
GCGGCCGATCTTAGCCAGACGAGCGGGTTCGGCCCATTCGGACCGCAAGG
AATCGGTCAATACACTACATGGCGTGATTTCATATGCGCGATTGCTGATC
CCCATGTGTATCACTGGCAAACTGTGATGGACGACACCGTCAGTGCGTCC
GTCGCGCAGGCTCTCGATGAGCTGATGCTTTGGGCCGAGGACTGCCCCGA
AGTCCGGCACCTCGTGCACGCGGATTTCGGCTCCAACAATGTCCTGACGG
ACAATGGCCGCATAACAGCGGTCATTGACTGGAGCGAGGCGATGTTCGGG
GATTCCCAATACGAGGTCGCCAACATCTTCTTCTGGAGGCCGTGGTTGGC
TTGTATGGAGCAGCAGACGCGCTACTTCGAGCGGAGGCATCCGGAGCTTG
CAGGATCGCCGCGGCTCCGGGCGTATATGCTCCGCATTGGTCTTGACCAA
CTCTATCAGAGCTTGGTTGACGGCAATTTCGATGATGCAGCTTGGGCGCA
GGGTCGATGCGACGCAATCGTCCGATCCGGAGCCGGGACTGTCGGGCGTA
CACAAATCGCCCGCAGAAGCGCGGCCGTCTGGACCGATGGCTGTGTAGAA
GTACTCGCCGATAGTGGAAACCGACGCCCCAGCACTCGTCCGAGGGCAAA
GGAATAGAGTAGATGCCGACCGGGATCCACTTAACGTTACTGAAATCATC
AAACAGCTTGACGAATCTGGATATAAGATCGTTGGTGTCGATGTCAGCTC
CGGAGTTGAGACAAATGGTGTTCAGGATCTCGATAAGATACGTTCATTTG
TCCAAGCAGCAAAGAGTGCCTTCTAGTGATTTAATAGCTCCATGTCAACA
AGAATAAAACGCGTTTCGGGTTTACCTCTTCCAGATACAGCTCATCTGCA
ATGCATTAATGCATTGGACCTCGCAACCCTAGTACGCCCTTCAGGCTCCG
GCGAAGCAGAAGAATAGCTTAGCAGAGTCTATTTTCATTTTCGGGAGACG
AGATCAAGCAGATCAACGGTCGTCAAGAGACCTACGAGACTGAGGAATCC
GCTCTTGGCTCCACGCGACTATATATTTGTCTCTAATTGTACTTTGACAT
GCTCCTCTTCTTTACTCTGATAGCTTGACTATGAAAATTCCGTCACCAGC
CCCTGGGTTCGCAAAGATAATTGCACTGTTTCTTCCTTGAACTCTCAAGC
CTACAGGACACACATTCATCGTAGGTATAAACCTCGAAAATCATTCCTAC
TAAGATGGGTATACAATAGTAACCATGGTTGCCTAGTGAATGCTCCGTAA
CACCCAATACGCCGGCCGATAACTTCGTATAGCATACATTATACGAAGTT
ATACTTGGCGCGCCTAGTGGAACACGAGCACATAAGCTTTTACCTATGGT
TATCGCTTGCATCTACGCGCCGTTGATGGTGGAGGATGGTGGACGTTCCC
GAGACCCCTACGAGCTGTGGCATCGTCAAACTGTGCCCACAGACCTTTGT
CTTGCTTTCATAACCTCGAGGAGTGTTTCCAGACTCATCATCCATACACA
AGCAGTATTAATCAAAGAAACTCGGTCGCAATGGCAAAATGGTTTGCAA
ACAGAAAACTATGGCCTCTTCCTATTCCATCATTAACTACTCTACCCGTT
TGTCATAACAACATCATTAAAACCCTTATGCGTCAGGTGTAGCATCCTTG
ATCTGTTGCTCCTCCAACGGCCAGTTCTCAATCGTTACCTCTTCTCCCAC
CAACTCAAACTCAAGCTTCACAGACTCGTCGGTGTTCAAGGCTAGCTCAT
```

```
ACTTGCCGGGGTATACAATCCGGTTTCCGTGAGAATCAACACGGGCGAGA
GCACTGACAGGGATGGGGATGCTGAGCTTGGAAGAGTGACCAGGCTTGAT
GTCGGCAAGTCGGTCGAATCCGACGAGCCACTTGTTCGGGTACGGGGCTG
GGCCAGCGTTGCTTGTGCGAACAAACAGCATGGCCGTATATGGGGACTCC
GTCTTGCCCGAGTTCTTGATGTTGGCCTCGAAGGTGAAGACGGGAATCTG
CTCGCTGTAAGTGTATCCGGGGTGAGGAGCAGAGAGGATCGATGAGGTGT
TGAACTTGAGGCTCTTGGGGTGGCTGGCGAGAGTCTCCTTGAAGGTGGTG
TAGAAGAGACCACTGCCAAACTCGTAGACGGGTTTGCCGGTGTACCAGAT
GTAAGTCTGTCCAGGGTTTGACTTTCCATCGGGTCGGAGGTTCATGTCAT
TCTGGGGAATTGGTGAACATACTCAGCCGGGTACTGAGTGGTGACCAGT
CGGCCGGCAGGAGCACGCTTGCCAGAGAGAATGTCGAAGAGGGCAACGCC
TCCCGACTGGCCGGGATATCCGCCCCAGACGAGGGAGTTGACCTTCTTGT
TGCTCTTGAGCGAGGATGAGTCTACCTGACCACCGCCCATTTGCAGGACG
ACAAGGGGTTTGCCGACCTCGCTGAGCTGCTTGATGAGATCCAGCTGATT
ACCGGGCCAAGCAATGTCCGTGCGGTCAGCGCCCTCCTGTTCAATGGTGT
TGTCAATTCCACCGAGGTAGATGATGGCATCCGACTTCTTGGCGGCAGCA
ATGGCCTTGGCAAAGCCAGTGGTGCTGTTGCCGGCGATCTCTGTGCCGAG
TTCAAAGTTGACGTGATAGCCGGCCTTCTTAGCAGCTTCCAGAGGGCTGA
TGAGGTATGGGGCAGGGCCATAGTAGTTGCCTTGCATTTGGGTTGTGGCA
TTGGCCCATGGTCCGATCAGAGCAATGCTGCGCACCTTCTTGGACAGAGG
GAGAGTGCCATCGTTCTTGAGCAGGACGATGCCCTCAACAGCAGCCTCGT
ACGAGATGTT
```

The nucleotide sequence of the telomeric vector, pTTT-cre, is provided as SEQ ID NO:5:

```
TTGTACAAAGTGGTGATCGCGCCGCGCGCCAGCTCCGTGCGAAAGCCTGA
CGCACCGGTAGATTCTTGGTGAGCCCGTATCATGACGGCGGCGGGAGCTA
CATGGCCCCGGGTGATTTATTTTTTTTGTATCTACTTCTGACCCTTTTCA
AATATACGGTCAACTCATCTTTCACTGGAGATGCGGCCTGCTTGGTATTG
CGATGTTGTCAGCTTGGCAAATTGTGGCTTTCGAAAACACAAAACGATTC
CTTAGTAGCCATGCATTTTAAGATAACGGATAGAAGAAAGAGGAAATTAA
AAAAAAAAAAAAAAACAACATCCCGTTCATAACCCGTAGAATCGCCGCT
CTTCGTGTATCCCAGTACCAGTTTATTTTGAATAGCTCGCCCGCTGGAGA
GCATCCTGAATGCAAGTAACAACCGTAGAGGCTGACACGGCAGGTGTTGC
TAGGGAGCGTCGTGTTCTACAAGGCCAGACGTCTTCGCGGTTGATATATA
TGTATGTTTGACTGCAGGCTGCTCAGCGACGACAGTCAAGTTCGCCCTCG
CTGCTTGTGCAATAATCGCAGTGGGGAAGCCACACCGTGACTCCCATCTT
TCAGTAAAGCTCTGTTGGTGTTTATCAGCAATACACGTAATTTAAACTCG
TTAGCATGGGGCTGATAGCTTAATTACCGTTTACCAGTGCCATGGTTCTG
CAGCTTTCCTTGGCCCGTAAAATTCGGCGAAGCCAGCCAATCACCAGCTA
GGCACCAGCTAAACCCTATAATTAGTCTCTTATCAACACCATCCGCTCCC
CCGGGATCAATGAGGAGAATGAGGGGGATGCGGGGCTAAAGAAGCCTACA
TAACCCTCATGCCAACTCCCAGTTTACACTCGTCGAGCCAACATCCTGAC
TATAAGCTAACACAGAATGCCTCAATCCTGGGAAGAACTGGCCGCTGATA
AGCGCGCCCGCCTCGCAAAAACCATCCCTGATGAATGGAAAGTCCAGACG
CTGCCTGCGGAAGACAGCGTTATTGATTTCCCAAAGAAATCGGGGATCCT
TTCAGAGGCCGAACTGAAGATCACAGAGGCCTCCGCTGCAGATCTTGTGT
CCAAGCTGGCGGCCGGAGAGTTGACCTCGGTGGAAGTTACGCTAGCATTC
TGTAAACGGGCAGCAATCGCCCAGCAGTTAGTAGGGTCCCCTCTACCTCT
CAGGGAGATGTAACAACGCCACCTTATGGGACTATCAAGCTGACGCTGGC
TTCTGTGCAGACAAACTGCGCCCACGAGTTCTTCCCTGACGCCGCTCTCG
CGCAGGCAAGGGAACTCGATGAATACTACGCAAAGCACAAGAGACCCGTT
GGTCCACTCCATGGCCTCCCCATCTCTCTCAAAGACCAGCTTCGAGTCAA
GGTACACCGTTGCCCCTAAGTCGTTAGATGTCCCTTTTTGTCAGCTAACA
TATGCCACCAGGGCTACGAAACATCAATGGGCTACATCTCATGGCTAAAC
AAGTACGACGAAGGGGACTCGGTTCTGACAACCATGCTCCGCAAAGCCGG
TGCCGTCTTCTACGTCAAGACCTCTGTCCCGCAGACCCTGATGGTCTGCG
AGACAGTCAACAACATCATCGGGCGCACCGTCAACCCACGCAACAAGAAC
TGGTCGTGCGGCGGCAGTTCTGGTGGTGAGGGTGCGATCGTTGGGATTCG
TGGTGGCGTCATCGGTGTAGGAACGGATATCGGTGGCTCGATTCGAGTGC
CGGCCGCGTTCAACTTCCTGTACGGTCTAAGGCCGAGTCATGGGCGGCTG
CCGTATGCAAAGATGGCGAACAGCATGGAGGGTCAGGAGACGGTGCACAG
CGTTGTCGGGCCGATTACGCACTCTGTTGAGGGTGAGTCCTTCGCCTCTT
CCTTCTTTTCCTGCTCTATACCAGGCCTCCACTGTCCTCCTTTCTTGCTT
TTTATACTATATACGAGACCGGCAGTCACTGATGAAGTATGTTAGACCTC
CGCCTCTTCACCAAATCCGTCCTCGGTCAGGAGCCATGGAAATACGACTC
CAAGGTCATCCCCATGCCCTGGCGCCAGTCCGAGTCGGACATTATTGCCT
CCAAGATCAAGAACGGCGGGCTCAATATCGGCTACTACAACTTCGACGGC
AATGTCCTTCCACACCCTCCTATCCTGCGCGGCGTGGAAACCACCGTCGC
CGCACTCGCCAAAGCCGGTCACACCGTGACCCCGTGGACGCCATACAAGC
ACGATTTCGGCCACGATCTCATCTCCCATATCTACGCGGCTGACGGCAGC
GCCGACGTAATGCGCGATATCAGTGCATCCGGCGAGCCGGCGATTCCAAA
TATCAAAGACCTACTGAACCCGAACATCAAAGCTGTTAACATGAACGAGC
TCTGGGACACGCATCTCCAGAAGTGGAATTACCAGATGGAGTACCTTGAG
AAATGGCGGGAGGCTGAAGAAAGGCCGGGAAGGAACTGGACGCCATCAT
CGCGCCGATTACGCCTACCGCTGCGGTACGGCATGACCAGTTCCGGTACT
ATGGGTATGCCTCTGTGATCAACCTGCTGGATTTCACGAGCGTGGTTGTT
CCGGTTACCTTTGCGGATAAGAACATCGATAAGAAGAATGAGAGTTTCAA
GGCGGTTAGTGAGCTTGATGCCCTCGTGCAGGAAGAGTATGATCCGGAGG
CGTACCATGGGCACCGGTTGCAGTGCAGGTTATCGGACGGAGACTCAGT
GAAGAGAGGACGTTGGCGATTGCAGAGGAAGTGGGGAAGTTGCTGGGAAA
```

-continued

```
TGTGGTGACTCCATAGCTAATAAGTGTCAGATAGCAATTTGCACAAGAAA
TCAATACCAGCAACTGTAAATAAGCGCTGAAGTGACCATGCCATGCTACG
AAAGAGCAGAAAAAAACCTGCCGTAGAACCGAAGAGATATGACACGCTTC
CATCTCTCAAAGGAAGAATCCCTTCAGGGTTGCGTTTCCAGTCTAGACAC
GTATAACGGCACAAGTGTCTCTCACCAAATGGGTTATATCTCAAATGTGA
TCTAAGGATGGAAAGCCCAGAATATCGATCGCGCGCAGATCCATATATAG
GGCCCGGGTTATAATTACCTCAGGAAATAGCTTTAAGTAGCTTATTAAGT
ATTAAAATTATATATATTTTTAATATAACTATATTTCTTTAATAAATAGG
TATTTTAAGCTTTATATATAAATATAATAAAATAATATATTATATAG
CTTTTTATTAATAAATAAAATAGCTAAAAATATAAAAAAAATAGCTTTAA
AATACTTATTTTTAATTAGAATTTTATATATTTTTAATATATAAGATCTT
TTACTTTTTTATAAGCTTCCTACCTTAAATTAAATTTTTACTTTTTTTTA
CTATTTTACTATATCTTAAATAAAGGCTTTAAAAATATAAAAAAAAATCTT
CTTATATATTATAAGCTATAAGGATTATATATATATTTTTTTTTAATTTT
TAAAGTAAGTATTAAAGCTAGAATTAAAGTTTTAATTTTTTAAGGCTTTA
TTTAAAAAAAGGCAGTAATAGCTTATAAAAGAAATTTCTTTTTCTTTTAT
ACTAAAAGTACTTTTTTTTTAATAAGGTTAGGGTTAGGGTTAGGGTTAGG
GTTAGGGTTAGGGTTAGGGTTAGGGTTAGGGTTAGGGTTAGGGTTAGGGT
TAGGGTTAGGGTTAGGGTAAGGGTTTAAACAAAGCCACGTTGTGTCTCAA
AATCTCTGATGTTACATTGCACAAGATAAAAATATATCATCATGAACAAT
AAAACTGTCTGCTTACATAAACAGTAATACAAGGGGTGTTATGAGCCATA
TTCAACGGGAAACGTCTTGCTCGAGGCCGCGATTAAATTCCAACATGGAT
GCTGATTTATATGGGTATAAATGGGCTCGCGATAATGTCGGGCAATCAGG
TGCGACAATCTATCGATTGTATGGGAAGCCCGATGCGCCAGAGTTGTTTC
TGAAACATGGCAAAGGTAGCGTTGCCAATGATGTTACAGATGAGATGGTC
AGACTAAACTGGCTGACGGAATTTATGCCTCTTCCGACCATCAAGCATTT
TATCCGTACTCCTGATGATGCATGGTTACTCACCACTGCGATCCCCGGGA
AAACAGCATTCCAGGTATTAGAAGAATATCCTGATTCAGGTGAAAATATT
GTTGATGCGCTGGCAGTGTTCCTGCGCCGGTTGCATTCGATTCCTGTTTG
TAATTGTCCTTTTAACAGCGATCGCGTATTTCGTCTCGCTCAGGCGCAAT
CACGAATGAATAACGGTTTGGTTGATGCGAGTGATTTTGATGACGAGCGT
AATGGCTGGCCTGTTGAACAAGTCTGGAAAGAAATGCATAAGCTTTTGCC
ATTCTCACCGGATTCAGTCGTCACTCATGGTGATTTCTCACTTGATAACC
TTATTTTTGACGAGGGGAAATTAATAGGTTGTATTGATGTTGGACGAGTC
GGAATCGCAGACCGATACCAGGATCTTGCCATCCTATGGAACTGCCTCGG
TGAGTTTTCTCCTTCATTACAGAAACGGCTTTTTCAAAAATATGGTATTG
ATAATCCTGATATGAATAAATTGCAGTTTCATTTGATGCTCGATGAGTTT
TTCTAATCAGAATTGGTTAATTGGTTGTAACACTGGCAGAGCATTACGCT
GACTTGACGGGACGGCGGCTTTGTTGAATAAATCGAACTTTTGCTGAGTT
GAAGGATCAGATCACGCATCTTCCCGACAACGCAGACCGTTCCGTGGCAA
AGCAAAAGTTCAAAATCACCAACTGGTCCACCTACAACAAAGCTCTCATC
AACCGTGGCTCCCTCACTTTCTGGCTGGATGATGGGGCGATTCAGGCCTG
GTATGAGTCAGCAACACCTTCTTCACGAGGCAGACCTCAGCGGTTTAAAC
CTAACCCTAACCCTAACCCTAACCCTAACCCTAACCCTAACCCTAACCCT
AACCCTAACCCTAACCCTAACCCTAACCCTAACCCTAACCTAACCCTAAT
GGGGTCGATCTGAACCGAGGATGAGGGTTCTATAGACTAATCTACAGGCC
GTACATGGTGTGATTCAGATGCGACGGGCAAGGTGTACAGTGTCCAGAA
GGAGGAGAGCGGCATAGGTATTGTAATAGACCAGCTTTACATAATAATCG
CCTGTTGCTACTGACTGATGACCTTCTTCCCTAACCAGTTTCCTAATTAC
CACTGCAGTGAGGATAACCCTAACTCGCTCTGGGGTTATTATTATACTGA
TTAGCAGGTGGCTTATATAGTGCTGAAGTACTATAAGAGTTTCTGCGGGA
GGAGGTGGAAGGACTATAAACTGGACACAGTTAGGGATAGAGTGATGACA
AGACCTGAATGTTATCCTCCGGTGTGGTATAGCGAATTGGCTGACCTTGC
AGATGGTAATGGTTTAGGCAGGGTTTTTGCAGAGGGGGACGAGAACGCGT
TCTGCGATTTAACGGCTGCTGCCGCCAAGCTTTACGGTTCTCTAATGGGC
GGCCGCCTCAGGTCGACGTCCCATGGCCATTCGAATTCGTAATCATGGTC
ATAGCTGTTTCCTGTGTGAAATTGTTATCCGCTCACAATTCCACACAACA
TACGAGCCGGAAGCATAAAGTGTAAAGCCTGGGGTGCCTAATGAGTGAGC
TAACTCACATTAATTGCGTTGCGCTCACTGCCCGCTTTCCAGTCGGGAAA
CCTGTCGTGCCAGCTGCATTAATGAATCGGCCAACGCGCGGGGAGAGGCG
GTTTGCGTATTGGGCGCTCTTCCGCTTCCTCGCTCACTGACTCGCTGCGC
TCGGTCGTTCGGCTGCGGCGAGCGGTATCAGCTCACTCAAAGGCGGTAAT
ACGGTTATCCACAGAATCAGGGGATAACGCAGGAAAGAACATGTGAGCAA
AAGGCCAGCAAAAGGCCAGGAACCGTAAAAAGGCCGCGTTGCTGGCGTTT
TTCCATAGGCTCCGCCCCCCTGACGAGCATCACAAAAATCGACGCTCAAG
TCAGAGGTGGCGAAACCCGACAGGACTATAAAGATACCAGGCGTTTCCCC
CTGGAAGCTCCCTCGTGCGCTCTCCTGTTCCGACCCTGCCGCTTACCGGA
TACCTGTCCGCCTTTCTCCCTTCGGGAAGCGTGGCGCTTTCTCATAGCTC
ACGCTGTAGGTATCTCAGTTCGGTGTAGGTCGTTCGCTCCAAGCTGGGCT
GTGTGCACGAACCCCCCGTTCAGCCCGACCGCTGCGCCTTATCCGGTAAC
TATCGTCTTGAGTCCAACCCGGTAAGACACGACTTATCGCCACTGGCAGC
AGCCACTGGTAACAGGATTAGCAGAGCGAGGTATGTAGGCGGTGCTACAG
AGTTCTTGAAGTGGTGGCCTAACTACGGCTACACTAGAAGAACAGTATTT
GGTATCTGCGCTCTGCTGAAGCCAGTTACCTTCGGAAAAGAGTTGGTAG
CTCTTGATCCGGCAAACAAACCACCGCTGGTAGCGGTGGTTTTTTTGTTT
GCAAGCAGCAGATTACGCGCAGAAAAAAAGGATCTCAAGAAGATCCTTTG
ATCTTTTCTACGGGGTCTGACGCTCAGTGGAACGAAAACTCACGTTAAGG
GATTTTGGTCATGAGATTATCAAAAAGGATCTTCACCTAGATCCTTTTAA
ATTAAAAATGAAGTTTTAAATCAATCTAAAGTATATATGAGTAAACTTGG
TCTGACAGTTACCAATGCTTAATCAGTGAGGCACCTATCTCAGCGATCTG
TCTATTTCGTTCATCCATAGTTGCCTGACTCCCCGTCGTGTAGATAACTA
```

```
CGATACGGGAGGGCTTACCATCTGGCCCCAGTGCTGCAATGATACCGCGA
GACCCACGCTCACCGGCTCCAGATTTATCAGCAATAAACCAGCCAGCCGG
AAGGGCCGAGCGCAGAAGTGGTCCTGCAACTTTATCCGCCTCCATCCAGT
CTATTAATTGTTGCCGGGAAGCTAGAGTAAGTAGTTCGCCAGTTAATAGT
TTGCGCAACGTTGTTGCCATTGCTACAGGCATCGTGGTGTCACGCTCGTC
GTTTGGTATGGCTTCATTCAGCTCCGGTTCCCAACGATCAAGGCGAGTTA
CATGATCCCCATGTTGTGCAAAAAAGCGGTTAGCTCCTTCGGTCCTCCG
ATCGTTGTCAGAAGTAAGTTGGCCGCAGTGTTATCACTCATGGTTATGGC
AGCACTGCATAATTCTCTTACTGTCATGCCATCCGTAAGATGCTTTTCTG
TGACTGGTGAGTACTCAACCAAGTCATTCTGAGAATAGTGTATGCGGCGA
CCGAGTTGCTCTTGCCCGGCGTCAATACGGGATAATACCGCGCCACATAG
CAGAACTTTAAAAGTGCTCATCATTGGAAAACGTTCTTCGGGGCGAAAAC
TCTCAAGGATCTTACCGCTGTTGAGATCCAGTTCGATGTAACCCACTCGT
GCACCCAACTGATCTTCAGCATCTTTTACTTTCACCAGCGTTTCTGGGTG
AGCAAAAACAGGAAGGCAAAATGCCGCAAAAAAGGGAATAAGGGCGACAC
GGAAATGTTGAATACTCATACTCTTCCTTTTTCAATATTATTGAAGCATT
TATCAGGGTTATTGTCTCATGAGCGGATACATATTTGAATGTATTTAGAA
AAATAAACAAATAGGGGTTCCGCGCACATTTCCCCGAAAAGTGCCACCTG
ACGTCTAAGAAACCATTATTATCATGACATTAACCTATAAAAATAGGCGT
ATCACGAGGCCCTTTCGTCTCGCGCGTTTCGGTGATGACGGTGAAAACCT
CTGACACATGCAGCTCCCGGAGACGGTCACAGCTTGTCTGTAAGCGGATG
CCGGGAGCAGACAAGCCCGTCAGGGCGCGTCAGCGGGTGTTGGCGGGTGT
CGGGGCTGGCTTAACTATGCGGCATCAGAGCAGATTGTACTGAGAGTGCA
CCATAAAATTGTAAACGTTAATATTTTGTTAAAATTCGCGTTAAATTTTT
GTTAAATCAGCTCATTTTTTAACCAATAGGCCGAAATCGGCAAAATCCCT
TATAAATCAAAAGAATAGCCCGAGATAGGGTTGAGTGTTGTTCCAGTTTG
GAACAAGAGTCCACTATTAAAGAACGTGGACTCCAACGTCAAAGGGCGAA
AAACCGTCTATCAGGGCGATGGCCCACTACGTGAACCATCACCCAAATCA
AGTTTTTTGGGGTCGAGGTGCCGTAAAGCACTAAATCGGAACCCTAAAGG
GAGCCCCCGATTTAGAGCTTGACGGGGAAAGCCGGCGAACGTGGCGAGAA
AGGAAGGGAAGAAAGCGAAAGGAGCGGGCGCTAGGGCGCTGGCAAGTGTA
GCGGTCACGCTGCGCGTAACCACCACACCCGCCGCGCTTAATGCGCCGCT
ACAGGGCGCGTACTATGGTTGCTTTGACGTATGCGGTGTGAAATACCGCA
CAGATGCGTAAGGAGAAAATACCGCATCAGGCGCCATTCGCCATTCAGGC
TGCGCAACTGTTGGGAAGGGCGATCGGTGCGGGCCTCTTCGCTATTACGC
CAGCTGGCGAAAGGGGGATGTGCTGCAAGGCGATTAAGTTGGGTAACGCC
AGGGTTTTCCCAGTCACGACGTTGTAAAACGACGGCCAGTGCCCAAGCTT
ACTAGATGCATGCTCGAGCGGCCGCCAGTGTGATGGATATCTGCAGAATT
CGCCCTTGACTAGTGCTCTCTATCCTGGTGGCAGGCGTCAAGTACCCAGA
GGCAGCAGCGGGCTTAGGAGCGGCCTGGGTTGTTCTCCGCACCCTCTACA
TGCTGGGCTATATTTATAGCGACAAGCCGAACGGCACCGGCAGGTACAAT

GGTTCGCTGTACTTGCTTGCGCAAGCGGGTCTTTGGGGATTGAGCGCATT
TGGTGTTGCAAAGGATTTGATGTAAATGTAGTCGACATCTTAGCACAGAG
GGGAGAGTTGATAAAATGTGGTCTGTTTGAATGATAGTCGGGTTCGTGAC
CTATATTCGTGATAGTGGAGATAGGTCTGCGCCTATCTTATCGGGCCGGA
GCAAAAATTCCACCGCAGCGGGGTGAGTTTTCGTTATACAGCCATCCCAC
TTCCAGCTTCAAATTGTCAGTTTAATCCAGCCCAATTCAATCATTGGAGA
ACCGCCATCATGTCTTCGAAGTCCCACCTCCCCTACGCAATTCGCGCAAC
CAACCATCCCAACCCTTTAACATCTAAACTCTTCTCCATCGCCGAGGAGA
AGAAAACCAACGTCACCGTCTCCGCAGACGTTACTACTTCCGCCGAGCTC
CTCGATCTTGCTGACCGTACATCCTGCACCAATGCCCCTCCAGGATAACA
AATAGCTGATGCGTAGTGAGTACAGGCCTAGGCCCCTATATCGCAGTTCT
GAAAACCCACATCGACATCCTCACCGATCTCACCCCGTCGACCCTTTCCT
CGCTCCAATCCCTCGCGACAAAGCACAACTTCCTCATCTTTGAGGACCGC
AAGTTCATCGACATCGGCAACACCGTGCAAAAGCAGTACCACGGTGGCGC
TCTCCGCATCTCCGAATGGGCACACATCATCAACTGCGCCATCCTGCCGG
GCGAAGGGATCGTCGAGGCCCTCGCACAGACAACCAAGTCTCCTGACTTT
AAAGACGCGAATCAACGAGGTCTCCTGATTCTTGCCGAGATGACGAGTAA
GGGATCTCTTGCGACAGGGGAGTCACAGGCACGCTCGGTTGAGTACGCGC
GGAAGTATAAGGGGTTTGTGATGGGATTCGTGAGTACAAGGGCGTTGAGT
GAGGTGCTGCCCGAACAGAAAGAGGAGAGCGAGGATTTTGTCGTCTTTAC
GACTGGGGTGAATCTGTCGGATAAGGGGGATAAGCTGGGGCAGCAGTATC
AGACACCTGGGTCGGCGGTTGGGCGAGGTGCGGACTTTATCATTGCGGGT
AGGGGCATCTATAAGGCGGACGATCCAGTCGAGGCGGTTCAGAGGTACCG
GGAGGAAGGCTGGAAAGCTTACGAGAAAAGAGTTGGACTTTGAGTGTGAG
TGGAAATGTGTAACGGTATTGACTAAAAGGGATCCATATGTTTATTGCAG
CCAGCATAGTATTACCAGAAAGAGCCTCACTGACGGCTCTAGTAGTATTC
GAACAGATATTATTGTGACCAGCTCTGAACGATATGCTCCCTAATCTGGT
AGACAAGCACTGATCTACCCCTTGGAACGCAGCATCTAGGCTCTGGCTGT
GCTCTAACCCTAACTAGACGATTGATCGCAGACCATCCAATACTGAAAAG
TCTCTATCAGAGGAAATCCCCAACATTGTAGTAGTCAGGTTCCTTTGTGG
CTGGGAGAGAATTGGTTCGCTCCACTGATTCCAGTTGAGAAAGTGGGCTA
GAAAAAAGTCTTGAAGATTGGAGTTGGGCTGTGGTTATCTAGTACTTCTC
GAGCTCTGTACATGTCCGGTCGCGACGTACGCGTATCGATGGCGCCAGCT
GCAGGCGGCCGCCTGCAGCCACTTGCAGTCCCGTGGAATTCTCACGGTGA
ATGTAGGCCTTTTGTAGGGTAGGAATTGTCACTCAAGCACCCCCAACCTC
CATTACGCCTCCCCCATAGAGTTCCCAATCAGTGAGTCATGGCACTGTTC
TCAAATAGATTGGGGAGAAGTTGACTTCCGCCCAGAGCTGAAGGTCGCAC
AACCGCATGATATAGGGTCGGCAACGGCAAAAAAGCACGTGGCTCACCGA
AAAGCAAGATGTTTGCGATCTAACATCCAGGAACCTGGATACATCCATCA
TCACGCACGACCACTTTGATCTGCTGGTAAACTCGTATTCGCCCTAAACC
```

```
GAAGTGCGTGGTAAATCTACACGTGGGCCCCTTTCGGTATACTGCGTGTG
TCTTCTCTAGGTGCCATTCTTTTCCCTTCCTCTAGTGTTGAATTGTTTGT
GTTGGAGTCCGAGCTGTAACTACCTCTGAATCTCTGGAGAATGGTGGACT
AACGACTACCGTGCACCTGCATCATGTATATAATAGTGATCCTGAGAAGG
GGGGTTTGGAGCAATGTGGGACTTTGATGGTCATCAAACAAAGAACGAAG
ACGCCTCTTTTGCAAAGTTTTGTTTCGGCTACGGTGAAGAACTGGATACT
TGTTGTGTCTTCTGTGTATTTTTGTGGCAACAAGAGGCCAGAGACAATCT
ATTCAAACACCAAGCTTGCTCTTTTGAGCTACAAGAACCTGTGGGGTATA
TATCTAGAGTTGTGAAGTCGGTAATCCCGCTGTATAGTAATACGAGTCGC
ATCTAAATACTCCGAAGCTGCTGCGAACCCGGAGAATCGAGATGTGCTGG
AAAGCTTCTAGCGAGCGGCTAAATTAGCATGAAAGGCTATGAGAAATTCT
GGAGACGGCTTGTTGAATCATGGCGTTCCATTCTTCGACAAGCAAAGCGT
TCCGTCGCAGTAGCAGGCACTCATTCCCGAAAAAACTCGGAGATTCCTAA
GTAGCGATGGAACCGGAATAATATAATAGGCAATACATTGAGTTGCCTCG
ACGGTTGCAATGCAGGGGTACTGAGCTTGGACATAACTGTTCCGTACCCC
ACCTCTTCTCAACCTTTGGCGTTTCCCTGATTCAGCGTACCCGTACAAGT
CGTAATCACTATTAACCCAGACTGACCGGACGTGTTTTGCCCTTCATTTG
GAGAAATAATGTCATTGCGATGTGTAATTTGCCTGCTTGACCGACTGGGG
CTGTTCGAAGCCCGAATGTAGGATTGTTATCCGAACTCTGCTCGTAGAGG
CATGTTGTGAATCTGTGTCGGGCAGGACACGCCTCGAAGGTTCACGGCAA
GGGAAACCACCGATAGCAGTGTCTAGTAGCAACCTGTAAAGCCGCAATGC
AGCATCACTGGAAAATACAAACCAATGGCTAAAAGTACATAAGTTAATGC
CTAAAGAAGTCATATACCAGCGGCTAATAATTGTACAATCAAGTGGCTAA
ACGTACCGTAATTTGCCAACGGCTTGTGGGGTTGCAGAAGCAACGGCAAA
GCCCCACTTCCCCACGTTTGTTTCTTCACTCAGTCCAATCTCAGCTGGTG
ATCCCCCAATTGGGTCGCTTGTTTGTTCCGGTGAAGTGAAAGAAGACAGA
GGTAAGAATGTCTGACTCGGAGCGTTTTGCATACAACCAAGGGCAGTGAT
GGAAGACAGTGAAATGTTGACATTCAAGGAGTATTTAGCCAGGGATGCTT
GAGTGTATCGTGTAAGGAGGTTTGTCTGCCGATACGACGAATACTGTATA
GTCACTTCTGATGAAGTGGTCCATATTGAAATGTAAAGTCGGCACTGAAC
AGGCAAAAGATTGAGTTGAAACTGCCTAAGATCTCGGGCCCTCGGGCCTT
CGGCCTTTGGGTGTACATGTTTGTGCTCCGGGCAAATGCAAAGTGTGGTA
GGATCGAACACACTGCTGCCTTTACCAAGCAGCTGAGGGTATGTGATAGG
CAAATGTTCAGGGGCCACTGCATGGTTTCGAATAGAAAGAGAAGCTTAGC
CAAGAACAATAGCCGATAAAGATAGCCTCATTAAACGGAATGAGCTAGTA
GGCAAAGTCAGCGAATGTGTATATATAAAGGTTCGAGGTCCGTGCCTCCC
TCATGCTCTCCCCATCTACTCATCAACTCAGATCCTCCAGGAGACTTGTA
CACCATCTTTTGAGGCACAGAAACCCAATAGTCAACCATCACAAGTTTGT
ACAAAAAAGCAGGCTCACCATGAGCAACCTGCTCACCGTCCACCAGAACC
TCCCTGCCCTCCCTGTCGACGCCACCTCTGACGAGGTCCGCAAGAACCTC
ATGGACATGTTCCGCGACCGCCAGGCCTTTAGCGAGCACACCTGGAAGAT
GCTCCTCAGCGTCTGCCGATCTTGGGCCGCCTGGTGCAAGCTCAACAACC
GCAAGTGGTTCCCCGCCGAGCCGGAGGACGTCCGCGACTACCTCCTCTAC
CTGCAGGCCCGAGGCCTGGCCGTCAAGACCATCCAGCAGCACCTCGGCCA
GCTCAACATGCTCCACCGACGCTCTGGCCTGCCTCGCCCTAGCGACTCTA
ACGCCGTCAGCCTGGTCATGCGCCGCATCCGCAAGGAGAACGTCGACGCT
GGCGAGCGAGCCAAGCAGGCCCTCGCCTTCGAGCGCACCGACTTCGACCA
GGTCCGCAGCCTCATGGAGAACAGCGACCGCTGCCAGGATATCCGCAACC
TCGCCTTTCTCGGCATTGCCTACAACACCCTGCTCCGCATTGCCGAGATC
GCCCGCATCCGCGTCAAGGACATCTCTCGCACCGACGGCGGCCGCATGCT
CATTCACATCGGCCGCACCAAGACCCTCGTGTCTACCGCCGGCGTCGAGA
AGGCCCTCAGCCTCGGCGTCACCAAGCTCGTCGAGCGCTGGATTTCTGTC
TCCGGCGTCGCTGACGACCCCAACAACTACCTCTTCTGCCGCGTCCGAAA
GAACGGCGTCGCCGCCCCTTCTGCCACCTCTCAGCTCAGCACCCGAGCCC
TGGAGGGCATCTTTGAGGCCACCCACCGCCTCATCTACGGCGCCAAGGAC
GACTCTGGCCAGCGCTACCTCGCCTGGTCTGGCCACTCTGCCCGAGTCGG
CGCTGCCCGAGACATGGCCCGAGCCGGCGTCAGCATCCCCGAGATTATGC
AGGCCGGCGGCTGGACCAACGTCAACATCGTCATGAACTACATCCGCACC
CTCGACTCTGAGACCGGCGCCATGGTCCGACTCCTCGAGGACGGCGACTA
AACCCAGCTTTC
```

Creation of the MAD6 Strain from A5D *T. reesei* Strain

Figure 6:

Native egl3 was deleted from the A5D strain (above) using a similar method as the one previously described for bgl1 deletion (see, supra). A schematic of the egl3 deletion cassette is shown in FIG. 6. Hygromycin resistance was used as the selectable marker for egl3 deletion. The hygromycin resistance marker was flanked by loxP sites. A transformant was confirmed to have a deletion of the egl3. The hygromycin marker was removed from this strain as described for creation of the A5D strain. The telomeric vector encoding the cre recombinase was removed from this strain as described for the creation of the A5D strain. The nucleotide sequence of the egl3 deletion cassette is provided as SEQ ID NO:6:

```
GGGAGGTAGGCGCAGATACGGTGCATGGGACCCGAACCCGTAACCGGAAC
ACGACCTTATCAGCCCTCCAACTCACACCCTCTCGCCTATCACTATCCTA
GATAGTTCATCGGCCAACTCATGTAACCTAGCTACCTACCTACCTGGTAA
GAATGCGGGCTATCATGTCTCACGGCGCGGTACATGTCGGTATCTCGCTG
CTTCCCCGCAGGTTGACGTCGGAATCCATGCAAGTACTCCCTGAAATCGA
GACGACAGAGAGAACAACCAACGCGCTTAAACGCTTCATGTTCATCTAAG
AGGCACATTCGAAGAACTAGCTTAACACACTAGACCTGGCTTTTCGACCC
CCTCCGCAGAAAGCCGTTTTCTCCTCAATCCTCCCGGGCTTGGCTTTTGT
CAGTCCGTACTTGCTGCGCTAACAGAGTCTTGGACGCAGCGTTTGCGCAT
CAGTCTTGCAGGCGGTTCACGGGACTAGGACAACAGGGGATGTGACAGGC
CGGATAGTAATTATGGGTTATCCGGGGTAAGCAGGGAATTTACGAGGCCG
```

-continued

```
CTTTACGTGGGGGAACAGCCACTTGCGGGGGAAGAGGAGTAGTAGGCGA
CTCGGTCGATGAGCTCGAGGTGTCTGTTGACTTGGACTGCAGAGCGTAG
GTAATTGAGATCGGGCAACATTATCGGTGTTCGGCTCGGTATGGCCGAGT
TGCGACTGCTTGGTCATTCGGCGAAGCTGATGTCGTGGTATCCTGAAGCA
TCGATATCGGAAACCATGATGGTCAGTCTATCTGACGTGTGCGGTGACAA
GCGAGTCCGGATTTTGTGACATGACGTTCAACTTCAGTCAATGCCTTAGG
GCTCGATAAGATTAAGATTGGGTTCTGGCAGCGGTCTAGAACACCGCCAC
AAATTCTGTCCATTGAGGAGCGTGATGTCTAGGCGCATCACTAACACGGA
GCTGTATGACCGGCAGCTCAACGGACTTCTCTTCGTTCAACGGCAGTCTA
TTTGCGGTACACGAATGGATCTTTCTTCCTGGTCTTGAAGTGCCGCAGTG
GCGTGCGAATGTATAGATGTCTCGCTACCTAGAAAAGCTGGCTTTTCTGA
CAGGGTCCCTTCCACCTCTCCTACCAACGACAAACTGAACAAGTATCTGG
CGGTTTCCCAACGCCGAATAGGCCAGTCGCCAATACTCCCTCCAGCCCTG
ATTGGGCCCCTCGAAGTATCGCCATGTCTGTGTGTTGAGATTATTCGATG
GACGTCACTCCCCCAACCTACAGGAAGAGCAAAATGGGAGCAGTGTTCTG
CAATGAGCTATATAATAGATCGCTCGATCTCATACAAATTGTATGCTCAG
TCAATACAACGAGCGGTTCCAAGATCCCTTCTCCAACGACCCTCGAAACA
TTGCAACCCGGTGCAGCCTGAACTTGTTCGTATAGCCTAGAAAGCGACGC
CATCTTCATCTTTTACGCGATTAGCCTCATGGCTATTTGTGCCGAAGTGG
GAGTTGTATGGTAGCAGTGAGGAGATTGTGGCTACGACACAGGCGGGTTC
TCTTGAGCGGCTTACATCTCCGCATTAGGCCTGCGTACGATCCAGATCAT
GGGAAACTTTACAATGGCTTACTCGTTTTATCTCAACACTGAGCTTCCAA
TTCACTCTATGCATTGATTAACACGTTTGGTCATGTGGTTCTTCAGCTGT
AAATCTTCAGCTTCCCAAGAATTGCAACCTCGCTGATTGCTAATAGTGTT
GCATGCGTTGCATCCTGGTGCGGCAGTGCAAAGGAGAGTCAAAGTAGCCG
GCAGATTAATTTAAGCTTATATCACTCAGGGGTAAACAGCCGTAAAGGAC
CTTTTGATCTAACATGCCGATGTGTATGTAGATCACGCAATGCCCACCAT
ATCTTGGCAGTCAGATTTGTCCGTGGCGCGCCAAGTATAACTTCGTATAA
TGTATGCTATACGAAGTTATCGGCCGGCGTATTGGGTGTTACGGAGCATT
CACTAGGCAACCATGGTTACTATTGTATACCCATCTTAGTAGGAATGATT
TTCGAGGTTTATACCTACGATGAATGTGTGTCCTGTAGGCTTGAGAGTTC
AAGGAAGAAACAGTGCAATTATCTTTGCGAACCCAGGGGCTGGTGACGGA
ATTTTCATAGTCAAGCTATCAGAGTAAAGAAGAGGAGCATGTCAAAGTAC
AATTAGAGACAAATATATAGTCGCGTGGAGCCAAGAGCGGATTCCTCAGT
CTCGTAGGTCTCTTGACGACCGTTGATCTGCTTGATCTCGTCTCCCGAAA
ATGAAAATAGACTCTGCTAAGCTATTCTTCTGCTTCGCCGGAGCCTGAAG
GGCGTACTAGGGTTGCGAGGTCCAATGCATTAATGCATTGCAGATGAGCT
GTATCTGGAAGAGGTAAACCCGAAACGCGTTTTATTCTTGTTGACATGGA
GCTATTAAATCACTAGAAGGCACTCTTTGCTGCTTGGACAAATGAACGTA
TCTTATCGAGATCCTGAACACCATTTGTCTCAACTCCGGAGCTGACATCG
ACACCAACGATCTTATATCCAGATTCGTCAAGCTGTTTGATGATTTCAGT
```

-continued

```
AACGTTAAGTGGATCCCGGTCGGCATCTACTCTATTCCTTTGCCCTCGGA
CGAGTGCTGGGGCGTCGGTTTCCACTATCGGCGAGTACTTCTACACAGCC
ATCGGTCCAGACGGCCGCGCTTCTGCGGGCGATTTGTGTACGCCCGACAG
TCCCGGCTCCGGATCGGACGATTGCGTCGCATCGACCCTGCGCCCAAGCT
GCATCATCGAAATTGCCGTCAACCAAGCTCTGATAGAGTTGGTCAAGACC
AATGCGGAGCATATACGCCCGGAGCCGCGGCGATCCTGCAAGCTCCGGAT
GCCTCCGCTCGAAGTAGCGCGTCTGCTGCTCCATACAAGCCAACCACGGC
CTCCAGAAGAAGATGTTGGCGACCTCGTATTGGGAATCCCCGAACATCGC
CTCGCTCCAGTCAATGACCGCTGTTATGCGGCCATTGTCCGTCAGGACAT
TGTTGGAGCCGAAATCCGCGTGCACGAGGTGCCGGACTTCGGGGCAGTCC
TCGGCCCAAAGCATCAGCTCATCGAGAGCCTGCGCGACGGACGCACTGAC
GGTGTCGTCCATCACAGTTTGCCAGTGATACACATGGGGATCAGCAATCG
CGCATATGAAATCACGCCATGTAGTGTATTGACCGATTCCTTGCGGTCCG
AATGGGCCGAACCCGCTCGTCTGGCTAAGATCGGCCGCAGCGATCGCATC
CATGGCCTCCGCGACCGGCTGCAGAACAGCGGGCAGTTCGGTTTCAGGCA
GGTCTTGCAACGTGACACCCTGTGCACGGCGGGAGATGCAATAGGTCAGG
CTCTCGCTGAATTCCCCAATGTCAAGCACTTCCGGAATCGGGAGCGCGGC
CGATGCAAAGTGCCGATAAACATAACGATCTTTGTAGAAACCATCGGCGC
AGCTATTTACCCGCAGGACATATCCACGCCCTCCTACATCGAAGCTGAAA
GCACGAGATTCTTCGCCCTCCGAGAGCTGCATCAGGTCGGAGACGCTGTC
GAACTTTTCGATCAGAAACTTCTCGACAGACGTCGCGGTGAGTTCAGGCT
TTTTCATATCGATTGTGATGTGATGGAGTTGAGATGGAGGTGAGGAGATG
GATGATGGGAAAGGAAGATGGACTGAGGATGGAAGAAGAGAAGAAGAGAG
AGAGAGAAAGTCTTCCAGGAGAGAAAGGGAACCGAAGAAAAATGGGGAGG
AAACCGGCCCTAGCACCTAAATACGTCTCCCGCTTAATTTTCGCCCTTTT
TTCACCAAACCCTCCGCGTCTTTCGTGCGCTAGCTGTCTTGGGGGGTGTG
TAAAACTTGGGAACAACCCTACGCCGAACCTCCCGTACGAAGCCCGTACA
GTGTATTCTATCCCTGGCTTTCCCAGCCTGGTAAGTCGGGTCCCTTCGGG
ACGGGGCCAAGGAGACTGAGTTTCCGGGTTAACCAATAATGCCGCCAGCC
GTGGAGCGGTCTGAGCTGTCTATCGTGAATCCGTGACGCTGAATTGCTCA
GTCCAAGTCGGAGACGCTGGAATCCACCGGTTGCTCCAGCCACGGCGAAG
AATCCACTTACCTTCCGGGCTTCCGCCAGCTGGCAACATATTTTTGAGGC
TGATATAGCCTTCTCCTCCATCACGATAAGCCCTGACTACCTTGCTACGG
GCCAATTGCAATTTGTTTGCTGGTTACGCTTTACAAAAGGTGGCCGTTAC
TGAGCAAAAGAAAATGATGTAAAAATTTGCGAGTGGGTCCCATAGCTGG
ATGGGTCCGATAAAATGGTACTGCCCCACTTAGTGGCAGCTCGCGACCAG
TCACAAGCCCAGGATAACTTCGTATAATGTATGCTATACGAAGTTATCTG
TGGGCGTTATGAATAATAGACTGGAACCGGGCCCTTTGATTGACGACTCC
ATATTTTGTAGATGTAGCAACTCGGCAAGAGCATTATGTGCAATACATTT
GTTACCATACAAAGGCAGCTGCCAGACGACTTGTATTGCGTACAATTCTC
```

-continued
```
ACGGCAAGCTTTCCAGGTGTTATGCATTATGCGCAAATGCTTGATGCTTA
CCGCAGGATTAATCTCGGAAGAAGCGCTGCAAGCTATATGGGTGTAGTAG
ATATGTAGATGTACCAACCAATGAAGAACATTTATGGTCTAGAACGTAGT
GATGAAGGTTTTGAGTAATTTGTATCAAGTAAGACGATATTATTGATATA
ATACCAAGCATATATTCATGATAAATTACTTGGAACCACCCTTGCGTCCG
GCCTCACGAGCCTTCTCACTGCCGGGCTCGAAGGAGCCACTGGAGGCCTG
TCCACCCTTGGATGCGATTTCCTGCACCTTTTCCTTGGGCCTGCACGTCG
ATTAGACATGATTCAAATCGAGATCTTGGAATATCTTACATGCTGGCGAA
GCCACCGGTGTGGCTGGACTGTCCGCCCTTCTGCGCAATGCTTTGAACCT
CCTCCTTGGGCTGTGTAGAAAGGTTTGTTAGCAACATTACTACAACTCT
CAGGACTCGGTGGTCGTACCGGTTGGCGAAGTTTCCGGGGTTATCGTTGC
CAGACATTGTGTGATTATTTGGTGTGCAAATGTGTGCTATGTGTGTTGTT
GCTGTTGGTGATGATGCTGAAGCTGTTGAAAGCAGGCTGGTTCTGTGGGA
GAGACTTGGGATATTTATATCCAAAGTTCGGTCGTGTTCCTTCTGGAAGC
TCTTCTCTACTCCATACAATCATCCAAAGTTGTCGTCATTGAGCGTTGAT
CAGTAGTAGCCTCTGAGGTCATCACCATGATCCTTCCGGCCAACAGTCGG
CACTCATCAACAGCAACAATCAGCCGCCACAAACATAGGTACAGTAAGGA
GTTAGATATCATGTAGTCGTCGAGTACTCGACATCATGACGTACAAGCTT
TGCCAGTGTCGGTAGGTGCAAGTATGATGATCGTATCCGCCGTTGTTCGA
TCGAACAGAGTGCGGTCAGATTCACGGTTTCTCTCACCTTGAACATTGGA
TGCAATTGGATTGATCCACAATCCTGGAGAATGGCTTCAAGCTCACTGCT
CCAGTCGCAAGCTTCAGAGCCTATTACTAAGGGTAGAGCTACCTATGTCA
AGAGTTTTCAAGGTACCTAAGCTACATGTGATAGTCGGCAAGCCATTTTG
AACGCAGACCGTGAACGGTGATGTAAATCCGGGATAGACGCCCAAGCGTG
CCGTGTCAATGACGCTAGATACACCTCGATTTACGTAGAGTGAATGCCAG
CCAATGGAGTCATGCACATAACCCGCTTAGACTCTGCTCGGGGCGATACC
CGATCGCAGAGGCAGAGCCGCTTAAACGCGATCGCGGTAACCTGTAATCA
GAGCCAGCGCTCGATGAATTGCATCATGGAAGCCATTGATGTGGAATGTT
GAGCGTATAACAACACGAATTGAAGACGACATTGACTTGCTTCAAGTGAG
TGGAGAATTGCCGGGCAGACAAGATAGGTAGGCTCTTGGTGCGCTGTCAC
ATCAATCCATTCCTTTTCCTCTGTTCAATCTCTATGTTGACATTCTGATA
GGGATCATTGGATGCCAATGCAAAGAACATGAGAGTGTGGTCTGCATTCA
AGTATCCTGGTCGTAAGCTGTGGCCATGGGCGCTGCGGTCAAGGTCAATC
GCGATGACTAATCAGTCTCGGTGACTCTGGGGCGGTAGAGGCAGTGTCGT
GAACCAAAGCTTGAGCCGAGGGCAAAAACAACGGCGCATCAAACAATCAA
CGAAAGCATCGTCAACAGTGTCTCTTCCCAGTCAATTACTTCGCAAAACC
TTCTCGATAGAACCCTTCAGACGATGAACAGGCCACGCAACCGTCAGCCG
CGCCCCCCAGGACAGACTCAGCGCCCGGGAGGCAGATCGTCACACCTTGG
TCGACGAGCTC
```

Example 2

Enzyme Expression Comparison: Quad Deleted Strain vs. MAD6 Strain

1. Preparation of the Vectors

Figure 9:
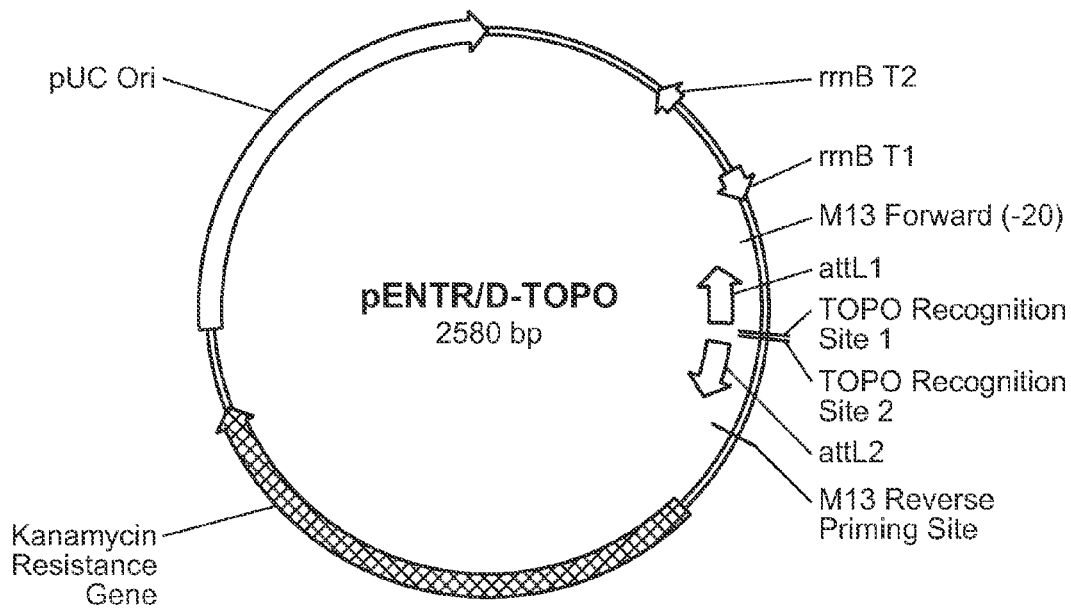
FIG. 9 illustrates the pENTR/D-TOPO vector, as described in Example 2.

Two glycosyl hydrolase family 43 proteins were expressed in the *T. reesei* strains, Archy3 and the quad deleted strain. The genes, fv43B and fv43C, were cloned from *Fusarium verticillioides* genomic DNA and assembled into expression vector pTrex3gM using the Gateway® cloning system (Invitrogen). Both genes were initially cloned into the pENTR/D-TOPO vector (Invitrogen), as depicted in FIG. 9.

Figure 10:
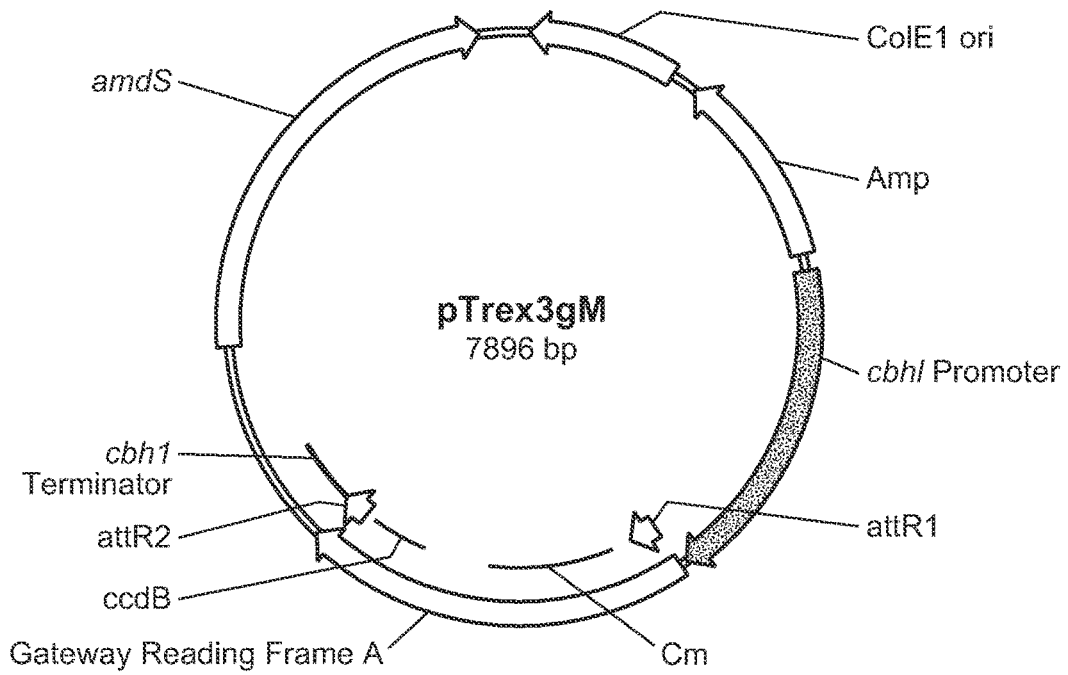
FIG. 10 illustrates the pTrex3gM vector, as described in Example 2.

The genes were subsequently recombined into vector pTrex3gM, in which the cbh1 promoter is upstream of the coding sequence of the gene of interest, and the cbh1 terminator is downstream of the stop codon of the gene of interest. The vector additionally contains the *Aspergillus nidulans* acetamidase (amdS) selectable marker to the 3' of the cbh1 terminator. The vector is depicted in FIG. 10.

Figure 11:
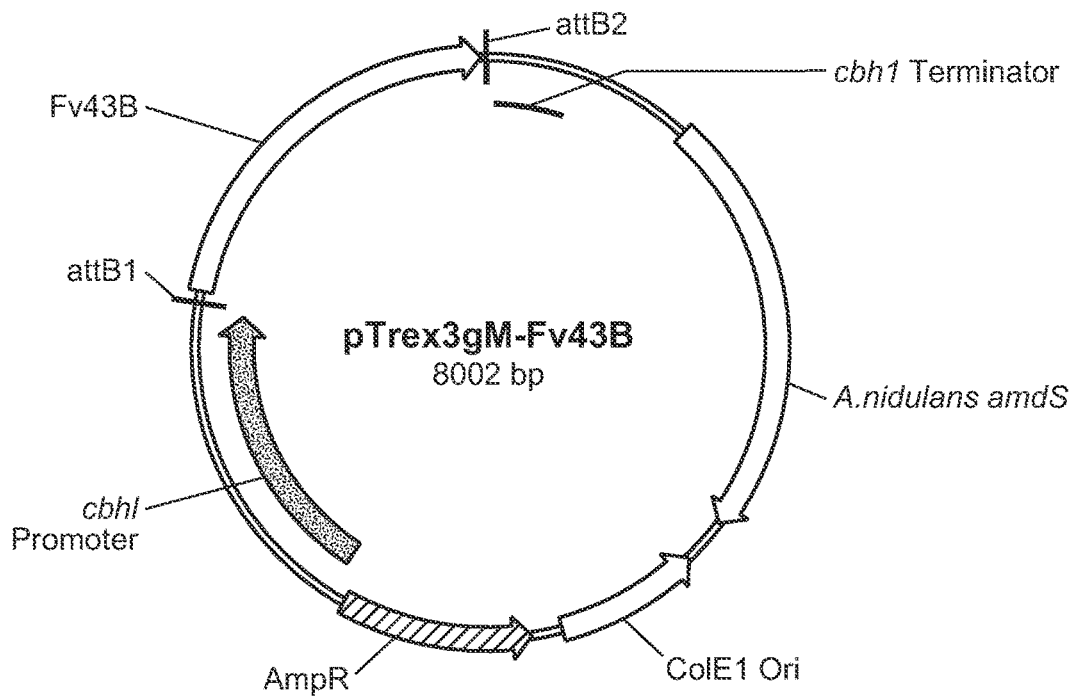
FIG. 11 illustrates the Fv43B expression vector, pTrex3gM-Fv43B, as described in Example 2.

The resulting Fv43B expression vector, pTrex3gM-Fv43B, is shown schematically in FIG. 11.

The full nucleotide sequence of the Fv43B glycosyl hydrolase in expression vector pTrex3gM is provided below as SEQ ID NO: 14.

```
TTGTACAAAGTGGTGATCGCGCCGCGCGCCAGCTCCGTGCGAAAGCCTGA
CGCACCGGTAGATTCTTGGTGAGCCCGTATCATGACGGCGGCGGGAGCTA
CATGGCCCCGGGTGATTTATTTTTTTTGTATCTACTTCTGACCCTTTTCA
AATATACGGTCAACTCATCTTTCACTGGAGATGCGGCCTGCTTGGTATTG
CGATGTTGTCAGCTTGGCAAATTGTGGCTTTCGAAAACACAAAACGATTC
CTTAGTAGCCATGCATTTTAAGATAACGGAATAGAAGAAAGAGGAAATTA
AAAAAAAAAAAAAAACAACATCCCGTTCATAACCCGTAGAATCGCCGCT
CTTCGTGTATCCCAGTACCAGTTTATTTTGAATAGCTCGCCCGCTGGAGA
GCATCCTGAATGCAAGTAACAACCGTAGAGGCTGACACGGCAGGTGTTGC
TAGGGAGCGTCGTGTTCTACAAGGCCAGACGTCTTCGCGGTTGATATATA
TGTATGTTTGACTGCAGGCTGCTCAGCGACGACAGTCAAGTTCGCCCTCG
CTGCTTGTGCAATAATCGCAGTGGGGAAGCCACACCGTGACTCCCATCTT
TCAGTAAAGCTCTGTTGGTGTTTATCAGCAATACACGTAATTTAAACTCG
TTAGCATGGGGCTGATAGCTTAATTACCGTTTACCAGTGCCATGGTTCTG
CAGCTTTCCTTGGCCCGTAAAATTCGGCGAAGCCAGCCAATCACCAGCTA
GGCACCAGCTAAACCCTATAATTAGTCTCTTATCAACACCATCCGCTCCC
CCGGGATCAATGAGGAGAATGAGGGGGATGCGGGGCTAAAGAAGCCTACA
TAACCCTCATGCCAACTCCCAGTTTACACTCGTCGAGCCAACATCCTGAC
TATAAGCTAACACAGAATGCCTCAATCCTGGGAAGAACTGGCCGCTGATA
AGCGCGCCCGCCTCGCAAAAACCATCCCTGATGAATGGAAAGTCCAGACG
CTGCCTGCGGAAGACAGCGTTATTGATTTCCCAAAGAAATCGGGGATCCT
TTCAGAGGCCGAACTGAAGATCACAGAGGCCTCCGCTGCAGATCTTGTGT
CCAAGCTGGCGGCCGGAGAGTTGACCTCGGTGGAAGTTACGCTAGCATTC
TGTAAACGGGCAGCAATCGCCCAGCAGTTAGTAGGGTCCCCTCTACCTCT
```

CAGGGAGATGTAACAACGCCACCTTATGGGACTATCAAGCTGACGCTGGC
TTCTGTGCAGACAAACTGCGCCCACGAGTTCTTCCCTGACGCCGCTCTCG
CGCAGGCAAGGGAACTCGATGAATACTACGCAAAGCACAAGAGACCCGTT
GGTCCACTCCATGGCCTCCCCATCTCTCTCAAAGACCAGCTTCGAGTCAA
GGTACACCGTTGCCCCTAAGTCGTTAGATGTCCCTTTTTGTCAGCTAACA
TATGCCACCAGGGCTACGAAACATCAATGGGCTACATCTCATGGCTAAAC
AAGTACGACGAAGGGGACTCGGTTCTGACAACCATGCTCCGCAAAGCCGG
TGCCGTCTTCTACGTCAAGACCTCTGTCCCGCAGACCCTGATGGTCTGCG
AGACAGTCAACAACATCATCGGGCGCACCGTCAACCCACGCAACAAGAAC
TGGTCGTGCGGCGGCAGTTCTGGTGGTGAGGGTGCGATCGTTGGGATTCG
TGGTGGCGTCATCGGTGTAGGAACGGATATCGGTGGCTCGATTCGAGTGC
CGGCCGCGTTCAACTTCCTGTACGGTCTAAGGCCGAGTCATGGGCGGCTG
CCGTATGCAAAGATGGCGAACAGCATGGAGGGTCAGGAGACGGTGCACAG
CGTTGTCGGGCCGATTACGCACTCTGTTGAGGGTGAGTCCTTCGCCCTCTT
CCTTCTTTTCCTGCTCTATACCAGGCCTCCACTGTCCTCCTTTCTTGCTT
TTTATACTATATACGAGACCGGCAGTCACTGATGAAGTATGTTAGACCTC
CGCCTCTTCACCAAATCCGTCCTCGGTCAGGAGCCATGGAAATACGACTC
CAAGGTCATCCCCATGCCCTGGCGCCAGTCCGAGTCGGACATTATTGCCT
CCAAGATCAAGAACGGCGGGCTCAATATCGGCTACTACAACTTCGACGGC
AATGTCCTTCCACACCCTCCTATCCTGCGCGGCGTGGAAACCACCGTCGC
CGCACTCGCCAAAGCCGGTCACACCGTGACCCCGTGGACGCCATACAAGC
ACGATTTCGGCCACGATCTCATCTCCCATATCTACGCGGCTGACGGCAGC
GCCGACGTAATGCGCGATATCAGTGCATCCGGCGAGCCGGCGATTCCAAA
TATCAAAGACCTACTGAACCCGAACATCAAAGCTGTTAACATGAACGAGC
TCTGGGACACGCATCTCCAGAAGTGGAATTACCAGATGGAGTACCTTGAG
AAATGGCGGAGGCTGAAGAAAAGGCCGGGAAGGAACTGGACGCCATCAT
CGCGCCGATTACGCCTACCGCTGCGGTACGGCATGACCAGTTCCGGTACT
ATGGGTATGCCTCTGTGATCAACCTGCTGGATTTCACGAGCGTGGTTGTT
CCGGTTACCTTTGCGGATAAGAACATCGATAAGAAGAATGAGAGTTTCAA
GGCGGTTAGTGAGCTTGATGCCCTCGTGCAGGAAGAGTATGATCCGGAGG
CGTACCATGGGCACCGGTTGCAGTGCAGGTTATCGGACGGAGACTCAGT
GAAGAGAGGACGTTGGCGATTGCAGAGGAAGTGGGGAAGTTGCTGGGAAA
TGTGGTGACTCCATAGCTAATAAGTGTCAGATAGCAATTTGCACAAGAAA
TCAATACCAGCAACTGTAAATAAGCGCTGAAGTGACCATGCCATGCTACG
AAAGAGCAGAAAAAACCTGCCGTAGAACCAAGAGATATGACACGCTTC
CATCTCTCAAAGGAAGAATCCCTTCAGGGTTGCGTTTCCAGTCTAGAGGC
CATTTAGGCCGTTGCTGGCGTTTTTCCATAGGCTCCGCCCCCCTGACGAG
CATCACAAAAATCGACGCTCAAGTCAGAGGTGGCGAAACCCGACAGGACT
ATAAAGATACCAGGCGTTTCCCCCTGGAAGCTCCCTCGTGCGCTCTCCTG
TTCCGACCCTGCCGCTTACCGGATACCTGTCCGCCTTTCTCCCTTCGGGA

AGCGTGGCGCTTTCTCATAGCTCACGCTGTAGGTATCTCAGTTCGGTGTA
GGTCGTTCGCTCCAAGCTGGGCTGTGTGCACGAACCCCCCGTTCAGCCCG
ACCGCTGCGCCTTATCCGGTAACTATCGTCTTGAGTCCAACCCGGTAAGA
CACGACTTATCGCCACTGGCAGCAGCCACTGGTAACAGGATTAGCAGAGC
GAGGTATGTAGGCGGTGCTACAGAGTTCTTGAAGTGGTGGCCTAACTACG
GCTACACTAGAAGGACAGTATTTGGTATCTGCGCTCTGCTGAAGCCAGTT
ACCTTCGGAAAAGAGTTGGTAGCTCTTGATCCGGCAAACAAACCACCGC
TGGTAGCGGTGGTTTTTTTGTTTGCAAGCAGCAGATTACGCGCAGAAAAA
AAGGATCTCAAGAAGATCCTTTGATCTTTTCTACGGGGTCTGACGCTCAG
TGGAACGAAAACTCACGTTAAGGCCTGCAGGGCCGATTTTGGTCATGAGA
TTATCAAAAAGGATCTTCACCTAGATCCTTTTAAATTAAAAATGAAGTTT
TAAATCAATCTAAAGTATATATGAGTAAACTTGGTCTGACAGTTACCAAT
GCTTAATCAGTGAGGCACCTATCTCAGCGATCTGTCTATTTCGTTCATCC
ATAGTTGCCTGACTCCCCGTCGTGTAGATAACTACGATACGGGAGGGCTT
ACCATCTGGCCCCAGTGCTGCAATGATACCGCGAGACCCACGCTCACCGG
CTCCAGATTTATCAGCAATAAACCAGCCAGCCGGAAGGGCCGAGCGCAGA
AGTGGTCCTGCAACTTTATCCGCCTCCATCCAGTCTATTAATTGTTGCCG
GGAAGCTAGAGTAAGTAGTTCGCCAGTTAATAGTTTGCGCAACGTTGTTG
CCATTGCTACAGGCATCGTGGTGTCACGCTCGTCGTTTGGTATGGCTTCA
TTCAGCTCCGGTTCCCAACGATCAAGGCGAGTTACATGATCCCCCATGTT
GTGCAAAAAAGCGGTTAGCTCCTTCGGTCCTCCGATCGTTGTCAGAAGTA
AGTTGGCCGCAGTGTTATCACTCATGGTTATGGCAGCACTGCATAATTCT
CTTACTGTCATGCCATCCGTAAGATGCTTTTCTGTGACTGGTGAGTACTC
AACCAAGTCATTCTGAGAATAGTGTATGCGGCGACCGAGTTGCTCTTGCC
CGGCGTCAATACGGGATAATACCGCGCCACATAGCAGAACTTTAAAAGTG
CTCATCATTGGAAAACGTTCTTCGGGGCGAAAACTCTCAAGGATCTTACC
GCTGTTGAGATCCAGTTCGATGTAACCCACTCGTGCACCCAACTGATCTT
CAGCATCTTTTACTTTCACCAGCGTTTCTGGGTGAGCAAAAACAGGAAGG
CAAAATGCCGCAAAAAAGGGAATAAGGGCGACACGGAAATGTTGAATACT
CATACTCTTCCTTTTTCAATATTATTGAAGCATTTATCAGGGTTATTGTC
TCATGAGCCATTTAGGCCTCTAGAGTTGTGAAGTCGGTAATCCCGCTGTAT
AGTAATACGAGTCGCATCTAAATACTCCGAAGCTGCTGCGAACCCGGAGA
ATCGAGATGTGCTGGAAAGCTTCTAGCGAGCGGCTAAATTAGCATGAAAG
GCTATGAGAAATTCTGGAGACGGCTTGTTGAATCATGGCGTTCCATTCTT
CGACAAGCAAAGCGTTCCGTCGCAGTAGCAGGCACTCATTCCCGAAAAAA
CTCGGAGATTCCTAAGTAGCGATGGAACCGGAATAATATAATAGGCAATA
CATTGAGTTGCCTCGACGGTTGCAATGCAGGGGTACTGAGCTTGGACATA
ACTGTTCCGTACCCCACCTCTTCTCAACCTTTGGCGTTTCCCTGATTCAG
CGTACCCGTACAAGTCGTAATCACTATTAACCCAGACTGACCGGACGTGT
TTTGCCCTTCATTTGGAGAAATAATGTCATTGCGATGTGTAATTTGCCTG
CTTGACCGACTGGGGCTGTTCGAAGCCCGAATGTAGGATTGTTATCCGAA

```
CTCTGCTCGTAGAGGCATGTTGTGAATCTGTGTCGGGCAGGACACGCCTC
GAAGGTTCACGGCAAGGGAAACCACCGATAGCAGTGTCTAGTAGCAACCT
GTAAAGCCGCAATGCAGCATCACTGGAAAATACAAACCAATGGCTAAAAG
TACATAAGTTAATGCCTAAAGAAGTCATATACCAGCGGCTAATAATTGTA
CAATCAAGTGGCTAAACGTACCGTAATTTGCCAACGGCTTGTGGGGTTGC
AGAAGCAACGGCAAAGCCCCACTTCCCCACGTTTGTTTCTTCACTCAGTC
CAATCTCAGCTGGTGATCCCCCAATTGGGTCGCTTGTTTGTTCCGGTGAA
GTGAAAGAAGACAGAGGTAAGAATGTCTGACTCGGAGCGTTTTGCATACA
ACCAAGGGCAGTGATGGAAGACAGTGAAATGTTGACATTCAAGGAGTATT
TAGCCAGGGATGCTTGAGTGTATCGTGTAAGGAGGTTTGTCTGCCGATAC
GACGAATACTGTATAGTCACTTCTGATGAAGTGGTCCATATTGAAATGTA
AAGTCGGCACTGAACAGGCAAAAGATTGAGTTGAAACTGCCTAAGATCTC
GGGCCCTCGGGCCTTCGGCCTTTGGGTGTACATGTTTGTGCTCCGGGCAA
ATGCAAAGTGTGGTAGGATCGAACACACTGCTGCCTTTACCAAGCAGCTG
AGGGTATGTGATAGGCAAATGTTCAGGGGCCACTGCATGGTTTCGAATAG
AAAGAGAAGCTTAGCCAAGAACAATAGCCGATAAAGATAGCCTCATTAAA
CGGAATGAGCTAGTAGGCAAAGTCAGCGAATGTGTATATATAAAGGTTCG
AGGTCCGTGCCTCCCTCATGCTCTCCCCATCTACTCATCAACTCAGATCC
TCCAGGAGACTTGTACACCATCTTTTGAGGCACAGAAACCCAATAGTCAA
CCATCACAAGTTTGTACAAAAAAGCAGGCTCCGCGGCCGCCCCCTTCACC
ATGCGCTTCTCTTGGCTATTGTGCCCCTTCTAGCGATGGGAAGTGCTCT
TCCTGAAACGAAGACGGATGTTTCGACATACACCAACCCTGTCCTTCCAG
GATGGCACTCGGATCCATCGTGTATCCAGAAAGATGGCCTCTTTCTCTGC
GTCACTTCAACATTCATCTCCTTCCCAGGTCTTCCCGTCTATGCCTCAAG
GGATCTAGTCAACTGGCGTCTCATCAGCCATGTCTGGAACCGCGAGAAAC
AGTTGCCTGGCATTAGCTGGAAGACGGCAGGACAGCAACAGGGAATGTAT
GCACCAACCATTCGATACCACAAGGGAACATACTACGTCATCTGCGAATA
CCTGGGCGTTGGAGATATTATTGGTGTCATCTTCAAGACCACCAATCCGT
GGGACGAGAGTAGCTGGAGTGACCCTGTTACCTTCAAGCCAAATCACATC
GACCCCGATCTGTTCTGGGATGATGACGGAAAGGTTTATTGTGCTACCCA
TGGCATCACTCTGCAGGAGATTGATTTGGAAACTGGAGAGCTTAGCCCGG
AGCTTAATATCTGGAACGGCACAGGAGGTGTATGGCCTGAGGGTCCCCAT
ATCTACAAGCGCGACGTTACTACTATCTCATGATTGCCGAGGGTGGAAC
TGCCGAAGACCACGCTATCACAATCGCTCGGGCCCGCAAGATCACCGGCC
CCTATGAAGCCTACAATAACAACCCAATCTTGACCAACCGCGGGACATCT
GAGTACTTCCAGACTGTCGGTCACGGTGATCTGTTCCAAGATACCAAGGG
CAACTGGTGGGGTCTTTGTCTTGCTACTCGCATCACAGCACAGGGAGTTT
CACCCATGGGCCGTGAAGCTGTTTTGTTCAATGGCACATGGAACAAGGGC
GAATGGCCCAAGTTGCAACCAGTACGAGGTCGCATGCCTGGAAACCTCCT
CCCAAAGCCGACGCGAAACGTTCCCGGAGATGGGCCCTTCAACGCTGACC
CAGACAACTACAACTTGAAGAAGACTAAGAAGATCCCTCCTCACTTTGTG
CACCATAGAGTCCCAAGAGACGGTGCCTTCTCTTTGTCTTCCAAGGGTCT
GCACATCGTGCCTAGTCGAAACAACGTTACCGGTAGTGTGTTGCCAGGAG
ATGAGATTGAGCTATCAGGACAGCGAGGTCTAGCTTTCATCGGACGCCGC
CAAACTCACACTCTGTTCAAATATAGTGTTGATATCGACTTCAAGCCCAA
GTCCGATGATCAGGAAGCTGGAATCACCGTTTTCCGCACGCAGTTCGACC
ATATCGATCTTGGCATTGTTCGTCTTCCTACAAACCAAGGCAGCAACAAG
AAATCTAAGCTTGCCTTCCGATTCCGGGCCACAGGAGCTCAGAATGTTCC
TGCACCGAAGGTAGTACCGGTCCCCGATGGCTGGGAGAAGGGCGTAATCA
GTCTACATATCGAGGCAGCCAACGCGACGCACTACAACCTTGGAGCTTCG
AGCCACAGAGGCAAGACTCTCGACATCGCGACAGCATCAGCAAGTCTTGT
GAGTGGAGGCACGGGTTCATTTGTTGGTAGTTTGCTTGGACCTTATGCTA
CCTGCAACGGCAAAGGATCTGGAGTGGAATGTCCCAAGGGAGGTGATGTC
TATGTGACCCAATGGACTTATAAGCCCGTGGCACAAGAGATTGATCATGG
TGTTTTTGTGAAATCAGAATTGTAGAAGGGTGGGCGCGCCGACCCAGCTT
TC
```

Figure 12:
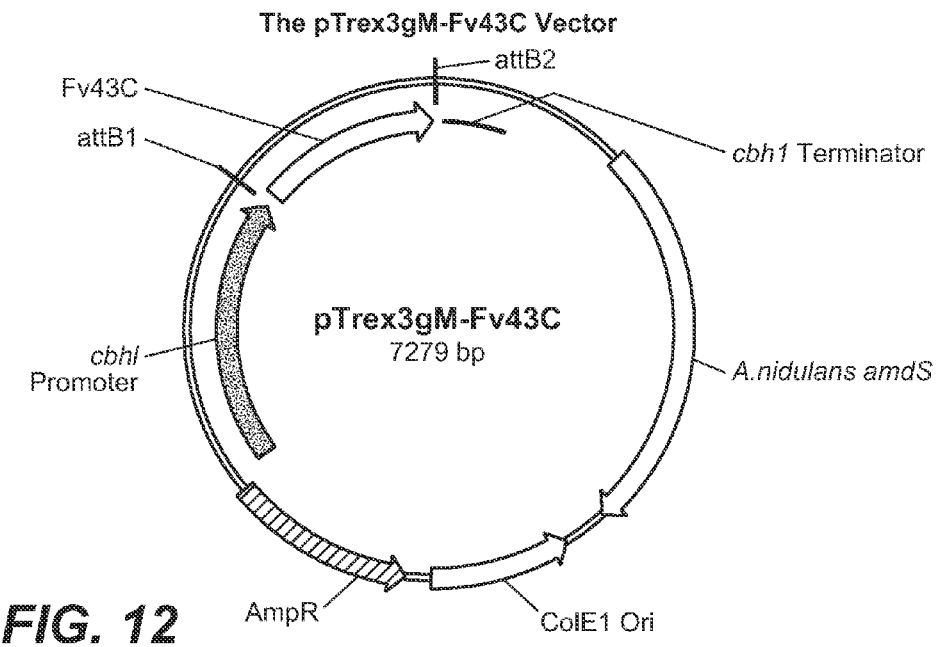
FIG. 12 illustrates the Fv43C expression vector, pTrex3gM-Fv43C, as described in Example 2.

The resulting Fv43C expression vector, pTrex3gM-Fv43C, is shown schematically as FIG. 12.

The full nucleotide sequence of the Fv43C glycosyl hydrolase in expression vector pTrex3gM is provided below as SEQ ID NO:15.

```
TTGTACAAAGTGGTGATCGCGCCGCGCGCCAGCTCCGTGCGAAAGCCTGA
CGCACCGGTAGATTCTTGGTGAGCCCGTATCATGACGGCGGCGGGAGCTA
CATGGCCCCGGGTGATTTATTTTTTTTGTATCTACTTCTGACCCTTTTCA
AATATACGGTCAACTCATCTTTCACTGGAGATGCGGCCTGCTTGGTATTG
CGATGTTGTCAGCTTGGCAAATTGTGGCTTTCGAAAACACAAAACGATTC
CTTAGTAGCCATGCATTTTAAGATAACGGAATAGAAGAAAGAGGAAATTA
AAAAAAAAAAAAAAACAACATCCCGTTCATAACCCGTAGAATCGCCGCT
CTTCGTGTATCCCAGTACCAGTTTATTTTGAATAGCTCGCCCGCTGGAGA
GCATCCTGAATGCAAGTAACAACCGTAGAGGCTGACACGGCAGGTGTTGC
TAGGGAGCGTCGTGTTCTACAAGGCCAGACGTCTTCGCGGTTGATATATA
TGTATGTTTGACTGCAGGCTGCTCAGCGACGACAGTCAAGTTCGCCCTCG
CTGCTTGTGCAATAATCGCAGTGGGGAAGCCACACCGTGACTCCCATCTT
TCAGTAAAGCTCTGTTGGTGTTTATCAGCAATACACGTAATTTAAACTCG
TTAGCATGGGCTGATAGCTTAATTACCGTTTACCAGTGCCATGGTTCTG
CAGCTTTCCTTGGCCCGTAAAATTCGGCGAAGCCAGCCAATCACCAGCTA
GGCACCAGCTAAACCCTATAATTAGTCTCTTATCAACACCATCCGCTCCC
CCGGGATCAATGAGGAGAATGAGGGGGATGCGGGGCTAAAGAAGCCTACA
TAACCCTCATGCCAACTCCCAGTTTACACTCGTCGAGCCAACATCCTGAC
TATAAGCTAACACAGAATGCCTCAATCCTGGGAAGAACTGGCCGCTGATA
AGCGCGCCCGCCTCGCAAAAACCATCCCTGATGAATGGAAAGTCCAGACG
```

-continued

CTGCCTGCGGAAGACAGCGTTATTGATTTCCCAAAGAAATCGGGGATCCT
TTCAGAGGCCGAACTGAAGATCACAGAGGCCTCCGCTGCAGATCTTGTGT
CCAAGCTGGCGGCCGGAGAGTTGACCTCGGTGGAAGTTACGCTAGCATTC
TGTAAACGGGCAGCAATCGCCCAGCAGTTAGTAGGGTCCCCTCTACCTCT
CAGGGAGATGTAACAACGCCACCTTATGGGACTATCAAGCTGACGCTGGC
TTCTGTGCAGACAAACTGCGCCCACGAGTTCTTCCCTGACGCCGCTCTCG
CGCAGGCAAGGGAACTCGATGAATACTACGCAAAGCACAAGAGACCCGTT
GGTCCACTCCATGGCCTCCCCATCTCTCTCAAAGACCAGCTTCGAGTCAA
GGTACACCGTTGCCCCTAAGTCGTTAGATGTCCCTTTTTGTCAGCTAACA
TATGCCACCAGGGCTACGAAACATCAATGGGCTACATCTCATGGCTAAAC
AAGTACGACGAAGGGGACTCGGTTCTGACAACCATGCTCCGCAAAGCCGG
TGCCGTCTTCTACGTCAAGACCTCTGTCCCGCAGACCCTGATGGTCTGCG
AGACAGTCAACAACATCATCGGGCGCACCGTCAACCCACGCAACAAGAAC
TGGTCGTGCGGCGGCAGTTCTGGTGGTGAGGGTGCGATCGTTGGGATTCG
TGGTGGCGTCATCGGTGTAGGAACGGATATCGGTGGCTCGATTCGAGTGC
CGGCCGCGTTCAACTTCCTGTACGGTCTAAGGCCGAGTCATGGGCGGCTG
CCGTATGCAAAGATGGCGAACAGCATGGAGGGTCAGGAGACGGTGCACAG
CGTTGTCGGGCCGATTACGCACTCTGTTGAGGGTGAGTCCTTCGCCTCTT
CCTTCTTTTCCTGCTCTATACCAGGCCTCCACTGTCCTCCTTTCTTGCTT
TTTATACTATATACGAGACCGGCAGTCACTGATGAAGTATGTTAGACCTC
CGCCTCTTCACCAAATCCGTCCTCGGTCAGGAGCCATGGAAATACGACTC
CAAGGTCATCCCCATGCCCTGGCGCCAGTCCGAGTCGGACATTATTGCCT
CCAAGATCAAGAACGGCGGGCTCAATATCGGCTACTACAACTTCGACGGC
AATGTCCTTCCACACCCTCCTATCCTGCGCGGCGTGGAAACCACCGTCGC
CGCACTCGCCAAAGCCGGTCACACCGTGACCCCGTGGACGCCATACAAGC
ACGATTTCGGCCACGATCTCATCTCCCATATCTACGCGGCTGACGGCAGC
GCCGACGTAATGCGCGATATCAGTGCATCCGGCGAGCCGGCGATTCCAAA
TATCAAAGACCTACTGAACCCGAACATCAAAGCTGTTAACATGAACGAGC
TCTGGGACACGCATCTCCAGAAGTGGAATTACCAGATGGAGTACCTTGAG
AAATGGCGGGAGGCTGAAGAAAAGGCCGGGAAGGAACTGGACGCCATCAT
CGCGCCGATTACGCCTACCGCTGCGGTACGGCATGACCAGTTCCGGTACT
ATGGGTATGCCTCTGTGATCAACCTGCTGGATTTCACGAGCGTGGTTGTT
CCGGTTACCTTTGCGGATAAGAACATCGATAAGAAGAATGAGAGTTTCAA
GGCGGTTAGTGAGCTTGATGCCCTCGTGCAGGAAGAGTATGATCCGGAGG
CGTACCATGGGCACCGGTTGCAGTGCAGGTTATCGGACGGAGACTCAGT
GAAGAGAGGACGTTGGCGATTGCAGAGGAAGTGGGGAAGTTGCTGGGAAA
TGTGGTGACTCCATAGCTAATAAGTGTCAGATAGCAATTTGCACAAGAAA
TCAATACCAGCAACTGTAAATAAGCGCTGAAGTGACCATGCCATGCTACG
AAAGAGCAGAAAAAACCTGCCGTAGAACCGAAGAGATATGACACGCTTC
CATCTCTCAAAGGAAGAATCCCTTCAGGGTTGCGTTTCCAGTCTAGAGGC
CATTTAGGCCGTTGCTGGCGTTTTTCCATAGGCTCCGCCCCCCTGACGAG

CATCACAAAAATCGACGCTCAAGTCAGAGGTGGCGAAACCCGACAGGACT
ATAAAGATACCAGGCGTTTCCCCCTGGAAGCTCCCTCGTGCGCTCTCCTG
TTCCGACCCTGCCGCTTACCGGATACCTGTCCGCCTTTCTCCCTTCGGGA
AGCGTGGCGCTTTCTCATAGCTCACGCTGTAGGTATCTCAGTTCGGTGTA
GGTCGTTCGCTCCAAGCTGGGCTGTGTGCACGAACCCCCCGTTCAGCCCG
ACCGCTGCGCCTTATCCGGTAACTATCGTCTTGAGTCCAACCCGGTAAGA
CACGACTTATCGCCACTGGCAGCAGCCACTGGTAACAGGATTAGCAGAGC
GAGGTATGTAGGCGGTGCTACAGAGTTCTTGAAGTGGTGGCCTAACTACG
GCTACACTAGAAGGACAGTATTTGGTATCTGCGCTCTGCTGAAGCCAGTT
ACCTTCGGAAAAGAGTTGGTAGCTCTTGATCCGGCAAACAAACCACCGC
TGGTAGCGGTGGTTTTTTTGTTTGCAAGCAGCAGATTACGCGCAGAAAAA
AAGGATCTCAAGAAGATCCTTTGATCTTTTCTACGGGGTCTGACGCTCAG
TGGAACGAAAACTCACGTTAAGGCCTGCAGGGCCGATTTTGGTCATGAGA
TTATCAAAAAGGATCTTCACCTAGATCCTTTTAAATTAAAAATGAAGTTT
TAAATCAATCTAAAGTATATATGAGTAAACTTGGTCTGACAGTTACCAAT
GCTTAATCAGTGAGGCACCTATCTCAGCGATCTGTCTATTTCGTTCATCC
ATAGTTGCCTGACTCCCCGTCGTGTAGATAACTACGATACGGGAGGGCTT
ACCATCTGGCCCCAGTGCTGCAATGATACCGCGAGACCCACGCTCACCGG
CTCCAGATTTATCAGCAATAAACCAGCCAGCCGGAAGGGCCGAGCGCAGA
AGTGGTCCTGCAACTTTATCCGCCTCCATCCAGTCTATTAATTGTTGCCG
GGAAGCTAGAGTAAGTAGTTCGCCAGTTAATAGTTTGCGCAACGTTGTTG
CCATTGCTACAGGCATCGTGGTGTCACGCTCGTCGTTTGGTATGGCTTCA
TTCAGCTCCGGTTCCCAACGATCAAGGCGAGTTACATGATCCCCCATGTT
GTGCAAAAAAGCGGTTAGCTCCTTCGGTCCTCCGATCGTTGTCAGAAGTA
AGTTGGCCGCAGTGTTATCACTCATGGTTATGGCAGCACTGCATAATTCT
CTTACTGTCATGCCATCCGTAAGATGCTTTTCTGTGACTGGTGAGTACTC
AACCAAGTCATTCTGAGAATAGTGTATGCGGCGACCGAGTTGCTCTTGCC
CGGCGTCAATACGGGATAATACCGCGCCACATAGCAGAACTTTAAAAGTG
CTCATCATTGGAAAACGTTCTTCGGGGCGAAAACTCTCAAGGATCTTACC
GCTGTTGAGATCCAGTTCGATGTAACCCACTCGTGCACCCAACTGATCTT
CAGCATCTTTTACTTTCACCAGCGTTTCTGGGTGAGCAAAAACAGGAAGG
CAAAATGCCGCAAAAAAGGGAATAAGGGCGACACGGAAATGTTGAATACT
CATACTCTTCCTTTTTCAATATTATTGAAGCATTTATCAGGGTTATTGTC
TCATGAGCCATTTAGGCCTCTAGAGTTGTGAAGTCGGTAATCCCGCTGTAT
AGTAATACGAGTCGCATCTAAATACTCCGAAGCTGCTGCGAACCCGGAGA
ATCGAGATGTGCTGGAAAGCTTCTAGCGAGCGGCTAAATTAGCATGAAAG
GCTATGAGAAATTCTGGAGACGGCTTGTTGAATCATGGCGTTCCATTCTT
CGACAAGCAAAGCGTTCCGTCGCAGTAGCAGGCACTCATTCCCGAAAAAA
CTCGGAGATTCCTAAGTAGCGATGGAACCGGAATAATATAATAGGCAATA
CATTGAGTTGCCTCGACGGTTGCAATGCAGGGGTACTGAGCTTGGACATA

ACTGTTCCGTACCCCACCTCTTCTCAACCTTTGGCGTTTCCCTGATTCAG

CGTACCCGTACAAGTCGTAATCACTATTAACCCAGACTGACCGGACGTGT

TTTGCCCTTCATTTGGAGAAATAATGTCATTGCGATGTGTAATTTGCCTG

CTTGACCGACTGGGGCTGTTCGAAGCCCGAATGTAGGATTGTTATCCGAA

CTCTGCTCGTAGAGGCATGTTGTGAATCTGTGTCGGGCAGGACACGCCTC

GAAGGTTCACGGCAAGGGAAACCACCGATAGCAGTGTCTAGTAGCAACCT

GTAAAGCCGCAATGCAGCATCACTGGAAAATACAAACCAATGGCTAAAAG

TACATAAGTTAATGCCTAAAGAAGTCATATACCAGCGGCTAATAATTGTA

CAATCAAGTGGCTAAACGTACCGTAATTTGCCAACGGCTTGTGGGGTTGC

AGAAGCAACGGCAAAGCCCCACTTCCCCACGTTTGTTTCTTCACTCAGTC

CAATCTCAGCTGGTGATCCCCAATTGGGTCGCTTGTTTGTTCCGGTGAA

GTGAAAGAAGACAGAGGTAAGAATGTCTGACTCGGAGCGTTTTGCATACA

ACCAAGGGCAGTGATGGAAGACAGTGAAATGTTGACATTCAAGGAGTATT

TAGCCAGGGATGCTTGAGTGTATCGTGTAAGGAGGTTTGTCTGCCGATAC

GACGAATACTGTATAGTCACTTCTGATGAAGTGGTCCATATTGAAATGTA

AAGTCGGCACTGAACAGGCAAAAGATTGAGTTGAAACTGCCTAAGATCTC

GGGCCCTCGGGCCTTCGGCCTTTGGGTGTACATGTTTGTGCTCCGGGCAA

ATGCAAAGTGTGGTAGGATCGAACACACTGCTGCCTTTACCAAGCAGCTG

AGGGTATGTGATAGGCAAATGTTCAGGGGCCACTGCATGGTTTCGAATAG

AAAGAGAAGCTTAGCCAAGAACAATAGCCGATAAAGATAGCCTCATTAAA

CGGAATGAGCTAGTAGGCAAAGTCAGCGAATGTGTATATATAAAGGTTCG

AGGTCCGTGCCTCCCTCATGCTCTCCCCATCTACTCATCAACTCAGATCC

TCCAGGAGACTTGTACACCATCTTTTGAGGCACAGAAACCCAATAGTCAA

CCATCACAAGTTTGTACAAAAAAGCAGGCTCCGCGGCCGCCCCCTTCACC

ATGCGTCTTCTATCGTTTCCCAGCCATCTCCTCGTGGCCTTCCTAACCCT

CAAAGAGGCTTCATCCCTCGCCCTCAGCAAACGGGATAGCCCTGTCCTCC

CCGGCCTCTGGGCGGACCCCAACATCGCCATCGTCGACAAGACATACTAC

ATCTTCCCTACCACCGACGGTTTCGAAGGCTGGGGCGGCAACGTCTTCTA

CTGGTGGAAATCAAAAGATCTCGTATCATGGACAAAGAGCGACAAGCCAT

TCCTTACTCTCAATGGTACGAATGGCAACGTTCCTGGGCTACAGGTAAT

GCCTGGGCTCCTGCTTTCGCTGCTCGCGGAGGCAAGTATTACTTCTACCA

TAGTGGGAATAATCCCTCTGTGAGTGATGGGCATAAGAGTATTGGTGCGG

CGGTGGCTGATCATCCTGAGGGGCCGTGGAAGGCACAGGATAAGCCGATG

ATCAAGGGAACTTCTGATGAGGAGATTGTCAGCAACCAGGCTATCGATCC

CGCTGCCTTTGAAGACCCTGAGACTGGAAAGTGGTATATCTACTGGGGAA

ACGGTGTCCCCATTGTCGCAGAGCTCAACGACGACATGGTCTCTCTCAAA

GCAGGCTGGCACAAAATCACAGGTCTTCAGAATTTCCGCGAGGGTCTTTT

CGTCAACTATCGCGATGGAACATATCATCTGACATACTCTATCGACGATA

CGGGCTCAGAGAACTATCGCGTTGGGTACGCTACGGCGGATAACCCCATT

GGACCTTGGACATATCGTGGTGTTCTTCTGGAGAAGGACGAATCGAAGGG

CATTCTTGCTACGGGACATAACTCCATCATCAACATTCCTGGAACGGATG

AGTGGTATATCGCGTATCATCGCTTCCATATTCCCGATGGAAATGGGTAT

AATAGGGAGACTACGATTGATAGGGTACCCATCGACAAGGATACGGGTTT

GTTTGGAAAGGTTACGCCGACTTTGCAGAGTGTTGATCCTAGGCCTTTGT

AGAAGGGTGGGCGCGCCGACCCAGCTTTC

The Nucleotide sequence for Fv43B, a GH43 family enzyme from *Fusarium verticillioldes* is provided below as SEQ ID NO: 16:

ATGCGCTTCTCTTGGCTATTGTGCCCCCTTCTAGCGATGGGAAGTGCTCT

TCCTGAAACGAAGACGGATGTTTCGACATACACCAACCCTGTCCTTCCAG

GATGGCACTCGGATCCATCGTGTATCCAGAAAGATGGCCTCTTTCTCTGC

GTCACTTCAACATTCATCTCCTTCCCAGGTCTTCCCGTCTATGCCTCAAG

GGATCTAGTCAACTGGCGTCTCATCAGCCATGTCTGGAACCGCGAGAAAC

AGTTGCCTGGCATTAGCTGGAAGACGGCAGGACAGCAACAGGGAATGTAT

GCACCAACCATTCGATACCACAAGGGAACATACTACGTCATCTGCGAATA

CCTGGGCGTTGGAGATATTATTGGTGTCATCTTCAAGACCACCAATCCGT

GGGACGAGAGTAGCTGGAGTGACCCTGTTACCTTCAAGCCAAATCACATC

GACCCCGATCTGTTCTGGGATGATGACGGAAAGGTTTATTGTGCTACCCA

TGGCATCACTCTGCAGGAGATTGATTTGGAAACTGGAGAGCTTAGCCCGG

AGCTTAATATCTGGAACGGCACAGGAGGTGTATGGCCTGAGGGTCCCCAT

ATCTACAAGCGCGACGGTTACTACTATCTCATGATTGCCGAGGGTGGAAC

TGCCGAAGACCACGCTATCACAATCGCTCGGGCCCGCAAGATCACCGGCC

CCTATGAAGCCTACAATAACAACCCAATCTTGACCAACCGCGGGACATCT

GAGTACTTCCAGACTGTCGGTCACGGTGATCTGTTCCAAGATACCAAGGG

CAACTGGTGGGGTCTTTGTCTTGCTACTCGCATCACAGCACAGGGAGTTT

CACCCATGGGCCGTGAAGCTGTTTTGTTCAATGGCACATGGAACAAGGGC

GAATGGCCCAAGTTGCAACCAGTACGAGGTCGCATGCCTGGAAACCTCCT

CCCAAAGCCGACGCGAAACGTTCCCGGAGATGGGCCCTTCAACGCTGACC

CAGACAACTACAACTTGAAGAAGACTAAGAAGATCCCTCCTCACTTTGTG

CACCATAGAGTCCCAAGAGACGGTGCCTTCTCTTTGTCTTCCAAGGGTCT

GCACATCGTGCCTAGTCGAAACAACGTTACCGGTAGTGTGTTGCCAGGAG

ATGAGATTGAGCTATCAGGACAGCGAGGTCTAGCTTTCATCGGACGCCGC

CAAACTCACACTCTGTTCAAATATAGTGTTGATATCGACTTCAAGCCCAA

GTCCGATGATCAGGAAGCTGGAATCACCGTTTTCCGCACGCAGTTCGACC

ATATCGATCTTGGCATTGTTCGTCTTCCTACAAACCAAGGCAGCAACAAG

AAATCTAAGCTTGCCTTCCGATTCCGGGCCACAGGAGCTCAGAATGTTCC

TGCACCGAAGGTAGTACCGGTCCCCGATGGCTGGGAGAAGGGCGTAATCA

GTCTACATATCGAGGCAGCCAACGCGACGCACTACAACCTTGGAGCTTCG

AGCCACAGAGGCAAGACTCTCGACATCGCGACAGCATCAGCAAGTCTTGT

GAGTGGAGGCACGGGTTCATTTGTTGGTAGTTTGCTTGGACCTTATGCTA

CCTGCAACGGCAAAGGATCTGGAGTGGAATGTCCCAAGGGAGGTGATGTC

-continued
TATGTGACCCAATGGACTTATAAGCCCGTGGCACAAGAGATTGATCATGG

TGTTTTTGTGAAATCAGAATTGTAG

The protein sequence of Fv43B is provided below as SEQ ID NO:17:

MRFSWLLCPLLAMGSALPETKTDVSTYTNPVLPGWHSDPSCIQKDGLFLC

VTSTFISFPGLPVYASRDLVNWRLISHVWNREKQLPGISWKTAGQQQGMY

APTIRYHKGTYYVICEYLGVGDIIGVIFKTTNPWDESSWSDPVTFKPNHI

DPDLFWDDDGKVYCATHGITLQEIDLETGELSPELNIWNGTGGVWPEGPH

IYKRDGYYYLMIAEGGTAEDHAITIARARKITGPYEAYNNNPILTNRGTS

EYFQTVGHGDLFQDTKGNWWGLCLATRITAQGVSPMGREAVLFNGTWNKG

EWPKLQPVRGRMPGNLLPKPTRNVPGDGPFNADPDNYNLKKTKKIPPHFV

HHRVPRDGAFSLSSKGLHIVPSRNNVTGSVLPGDEIELSGQRGLAFIGRR

QTHTLFKYSVDIDFKPKSDDQEAGITVFRTQFDHIDLGIVRLPTNQGSNK

KSKLAFRFRATGAQNVPAPKVVPVPDGWEKGVISLHIEAANATHYNLGAS

SHRGKTLDIATASASLVSGGTGSFVGSLLGPYATCNGKGSGVECPKGGDV

YVTQWTYKPVAQEIDHGVFVKSEL

The nucleotide sequence for Fv43C, a GH43 family enzyme from *Fusarium verticillioldes* is provided below as SEQ ID NO: 18:

ATGCGTCTTCTATCGTTTCCCAGCCATCTCCTCGTGGCCTTCCTAACCCT

CAAAGAGGCTTCATCCCTCGCCCTCAGCAAACGGGATAGCCCTGTCCTCC

CCGGCCTCTGGGCGGACCCCAACATCGCCATCGTCGACAAGACATACTAC

ATCTTCCCTACCACCGACGGTTTCGAAGGCTGGGGCGGCAACGTCTTCTA

CTGGTGGAAATCAAAAGATCTCGTATCATGGACAAAGAGCGACAAGCCAT

TCCTTACTCTCAATGGTACGAATGGCAACGTTCCCTGGGCTACAGGTAAT

GCCTGGGCTCCTGCTTTCGCTGCTCGCGGAGGCAAGTATTACTTCTACCA

TAGTGGGAATAATCCCTCTGTGAGTGATGGGCATAAGAGTATTGGTGCGG

CGGTGGCTGATCATCCTGAGGGGCCGTGGAAGGCACAGGATAAGCCGATG

ATCAAGGGAACTTCTGATGAGGAGATTGTCAGCAACCAGGCTATCGATCC

CGCTGCCTTTGAAGACCCTGAGACTGGAAAGTGGTATATCTACTGGGGAA

ACGGTGTCCCCATTGTCGCAGAGCTCAACGACGACATGGTCTCTCTCAAA

GCAGGCTGGCACAAAATCACAGGTCTTCAGAATTTCCGCGAGGGTCTTTT

CGTCAACTATCGCGATGGAACATATCATCTGACATACTCTATCGACGATA

CGGGCTCAGAGAACTATCGCGTTGGGTACGCTACGGCGGATAACCCCATT

GGACCTTGGACATATCGTGGTGTTCTTCTGGAGAAGGACGAATCGAAGGG

CATTCTTGCTACGGGACATAACTCCATCATCAACATTCCTGGAACGGATG

AGTGGTATATCGCGTATCATCGCTTCCATATTCCCGATGGAAATGGGTAT

AATAGGGAGACTACGATTGATAGGGTACCCATCGACAAGGATACGGGTTT

GTTTGGAAAGGTTACGCCGACTTTGCAGAGTGTTGATCCTAGGCCTTTGT

AG

The protein sequence for Fv43C is provided below as SEQ ID NO:19:

MRLLSFPSHLLVAFLTLKEASSLALSKRDSPVLPGLWADPNIAIVDKTYY

IFPTTDGFEGWGGNVFYWWKSKDLVSWTKSDKPFLTLNGTNGNVPWATGN

AWAPAFAARGGKYYFYHSGNNPSVSDGHKSIGAAVADHPEGPWKAQDKPM

IKGTSDEEIVSNQAIDPAAFEDPETGKWYIYWGNGVPIVAELNDDMVSLK

AGWHKITGLQNFREGLFVNYRDGTYHLTYSIDDTGSENYRVGYATADNPI

GPWTYRGVLLEKDESKGILATGHNSIINIPGTDEWYIAYHRFHIPDGNGY

NRETTIDRVPIDKDTGLFGKVTPTLQSVDPRPL

The pTrex3gM-Fv43B and pTrex3gM-Fv43C vectors were each independently transformed into the MAD6 strain by PEG mediated protoplast fusion and into the quad deleted strain by particle bombardment.

2. Transformation of thr Quad Deleted *T. reesei* Strain

The vector pTrex3gM-Fv43B and the vector pTrex3gM-Fv43C were transformed independently into the *T. reesei* quad deleted strain using biolistic particle bombardment by the PDS-1000/Helium System (Biorad, Hercules, Calif.) according to the manufacturer's instructions and as described in U.S. patent application publication US 2006/0003408, Example 2.

3. SDS-PAGE of *T. reesei* Quad Deleted Clones Transformed with Fv43B and Fv43C

Figure 13:
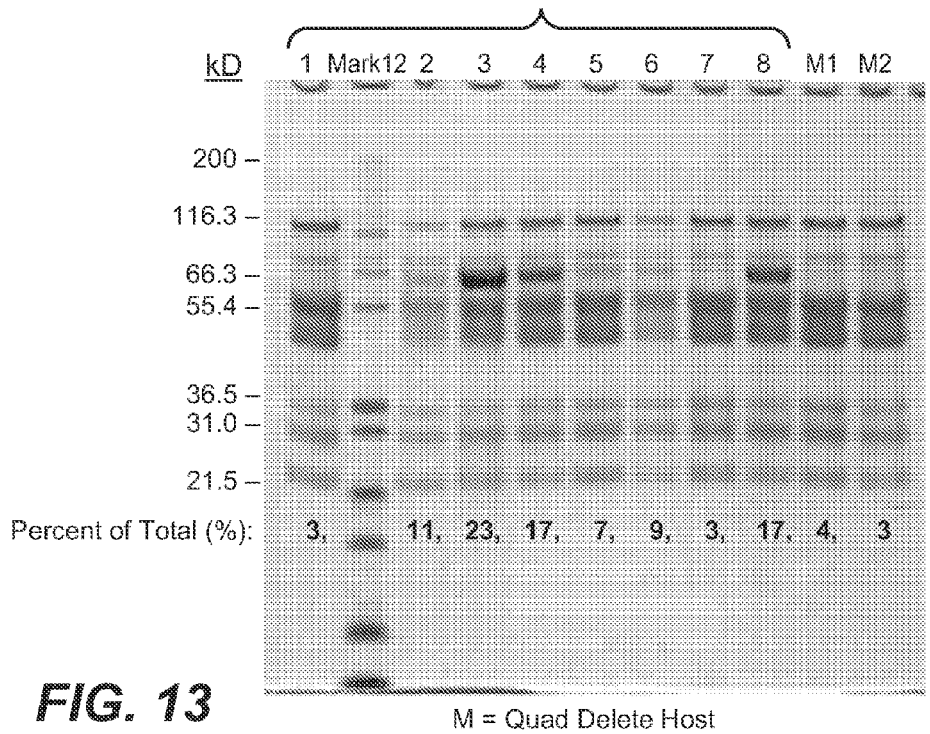
FIG. 13 is a picture of an SDS-PAGE characterizing Fv43B expressed using *T. reesei* quad deleted clones transformed with fv43B. The percent protein relative to the total proteins was quantitatively determined in accordance with Example 2, and listed below the corresponding lane.

Stable transformants were grown in 96-well microtiter plates as described in PCT publication WO 2011/038019. Culture supernatant was run on SDS-PAGE followed by coomassie blue staining with Simply Blue stain (Invitrogen). The gel was scanned and analyzed by densitometry. Image processing and band intensity quantitation was done using ImageJ (from National Institutes of Health) and by employing the Analyze Gel submenu function as described in the user guide, in subsection 27.13. The band corresponding to the Fv43B protein was quantified and reported as a percentage of the total protein. FIG. 13 provides a picture of the SDS-PAGE of proteins expressed from a *T. reesei* quad deleted clones transformed with fv43B.

The bands corresponding to the Fv43C protein were quantified and reported as a percentage of the total protein. Fv43C ran as two bands on the gel, representing different glycoforms, and these were summed in the densitometry analysis. The SDS-PAGE of proteins expressed from *T.reesei* quad deleted clones transformed with Fv43C is shown in FIG. 14.

4. PEG Mediated Protoplast Fusion Transformation of the M4D6 *T. reesei* Strain

The expression cassette portion of vectors pTrex3gM-Fv43B and pTrex3gM-Fv43C were each amplified, by PCR, using primers 1061F and 1085R to generate linear DNA fragments, 5.1 kb and 4.4 kb respectively, which were used for PEG mediated protoplast fusion transformation (see, e.g., Pentilla, M., et al. (1987) Gene 61(2):155-164) of the MAD6 strain.

1061F: 5'-GACCGGACGTGTTTTGCCCTTCAT-3' (SEQ ID NO:20)

1085R: 5'- GTGTGACCGGCTTTGGCGAGTG -3'(SEQ ID NO:21)

To make protoplasts, Lysing Enzymes from *Trichoderma harzianum* (Sigma catalog #L1412) were used at 10 mg/mL. After incubation with the transforming DNA and PEG, protoplasts were added to cooled molten sorbitol/acetamide agar with 0.5% uridine. The plates were incubated at 30° C.

After 24 hrs, an equal volume of the same media supplemented with 0.5% uridine and 1.2 g/L 5-fluoroorotic acid (FOA) was added to the plates in the form of an overlay. The plates were incubated at 30° C. for a week. The molten sorbitol/acetamide agar was prepared using the following recipe:

| Sorbitol/acetamide agar | |
|---|---|
| PART I | |
| Acetamide | 0.6 g |
| CsCl | 1.68 g |
| Glucose | 20 g |
| $KH_2PO_4$ | 6 g |
| $MgSO_4 \cdot 7H_2O$ | 0.6 g |
| $CaCl_2 \cdot 2H_2O$ | 0.6 g |
| 1000× Salts | 1 mL |
| Bring to 300 mL with milliQ $H_2O$ | |
| PART II | |
| Sorbitol | 218 g |
| Low Melting Point Agarose | 20 g |
| Bring Volume to | 700 mL |
| Autoclave Part I and Part II separately, then combine. | |
| 1000× Salts (per L) | |
| $FeSO_4 \cdot 7H_2O$ | 5 g |
| $MnSO_4 \cdot H_2O$ | 1.6 g |
| $ZnSO_4 \cdot 7H_2O$ | 1.4 g |
| $CoCl_2 \cdot 6H_2O$ | 1.0 g |
| Filter Sterilize (0.22 micron) | |

5. SDS-PAGE of *T. reesei* MAD6 Clones Transformed with Fv43B or Fv43C

Three transformants of Fv43B and two transformants of Fv43C were grown in 96-well microtiter well plates as described in PCT publication WO 2011/038019. Culture supernatant was run on SDS-PAGE followed by coomassie blue staining with Simply Blue stain (Invitrogen). The gel was scanned and analyzed by densitometry. Image processing and band intensity quantitation was done using ImageJ (from National Institutes of Health) and by employing the Analyze Gel submenu function as described in the user guide, subsection 27.13. FIG. 15 shows SDS-PAGE of *T. reesei* MAD6 clones transformed with fv43B and fv43C. The bands corresponding to the Fv43C protein were quantified and reported as a percentage of the total protein. Fv43C protein ran as two bands on the gel, representing different glycoforms, and these were summed in the densitometry analysis.

6. Quantitative Measurements Of Amounts Of Proteins Expressed

The amounts of the proteins expressed by the quad deleted strain were compared with those achieved by the MAD6 strain. As described above, the relevant gels, FIGS. 13, 14 and 15, were scanned and analyzed by densitometry. Image processing and band intensity quantitation was done using ImageJ (from National Institutes of Health) and by employing the Analyze Gel submenu function as described in the user guide, subsection 27.13. The bands corresponding to each of the proteins of interest were quantified and reported as a percentage of the total protein. Fv43C ran as two bands on the gel, representing glycoforms, and these were summed in the densitometry analysis. Results of this analysis is summarized below in Table 2-1:

| Lane | Fv43B/Quad delete | Lane | Fv43C/Quad delete | Fv43B/MAD6 | Fv43C/MAD6 |
|---|---|---|---|---|---|
| 1 | 3% | 1 | 21% | 38% | |
| 2 | 11% | 2 | 30% | 38% | |
| 3 | 23% | 3 | 27% | 36% | |
| 4 | 17% | 4 | 2% | | 26% |
| 5 | 7% | 5 | 2% | | 26% |
| 6 | 9% | 6 | 21% | | |
| 7 | 3% | 7 | 4% | | |
| 8 | 17% | 8 | 40% | | |
| M | 4% (host) | 9 | 28% | | |
| M | 3% (host) | 10 | 19% | | |
| | | M | 3% (host) | | |

This comparison clearly indicates that expression using the MAD6 strain resulted in much more reliable expression with minimum variability (e.g., less than 20% variability) in expression levels. In contrast, using the quad deleted strain, a substantial portion of the transformants failed to express the protein of interest, and the variability of expression is substantial (e.g., greater than 50% variability).

Example 3

Generation of *Hypocrea jecorina* CBH2 DNA Libraries

The pTTTpyrG⁻cbh2 plasmid (see, e.g., PCT publication WO 2010/141779) containing the *Hypocrea jecorina* CBH2 protein encoding sequence was used as the reference sequence for the production of a DNA library encoding CBH2 variant enzymes.

SEQ ID NO:7 sets forth the reference *Hypocrea jecorina* CBH2 coding DNA sequence:

ATGATTGTCGGCATTCTCACCACGCTGGCTACGCTGGCCACACTCGCAGC

TAGTGTGCCTCTAGAGGAGCGGCAAGCTTGCTCAAGCGTCTGGGGCCAAT

GTGGTGGCCAGAATTGGTCGGGTCCGACTTGCTGTGCTTCCGGAAGCACA

TGCGTCTACTCCAACGACTATTACTCCCAGTGTCTTCCCGGCGCTGCAAG

CTCAAGCTCGTCCACGCGCGCCGCGTCGACGACTTCTCGAGTATCCCCCA

CAACATCCCGGTCGAGCTCCGCGACGCCTCCACCTGGTTCTACTACTACC

AGAGTACCTCCAGTCGGATCGGGAACCGCTACGTATTCAGGCAACCCTTT

TGTTGGGGTCACTCCTTGGGCAATGCATATTACGCCTCTGAAGTTAGCA

GCCTCGCTATTCCTAGCTTGACTGGAGCCATGGCCACTGCTGCAGCAGCT

GTCGCAAAGGTTCCCTCTTTTATGTGGCTAGATACTCTTGACAAGACCCC

TCTCATGGAGCAAACCTTGGCCGACATCCGCACCGCCAACAAGAATGGCG

GTAACTATGCCGGACAGTTTGTGGTGTATGACTTGCCGGATCGCGATTGC

GCTGCCCTTGCCTCGAATGGCGAATACTCTATTGCCGATGGTGGCGTCGC

CAAATATAAGAACTATATCGACACCATTCGTCAAATTGTCGTGGAATATT

CCGATATCCGGACCCTCCTGGTTATTGAGCCTGACTCTCTTGCCAACCTG

GTGACCAACCTCGGTACTCCAAAGTGTGCCAATGCTCAGTCAGCCTACCT

TGAGTGCATCAACTACGCCGTCACACAGCTGAACCTTCCAAATGTTGCGA

TGTATTTGGACGCTGGCCATGCAGGATGGCTTGGCTGGCCGGCAAACCAA

GACCCGGCCGCTCAGCTATTTGCAAATGTTTACAAGAATGCATCGTCTCC

-continued
```
GAGAGCTCTTCGCGGATTGGCAACCAATGTCGCCAACTACAACGGGTGGA

ACATTACCAGCCCCCCATCGTACACGCAAGGCAACGCTGTCTACAACGAG

AAGCTGTACATCCACGCTATTGGACCTCTTCTTGCCAATCACGGCTGGTC

CAACGCCTTCTTCATCACTGATCAAGGTCGATCGGGAAAGCAGCCTACCG

GACAGCAACAGTGGGGAGACTGGTGCAATGTGATCGGCACCGGATTTGGT

ATTCGCCCATCCGCAAACACTGGGGACTCGTTGCTGGATTCGTTTGTCTG

GGTCAAGCCAGGCGGCGAGTGTGACGGCACCAGCGACAGCAGTGCGCCAC

GATTTGACTCCCACTGTGCGCTCCCAGATGCCTTGCAACCGGCGCCTCAA

GCTGGTGCTTGGTTCCAAGCCTACTTTGTGCAGCTTCTCACAAACGCAAA

CCCATCGTTCCTGTAA.
```

SEQ ID NO:8 is the *Hypocrea jecorina* CBH2 full length protein sequence:

```
MIVGILTTLATLATLAASVPLEERQACSSVWGQCGGQNWSGPTCCASGST

CVYSNDYYSQCLPGAASSSSSTRAASTTSRVSPTTSRSSSATPPPGSTTT

RVPPVGSGTATYSGNPFVGVTPWANAYYASEVSSLAIPSLTGAMATAAAA

VAKVPSFMWLDTLDKTPLMEQTLADIRTANKNGGNYAGQFVVYDLPDRDC

AALASNGEYSIADGGVAKYKNYIDTIRQIVVEYSDIRTLLVIEPDSLANL

VTNLGTPKCANAQSAYLECINYAVTQLNLPNVAMYLDAGHAGWLGWPANQ

DPAAQLFANVYKNASSPRALRGLATNVANYNGWNITSPPSYTQGNAVYNE

KLYIHAIGPLLANHGWSNAFFITDQGRSGKQPTGQQQWGDWCNVIGTGFG

IRPSANTGDSLLDSFVWVKPGGECDGTSDSSAPRFDSHCALPDALQPAPQ

AGAWFQAYFVQLLTNANPSFL
```

SEQ ID NO:9 is the *Hypocrea jecorina* CBH2 mature protein sequence:

```
QACSSVWGQCGGQNWSGPTCCASGSTCVYSNDYYSQCLPGAASSSSSTRA

ASTTSRVSPTTSRSSSATPPPGSTTTRVPPVGSGTATYSGNPFVGVTPWA

NAYYASEVSSLAIPSLTGAMATAAAAVAKVPSFMWLDTLDKTPLMEQTLA

DIRTANKNGGNYAGQFVVYDLPDRDCAALASNGEYSIADGGVAKYKNYID

TIRQIVVEYSDIRTLLVIEPDSLANLVTNLGTPKCANAQSAYLECINYAV

TQLNLPNVAMYLDAGHAGWLGWPANQDPAAQLFANVYKNASSPRALRGLA

TNVANYNGWNITSPPSYTQGNAVYNEKLYIHAIGPLLANHGWSNAFFITD

QGRSGKQPTGQQQWGDWCNVIGTGFGIRPSANTGDSLLDSFVWVKPGGEC

DGTSDSSAPRFDSHCALPDALQPAPQAGAWFQAYFVQLLTNANPSFL
```

A synthetic CBH2 combinatorial library was produced by GeneOracle (Mountain View, Calif.). A number of amino acid residues of CBH2 were substituted with a plurality of other amino acid residues. Table 2-1 lists the possible substitutions of members of the CBH2 combinatorial library (numbered according to the CBH2 mature amino acid sequence).

TABLE 3-1

CBH2 Combinatorial Library Design

| Targeted Position | Wild-Type Residue | Substitution |
|---|---|---|
| 98 | P | P, Q, L |
| 111 | L | L, S |
| 182 | N | N, W |
| 291 | S | S, E |
| 316 | S | S, P |
| 362 | Q | Q, I, L |
| 400 | C | C, S |

Figure 8:
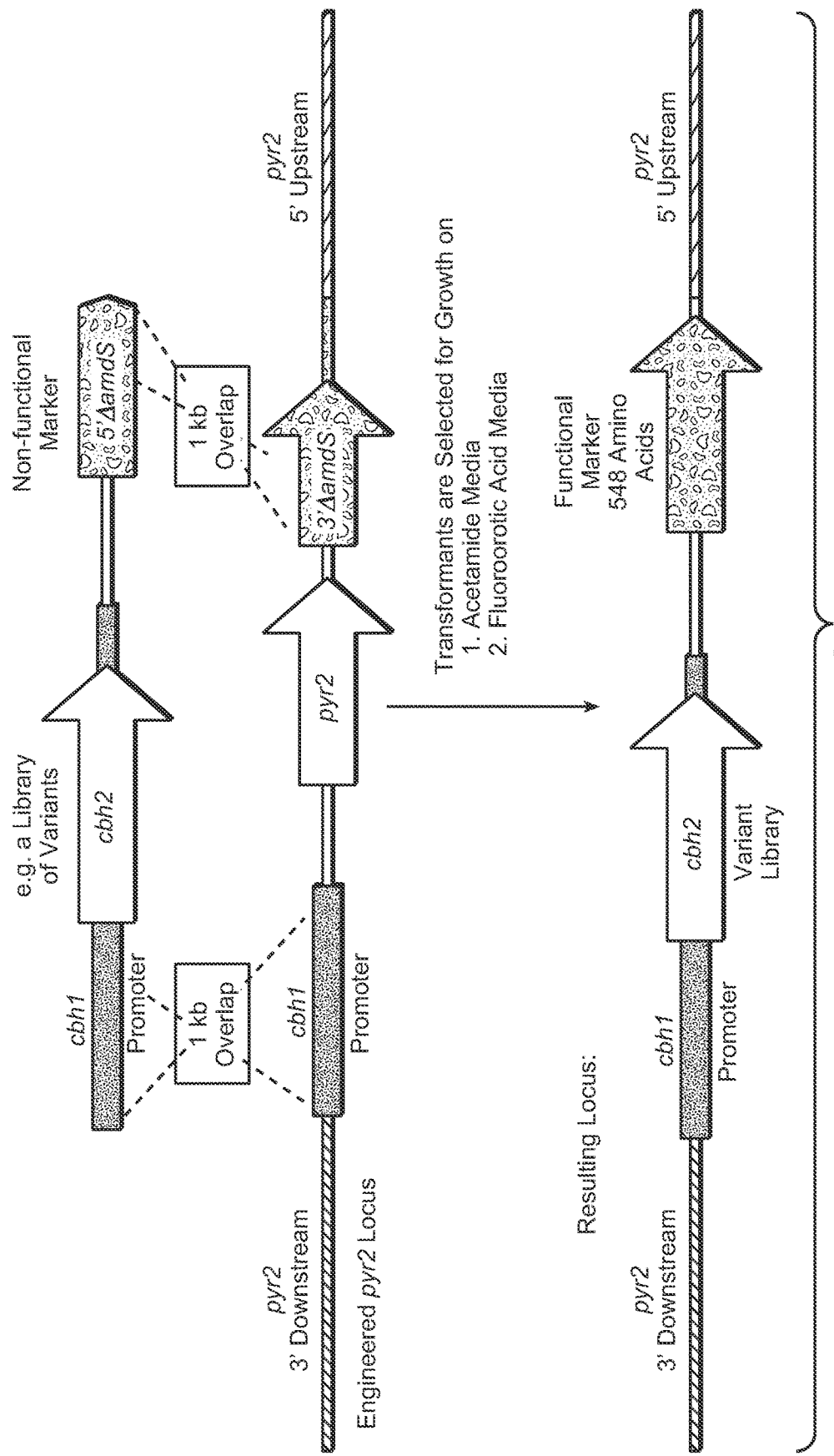
FIG. 8 illustrates the inactivation of the pyr2 selectable marker and activation of the amdS selectable marker as a consequence of introduction of a polynucleotide of a gene of interest or variant gene of interest (GOI) cassette, wherein the GOI in this example encodes a CBH2 variant.

The library was provided as purified PCR products in which primers GACCGGACGTGTTTTGCCCTTCAT (SEQ ID NO: 10) and GTGTGACCGGCTTTGGCGAGTG (SEQ ID NO: 11) were used to amplify the cbh2 gene flanked upstream by about 1.1 kb of the cbh1 promoter and downstream by about 1.85 kb of the amdS marker for forced integration in the pyr2 locus of the *H. jecorina* host strain. A schematic of the homologous recombination of the expression cassette into the screening strain is depicted in FIG. 8. The nucleotide sequence of a PCR fragment (partial cbh1 promoter, cbh2 gene, and partial amdS gene) amplified from pTTTpyrG-CBH2 using the primers above, is provided below as SEQ ID NO: 12:

```
GACCGGACGTGTTTTGCCCTTCATTTGGAGAAATAATGTCATTGCGATGT

GTAATTTGCCTGCTTGACCGACTGGGGCTGTTCGAAGCCCGAATGTAGGA

TTGTTATCCGAACTCTGCTCGTAGAGGCATGTTGTGAATCTGTGTCGGGC

AGGACACGCCTCGAAGGTTCACGGCAAGGGAAACCACCGATAGCAGTGTC

TAGTAGCAACCTGTAAAGCCGCAATGCAGCATCACTGGAAAATACAAACC

AATGGCTAAAAGTACATAAGTTAATGCCTAAAGAAGTCATATACCAGCGG

CTAATAATTGTACAATCAAGTGGCTAAACGTACCGTAATTTGCCAACGGC

TTGTGGGGTTGCAGAAGCAACGGCAAAGCCCCACTTCCCCACGTTTGTTT

CTTCACTCAGTCCAATCTCAGCTGGTGATCCCCCAATTGGGTCGCTTGTT

TGTTCCGGTGAAGTGAAAGAAGACAGAGGTAAGAATGTCTGACTCGGAGC

GTTTTGCATACAACCAAGGGCAGTGATGGAAGACAGTGAAATGTTGACAT

TCAAGGAGTATTTAGCCAGGGATGCTTGAGTGTATCGTGTAAGGAGGTTT

GTCTGCCGATACGACGAATACTGTATAGTCACTTCTGATGAAGTGGTCCA

TATTGAAATGTAAAGTCGGCACTGAACAGGCAAAAGATTGAGTTGAAACT

GCCTAAGATCTCGGGCCCTCGGGCCTTCGGCCTTTGGGTGTACATGTTTG

TGCTCCGGGCAAATGCAAAGTGTGGTAGGATCGAACACACTGCTGCCTTT

ACCAAGCAGCTGAGGGTATGTGATAGGCAAATGTTCAGGGGCCACTGCAT

GGTTTCGAATAGAAAGAGAAGCTTAGCCAAGAACAATAGCCGATAAAGAT

AGCCTCATTAAACGGAATGAGCTAGTAGGCAAAGTCAGCGAATGTGTATA

TATAAAGGTTCGAGGTCCGTGCCTCCCTCATGCTCTCCCATCTACTCAT

CAACTCAGATCCTCCAGGAGACTTGTACACCATCTTTTGAGGCACAGAAA

CCCAATAGTCAACCATCACAAGTTTGTACAAAAAAGCAGGCTCCGCGGCC

GCCCCCTTCACCCACCATGATTGTCGGCATTCTCACCACGCTGGCTACGC

TGGCCACACTCGCAGCTAGTGTGCCTCTAGAGGAGCGGCAAGCTTGCTCA
```

-continued
```
AGCGTCTGGTAATTATGTGAACCCTCTCAAGAGACCCAAATACTGAGATA
TGTCAAGGGCCAATGTGGTGGCCAGAATTGGTCGGGTCCGACTTGCTGT
GCTTCCGGAAGCACATGCGTCTACTCCAACGACTATTACTCCCAGTGTCT
TCCCGGCGCTGCAAGCTCAAGCTCGTCCACGCGCGCCGCGTCGACGACTT
CTCGAGTATCCCCCACAACATCCCGGTCGAGCTCCGCGACGCCTCCACCT
GGTTCTACTACTACCAGAGTACCTCCAGTCGGATCGGGAACCGCTACGTA
TTCAGGCAACCCTTTTGTTGGGGTCACTCCTTGGGCCAATGCATATTACG
CCTCTGAAGTTAGCAGCCTCGCTATTCCTAGCTTGACTGGAGCCATGGCC
ACTGCTGCAGCAGCTGTCGCAAAGGTTCCCTCTTTTATGTGGCTGTAGGT
CCTCCCGGAACCAAGGCAATCTGTTACTGAAGGCTCATCATTCACTGCAG
AGATACTCTTGACAAGACCCCTCTCATGGAGCAAACCTTGGCCGACATCC
GCACCGCCAACAAGAATGGCGGTAACTATGCCGGACAGTTTGTGGTGTAT
GACTTGCCGGATCGCGATTGCGCTGCCCTTGCCTCGAATGGCGAATACTC
TATTGCCGATGGTGGCGTCGCCAAATATAAGAACTATATCGACACCATTC
GTCAAATTGTCGTGGAATATTCCGATATCCGGACCCTCCTGGTTATTGGT
ATGAGTTTAAACACCTGCCTCCCCCCCCCCTTCCCTTCCTTTCCCGCCGG
CATCTTGTCGTTGTGCTAACTATTGTTCCCTCTTCCAGAGCCTGACTCTC
TTGCCAACCTGGTGACCAACCTCGGTACTCCAAAGTGTGCCAATGCTCAG
TCAGCCTACCTTGAGTGCATCAACTACGCCGTCACACAGCTGAACCTTCC
AAATGTTGCGATGTATTTGGACGCTGGCCATGCAGGATGGCTTGGCTGGC
CGGCAAACCAAGACCCGGCCGCTCAGCTATTTGCAAATGTTTACAAGAAT
GCATCGTCTCCGAGAGCTCTTCGCGGATTGGCAACCAATGTCGCCAACTA
CAACGGGTGGAACATTACCAGCCCCCATCGTACACGCAAGGCAACGCTG
TCTACAACGAGAAGCTGTACATCCACGCTATTGGACCTCTTCTTGCCAAT
CACGGCTGGTCCAACGCCTTCTTCATCACTGATCAAGGTCGATCGGGAAA
GCAGCCTACCGGACAGCAACAGTGGGGAGACTGGTGCAATGTGATCGGCA
CCGGATTTGGTATTCGCCCATCCGCAAACACTGGGGACTCGTTGCTGGAT
TCGTTTGTCTGGGTCAAGCCAGGCGGCGAGTGTGACGGCACCAGCGACAG
CAGTGCGCCACGATTTGACTCCCACTGTGCGCTCCCAGATGCCTTGCAAC
CGGCGCCTCAAGCTGGTGCTTGGTTCCAAGCCTACTTTGTGCAGCTTCTC
ACAAACGCAAACCCATCGTTCCTGTAAAAGGGTGGGCGCGCCGACCCAGC
TTTCTTGTACAAAGTGGTGATCGCGCCGCGCGCCAGCTCCGTGCGAAAGC
CTGACGCACCGGTAGATTCTTGGTGAGCCCGTATCATGACGGCGGCGGGA
GCTACATGGCCCCGGGTGATTTATTTTTTTGTATCTACTTCTGACCCTT
TTCAAATATACGGTCAACTCATCTTTCACTGGAGATGCGGCCTGCTTGGT
ATTGCGATGTTGTCAGCTTGGCAAATTGTGGCTTTCGAAAACACAAAACG
ATTCCTTAGTAGCCATGCATTTTAAGATAACGGAATAGAAGAAAGAGGAA
ATTAAAAAAAAAAAAAAACAAACATCCCGTTCATAACCCGTAGAATCGC
CGCTCTTCGTGTATCCCAGTACCAGTTTATTTTGAATAGCTCGCCCGCTG
GAGAGCATCCTGAATGCAAGTAACAACCGTAGAGGCTGACACGGCAGGTG
TTGCTAGGGAGCGTCGTGTTCTACAAGGCCAGACGTCTTCGCGGTTGATA
```

-continued
```
TATATGTATGTTTGACTGCAGGCTGCTCAGCGACGACAGTCAAGTTCGCC
CTCGCTGCTTGTGCAATAATCGCAGTGGGGAAGCCACACCGTGACTCCCA
TCTTTCAGTAAAGCTCTGTTGGTGTTTATCAGCAATACACGTAATTTAAA
CTCGTTAGCATGGGGCTGATAGCTTAATTACCGTTTACCAGTGCCATGGT
TCTGCAGCTTTCCTTGGCCCGTAAAATTCGGCGAAGCCAGCCAATCACCA
GCTAGGCACCAGCTAAACCCTATAATTAGTCTCTTATCAACACCATCCGC
TCCCCCGGGATCAATGAGGAGAATGAGGGGGATGCGGGGCTAAAGAAGCC
TACATAACCCTCATGCCAACTCCCAGTTTACACTCGTCGAGCCAACATCC
TGACTATAAGCTAACACAGAATGCCTCAATCCTGGGAAGAACTGGCCGCT
GATAAGCGCGCCCGCCTCGCAAAAACCATCCCTGATGAATGGAAAGTCCA
GACGCTGCCTGCGGAAGACAGCGTTATTGATTTCCCAAAGAAATCGGGGA
TCCTTTCAGAGGCCGAACTGAAGATCACAGAGGCCTCCGCTGCAGATCTT
GTGTCCAAGCTGGCGGCCGGAGAGTTGACCTCGGTGGAAGTTACGCTAGC
ATTCTGTAAACGGGCAGCAATCGCCCAGCAGTTAGTAGGGTCCCCTCTAC
CTCTCAGGGAGATGTAACAACGCCACCTTATGGGACTATCAAGCTGACGC
TGGCTTCTGTGCAGACAAACTGCGCCCACGAGTTCTTCCCTGACGCCGCT
CTCGCGCAGGCAAGGGAACTCGATGAATACTACGCAAAGCACAAGAGACC
CGTTGGTCCACTCCATGGCCTCCCCATCTCTCTCAAAGACCAGCTTCGAG
TCAAGGTACACCGTTGCCCCTAAGTCGTTAGATGTCCCTTTTTGTCAGCT
AACATATGCCACCAGGGCTACGAAACATCAATGGGCTACATCTCATGGCT
AAACAAGTACGACGAAGGGGACTCGGTTCTGACAACCATGCTCCGCAAAG
CCGGTGCCGTCTTCTACGTCAAGACCTCTGTCCCGCAGACCCTGATGGTC
TGCGAGACAGTCAACAACATCATCGGGCGCACCGTCAACCCACGCAACAA
GAACTGGTCGTGCGGCGGCAGTTCTGGTGGTGAGGGTGCGATCGTTGGGA
TTCGTGGTGGCGTCATCGGTGTAGGAACGGATATCGGTGGCTCGATTCGA
GTGCCGGCCGCGTTCAACTTCCTGTACGGTCTAAGGCCGAGTCATGGGCG
GCTGCCGTATGCAAAGATGGCGAACAGCATGGAGGGTCAGGAGACGGTGC
ACAGCGTTGTCGGGCCGATTACGCACTCTGTTGAGGGTGAGTCCTTCGCC
TCTTCCTTCTTTTCCTGCTCTATACCAGGCCTCCACTGTCCTCCTTTCTT
GCTTTTTATACTATATACGAGACCGGCAGTCACTGATGAAGTATGTTAGA
CCTCCGCCTCTTCACCAAATCCGTCCTCGGTCAGGAGCCATGGAAATACG
ACTCCAAGGTCATCCCCATGCCCTGGCGCCAGTCCGAGTCGGACATTATT
GCCTCCAAGATCAAGAACGGCGGGCTCAATATCGGCTACTACAACTTCGA
CGGCAATGTCCTTCCACACCCTCCTATCCTGCGCGGCGTGGAAACCACCG
TCGCCGCACTCGCCAAAGCCGGTCACACC.
```

Protoplasts of the AD5 H. jecorina strain (Δegl1, Δegl2, Δcbh1, Δcbh2, Δbgl1) described in Example 1 were transformed with the linear DNA library as described (U.S. patent application publication US 2006/0094080) and grown on selective agar containing acetamide at 28° C. for 7 days (0.6 g/L acetamide, 1.68 g/L CsCl, 20 g/L glucose, 6 g/L KH2PO4, 0.6 g/L MgSO4.7H20, 0.6 g/L CaCl2.2H20, 0.5 g/L uridine, trace element salts, 10 g/L low melting point agarose). After 24 hours the agar was overlaid with selective agar supplemented with 1.2 g/L fluoroorotic acid (FOA). A total of 380 colonies were transferred to potato dextrose agar plates containing 1.2 g/L FOA and incubated at 28° C. for 4-5 days. Spores were transferred to fresh potato dextrose agar plates, which were incubated at 28° C. for 3 days.

Alternatively, protoplasts of the MAD6 strain described in Example 1 can be employed instead of AD5 for expression of variant library members. Likewise, protoplasts of derivatives of the MAD6 strain in which additional cellulases have been inactivated can be used for this purpose. Such derivatives would exhibit even less background cellulase activity.

For CBH2 variant protein production, spores were transferred using a 96-pin replicator to 200 µl glycine minimal medium supplemented with 2% glucose/sophorose mixture in a PVDF filter plate: 6.0 g/L glycine, 4.7 g/L $(NH_4)_2SO_4$; 5.0 g/L $KH_2PO_4$; 1.0 g/L $MgSO_4.7H_2O$; 33.0 g/L PIPPS; pH 5.5; with sterile addition of a 2% glucose/sophorose mixture as the carbon source, 10 ml/L of 100 g/L of $CaCl_2$, 2.5 ml/L of T. reesei trace elements (400×): 175 g/L Citric acid anhydrous; 200 g/L $FeSO_4.7H_2O$; 16 g/L $ZnSO_4.7H_2O$; 3.2 g/L $CuSO_4.5H_2O$; 1.4 g/L $MnSO_4.H_2O$; 0.8 g/L $H_3BO_3$. Each CBH2 variant was grown in quadruplicate. After sealing the plate with an oxygen permeable membrane, the plates were incubated at 28° C. for 6 days, while shaking at 200 rpm. Supernatant was harvested by transferring the culture medium to a microtiter plate under low pressure.

Figure 16A:
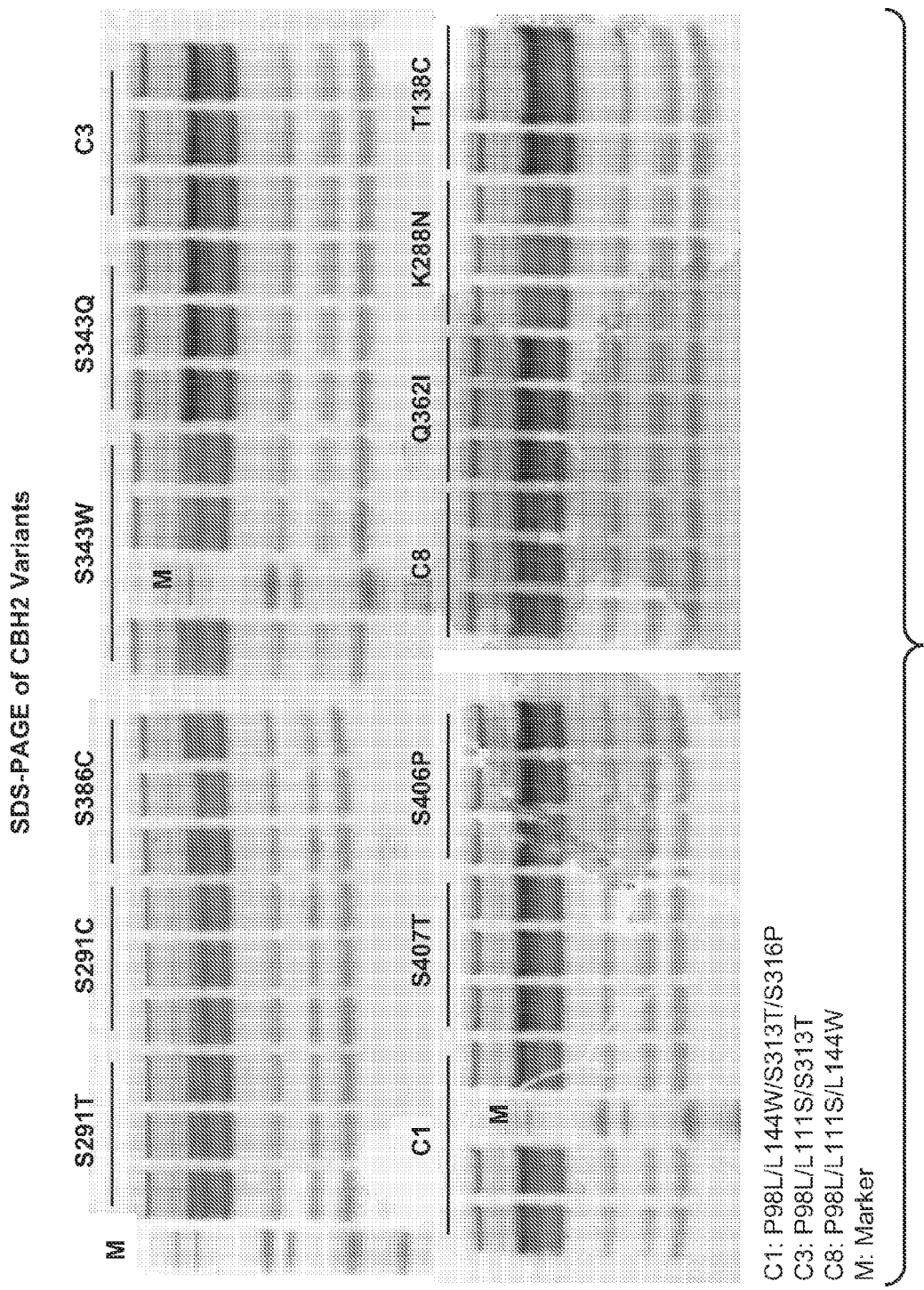
FIG. 16A is a picture of 4 SDS-PAGE examining the CBH2 variants as described in Example 3.
Figure 16B:
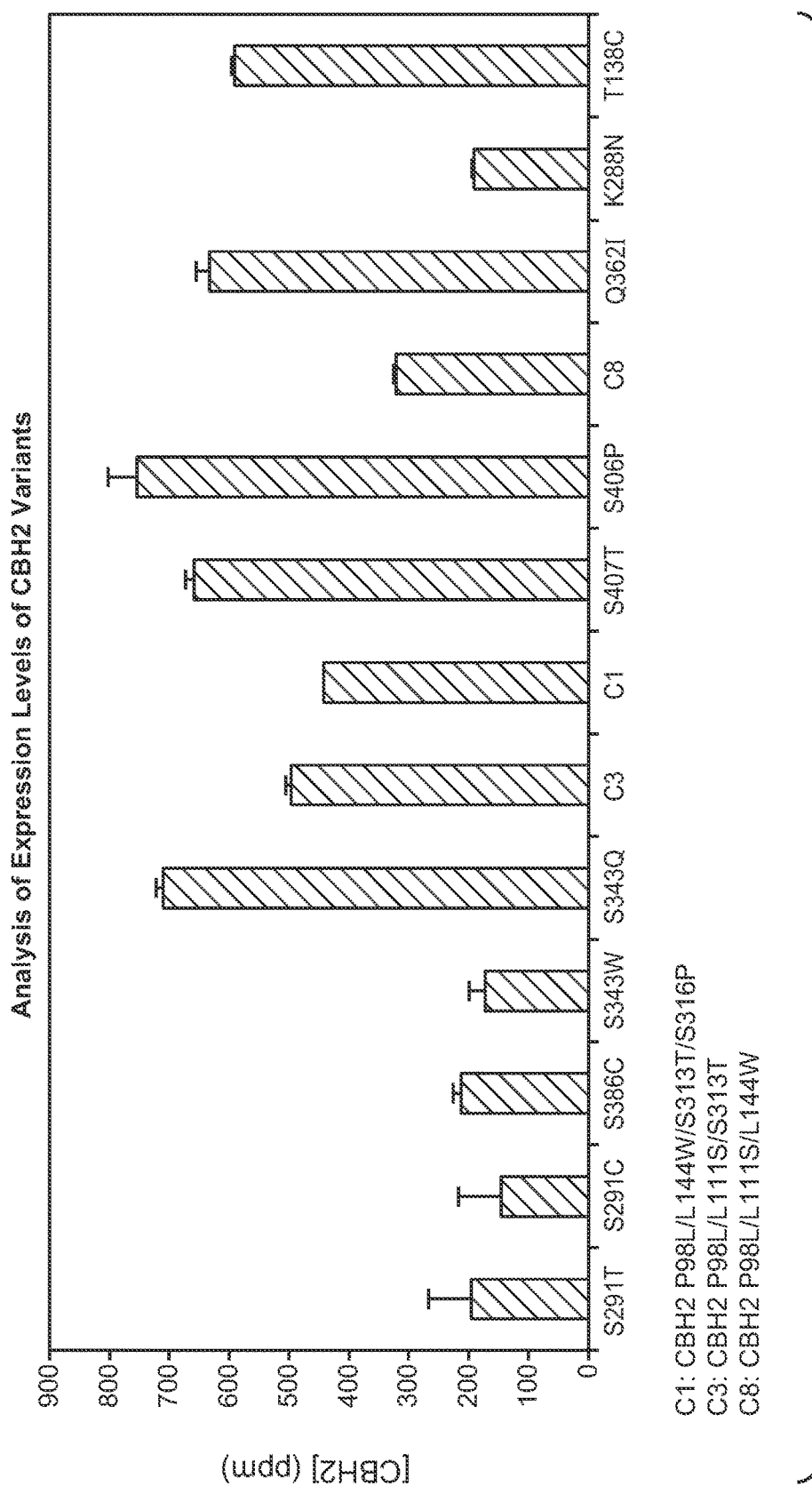
FIG. 16B depicts the average expression of CBH2 variants as described in Example 3.

The CBH2 variants were tested for properties of interest. Expressions of individual variants were examined using SDS PAGE. FIG. 16A is a picture of four SDS-PAGE, showing the expression of a number of variants; FIG. 16B depicts the average production levels for these variants, with the error bars indicating variability of expression. The specific activities for washed dilute acid pretreated cornstover (PCS 50° C.), for corncob at 50° C. (CC 50° C.), and for corncob at 57° C. (CC 57° C.) were determined. A total of ten variants that showed improved activity on corn cob at 57° C. were isolated. Genomic DNA of these strains was isolated and their cbh2 gene sequences determined. The substitutions and performance index for specific activities of combinatorial library variants on corncob and corn stover is shown in Table 3-2. The performance index for specific activities were determined based on normalized protein expression levels of the variants.

TABLE 3-2

CBH2 Combinatorial Variants with Improved Activity on Corncob at 57° C.

| Variant | CC 57° C. | CC 50° C. | PCS 50° C. |
|---|---|---|---|
| CBH2.S291E/Q362I | 1.2 | 0.97 | 1.13 |
| CBH2.P98Q/S316P/Q362L/L439P | 1.52 | 0.97 | 0.1 |
| CBH2.P98Q/N182W/S291E/S316P/C400S | 1.26 | 0.97 | 0.75 |
| CBH2.P98Q/N182W/S291E/S316P/C400S | 1.24 | 0.97 | 1.02 |
| CBH2.P98L/N182W/S291E/Q362I/C400S | 1.26 | 0.97 | 1.05 |
| CBH2.P98L/N182W/S291E/Q362I/C400S | 1.28 | 0.97 | 1.14 |
| CBH2.T74S/P98L/N182W/S291E | 1.31 | 0.97 | 1.13 |
| CBH2.P98L/N182W/S291E/S316P/Q362I | 1.26 | 0.97 | 1.22 |
| CBH2.N182W/S291E/Q362L/C400S | 1.3 | 0.97 | 1.08 |
| CBH2.S291E/Q362L | 1.29 | 0.97 | 1.18 |

PCS 50° C. Corn stover was pretreated with 2% w/w $H_2SO_4$ as described (Schell et al., J Appl Biochem Biotechnol, 105:69-86, 2003) and followed by multiple washes with deionized water to obtain a paste having a pH of 4.5. Sodium acetate buffer (pH 5.0) was then added to a final concentration of 50 mM sodium acetate, and, this mixture was then titrated to pH 5.0 using 1 N NaOH as appropriate. The cellulose concentration in the reaction mixture was approximately 7%. Sixty-five (65) µL of this cellulose suspension was added per well to a 96-well microtiter plate (Nunc Flat Bottom PS). To each well, 10 µL of the enzyme sample was added, each containing 49 µg protein in supernatant from a quad deleted strain (Δegl1, Δegl2, Δcbh1, Δcbh2).

Up to 20 µL of culture supernatants from H. jecorina cells expressing either wild-type CBH2 or CBH2 variants were added. Compensating volumes of acetate buffer were added to make up for differences in total volume. After sealing of the plates, they were incubated at 50° C. while shaking at 200 rpm. After 2 days the plate was put on ice for 5 min and 100 µL of 100 mM glycine pH 10.0 was added. After mixing, the plate was centrifuged at 3000 rpm for 5 min. A volume of 10 µL supernatant was diluted in 190 µL water. Ten (10) µL of the diluted solution was transferred to a new 96-well microtiterplate (Costar Flat Bottom PS) containing, in each well, 100 µL ABTS glucose assay mixture (2.74 mg/ml 2,2' azino-bis(3-ethylbenzo-thiazoline-6-sulfonic acid, 1 U/ml horseradish peroxidase type VI, 1 U/ml glucose oxidase) and increase in $A_{420}$ was recorded in a microtiter plate spectrophotometer (Spectramax Plus 384, Molecular Devices). A range of glucose concentrations was included as a standard on each plate (0; 0.008; 0.016; 0.031; 0.063; 0.125; 0.25; 0.5; 1 mg/ml). Assays were done in duplicate. A dose response curve was generated for the wild-type CBH2 by fitting the data with a Temkin isotherm equation (y=a+b(ln(1+c*x))) and the activities of the CBH2 variants were divided by a calculated activity of wild-type CBH2 of the same plate to yield a performance index.

Corncob 50° C. Corn cob was ground to pass through a 0.9 mm screen, followed by pretreated in accordance with the method described in Example 4 of PCT Publication WO 2006/110901. Pretreated corn cob was used as a 7% cellulose suspension in 50 mM sodium acetate pH 5.0. Seventy (70) µL of the suspension was added per well to a 96-well microtiter plate (Nunc Flat Bottom PS). To each well 10 µL solution was added containing 46.55 µg protein of supernatant from a quad deleted strain (Δegl1, Δegl2, Δcbh1, Δcbh2), supplemented with 4.90 µg T. reesei CBH1, 6.84 µg T. reesei Xyn2 Y5 (Xiong et al, Extremophiles 8:393-400, 2004), 2.28 µg Fusarium verticillioides (Fv) 51A, 5.32 µg Fv3A, 0.76 µg Fv43D, and 2.45 µg T. reesei BGL1. The Fusarium verticillioides enzymes have been described in PCT publication WO/2011/038019.

Up to 20 µL of supernatant from H. jecorina cells expressing either wild-type CBH2 or a CBH2 variant were added. Compensating volumes of acetate buffer were added to make up for differences in total volume. The plate was incubated at 50° C. while shaking at 200 rpm. After 2 days the plate was put on ice for 5 min and 100 µL of 100 min glycine pH 10.0 was added. After mixing, the plate was centrifuged at 3000 rpm for 5 min. A volume of 10 µL supernatant was diluted in 190 µL water. Ten (10) µl of the diluted solution was transferred to a new 96-well microtiterplate (Costar Flat Bottom PS) containing 100 µL ABTS glucose assay mixture and assayed and analyzed as described above.

Corncob 57° C. Corn cob was ground to pass through a 0.9 mm screen, followed by pretreated in accordance with the method described in Example 4 of PCT WO 2006/110901. Pretreated corn cob was used as a 7% cellulose suspension in 50 mM sodium acetate pH 5.0. Seventy (70) µL of the suspension was added per well to a 96-well microtiterplate (Nunc Flat Bottom PS). To each well 10 µL solution containing 46.55 µg protein of supernatant from a quad deleted strain (Δegl1, Δegl2, Δcbh1, Δcbh2), 4.90 µg CBH1 variant (S8P/T41I/N89D/S92T/S113N/S196T/P227L/D249K/T255P/S278P/E295K/ T296P/T332Y/V403D/S411F/T462I), 6.84 μg *T. reesei* Xyn2 Y5 (Xiong et al, Extremophiles 8:393-400, 2004), 2.28 μg Fv51A, 5.32 μg Fv3A, 0.76 μg Fv43D, 2.45 μg *Talaromyces emersonii* beta-glucosidase were added. Up to 20 μL of supernatant from *H. jecorina* cells expressing either wild-type CBH2 or a CBH2 variant was added. Compensating volumes of acetate buffer were added to make up for differences in total volume. The plate was incubated at 57° C. while shaking at 200 rpm. After 2 days the plate was put on ice for 5 min and 100 μL of 100 mM glycine pH 10.0 was added. After mixing, the plate was centrifuged at 3000 rpm for 5 min. A volume of 10 μL supernatant was diluted in 190 μL water. Ten (10) μL of the diluted solution was transferred to a new 96-well microtiterplate (Costar Flat Bottom PS) containing 100 μL ABTS glucose assay mixture and assayed and analyzed as described above.

We claim:

1. A filamentous fungal host cell expression system, comprising:
   a. a fungal host cell containing in its chromosomal DNA a disruption in one or more components of non-homologous recombination (NHR) pathway, a first selectable marker that lacks a first selectable function, and a second selectable marker that is operative to confer a second selectable function, wherein said first selectable marker and said second selectable marker are different markers; and
   b. a nucleic acid molecule containing: (1) a sequence that, when introduced into said fungal host cell, confers said first selectable function to said first selectable marker, (2) a sequence operable to express one or more genes of interest, and (3) sequences upstream (5') of b (1) and b (2) and sequences downstream (3') of b (1) and b (2), wherein the upstream sequences have substantial homologies to sequences upstream (5') of the first selectable marker and said second selectable marker in the host cell chromosomal DNA and wherein the downstream sequences have substantial homologies to sequences downstream (3') of the first selectable marker and second selectable marker in the host cell chromosomal DNA:
   wherein said homologous sequences cause a homologous recombination event that results in a functional first selectable marker in the host cell chromosomal DNA, removal of said second selectable marker from the host cell chromosomal DNA, and expression of said gene of interest.

2. The filamentous fungal host cell expression system of claim 1, wherein said one or more components of the NHR pathway are selected from the group consisting of ku80, ku70, rad50, mre11, xrs2, lig4, and xrs.

3. The filamentous fungal host cell expression system of claim 1, wherein said first selectable marker and said second selectable marker are selected from the group consisting of alsR, amdS, hygR, pyr2, pyr4, pyrG, sucA, a bleomycin resistance marker, a blasticidin resistance marker, a pyrithiamine resistance marker, a chlorimuron ethyl resistance marker, a neomycin resistance marker, an adenine pathway gene, a tryptophan pathway gene, and thymidine kinase.

4. The filamentous fungal host cell expression system of claim 1, wherein said fungal host cell is from a genus selected from the group consisting of *Trichoderma, Penicillium, Aspergillus, Humicola, Chrysosporium, Fusarium, Neurospora,* and *Emericella*.

5. The filamentous fungal host cell expression system of claim 4, wherein the *Trichoderma* is *T. reesei*.

6. The filamentous fungal host cell expression system of claim 4, wherein the *Aspergillus* is *A. niger*.

7. The filamentous fungal host cell expression system of claim 1, wherein the gene of interest is selected from the group consisting of hemicellulases, peroxidases, proteases, cellulases, xylanases, lipases, phospholipases, esterases, cutinases, pectinases, keratinases, reductases, oxidases, phenol oxidases, lipoxygenases, ligninases, pullulanases, tannases, pentosanases, malanases, beta-glucanases, arabinosidases, hyaluronidase, chondroitinase, laccase, amylases, glucoamylases, and mixtures thereof.

8. The filamentous fungal host cell expression system of claim 1, wherein the gene of interest is selected from the group consisting of acetyl esterases, aminopeptidases, amylases, arabinases, arabinofuranosidases, carboxypeptidases, catalases, cellulases, chitinases, chymosin, cutinase, deoxyribonucleases, epimerases, esterases, α-galactosidases, β-galactosidases, α-glucanases, glucan lyases, endo- β-glucanases, glucoamylases, glucose oxidases, α-glucosidases, β-glucosidases, glucuronidases, hemicellulases, hexose oxidases, hydrolases, invertases, isomerases, laccases, lipases, lyases, mannosidases, oxidases, oxidoreductases, pectate lyases, pectin acetyl esterases, pectin depolymerases, pectin methyl esterases, pectinolytic enzymes, peroxidases, phenoloxidases, phytases, polygalacturonases, proteases, rhamno-galacturonases, ribonucleases, thaumatin, transferases, transport proteins, transglutaminases, xylanases, hexose oxidases, and combinations thereof.

9. The filamentous fungal host cell expression system of claim 1, wherein the gene of interest is selected from the group consisting peptide hormones, growth factors, clotting factors, chemokines, cytokines, lymphokines, antibodies, receptors, adhesion molecules, microbial antigens, and fragments thereof.

10. A method of expressing a gene of interest in the filamentous fungal host cell of claim 1, comprising introducing into said filamentous fungal host cell said nucleic acid molecule, growing said host cells, and selecting for host cells that have said first selectable function but lack said second selectable function.

11. The method of claim 10, further comprising assaying for the expression of said gene of interest.

12. The method of claim 11, further comprising assaying for a biochemical function of a polypeptide encoded by said gene of interest.

13. The filamentous fungal host cell expression system of claim 1, wherein said first selectable marker and said second selectable marker are located at the same locus in the host cell's chromosomal DNA.

* * * * *